US007589170B1

(12) United States Patent
Smythe et al.

(10) Patent No.: US 7,589,170 B1
(45) Date of Patent: Sep. 15, 2009

(54) SYNTHESIS OF CYCLIC PEPTIDES

(75) Inventors: Mark Leslie Smythe, Bardon (AU);
Wim Denis Frans Meutermans, Terrace (AU); Gregory Thomas Bourne, Coopers Plains (AU); Ross Peter McGeary, St. Lucia (AU)

(73) Assignee: The University of Queensland (AU)

( * ) Notice: Subject to any disclaimer, the term of this patent is extended or adjusted under 35 U.S.C. 154(b) by 0 days.

(21) Appl. No.: 09/806,036

(22) PCT Filed: Sep. 24, 1999

(86) PCT No.: PCT/AU99/00813

§ 371 (c)(1),
(2), (4) Date: Jul. 5, 2001

(87) PCT Pub. No.: WO00/18790

PCT Pub. Date: Apr. 6, 2000

(30) Foreign Application Priority Data

Sep. 25, 1998 (AU) .................................... PP 6164

(51) Int. Cl.
C07K 5/12 (2006.01)
C07K 7/64 (2006.01)
C07K 1/02 (2006.01)
C07K 1/04 (2006.01)

(52) U.S. Cl. ................ 530/317; 530/300; 530/327; 530/330; 530/333; 530/338; 514/11; 514/10; 514/14

(58) Field of Classification Search ............ 514/11, 514/10, 2, 14; 530/317, 300, 333, 338, 344, 530/327, 330
See application file for complete search history.

(56) References Cited

U.S. PATENT DOCUMENTS

| 3,704,246 A | 11/1972 | Bodanszky et al. ......... 260/333 |
| 5,192,746 A | 3/1993 | Lobl et al. .................... 514/11 |
| 5,739,386 A | 4/1998 | Holmes ...................... 562/437 |
| 5,869,447 A | 2/1999 | Henke et al. ................... 514/9 |

FOREIGN PATENT DOCUMENTS

| EP | 0 091 330 A1 | 10/1983 |
| WO | WO 98/17628 | 4/1998 |
| WO | WO 99/26902 | 6/1999 |
| WO | WO 00/18790 | 4/2000 |

OTHER PUBLICATIONS

Voet et al., Biochemistry (published by John Wiley & Sons, Inc.) p. 62-63 (1990).*
Derwent abstract Accession No. 93-076437/09, WO 9303056 A1 (Kolbeck W.) Feb. 18, 1993.
Derwent abstract Accession No. 95-404082/51, WO 9530694 A1 (Astra AB) Nov. 16, 1995.
Derwent abstract Accession No. 96-279515/29, EP 717048 A1 (Hoechst AG) Jun. 19, 1996.
Derwent abstract Accession No. 98-168442/15, US 5721210 A (Tanabe Seiyaku Co.) Feb. 24, 1994.
International Search Report for PCT/AU99/00813, mailed Nov. 5, 1999.
Sakurada et al., "Antinociceptive Mechanisms of [D-Arg$^2$]-Dermorphin Tripeptide Analogs," *J. Pharm. Exp. Thera.*, 263(2):793-799, 1992.
Salvadori et al., "Synthesis and Pharmacological Activity of Dermorphin and its N-Terminal Sequences," *Int. J. Peptide Protein Res.*, 19:536-542, 1982.
Partial Supplementary European Search Report for European Counterpart Application No. 99948610.3, mailed Sep. 12, 2002.
Canne et al., "Extending the Applicability of Native Chemical Ligation," *J. Am. Chem. Soc.*, 118:5891-5896, 1996.
Hyde et al., "Some 'Difficult Sequences' Made Easy: A Study of Interchain Association in Solid-Phase Peptide Synthesis," *Int. J. Peptide Protein Res.*, 43(5):431-440, 1994.
Jensen et al., "Backbone Amide Linker (BAL) Strategy for Solid-Phase Synthesis of C-Terminal-Modified and Cyclic Peptides," *J. Am. Chem. Soc.*, 120:5441-5452, 1998.
Johnson et al., "N,O-bisFmoc Derivatives of N-(2-Hydroxy-4-Methoxybenzyl)-Amino Acids: Useful Intermediates in Peptide Synthesis," *J. Peptide Sci.*, 1:11-25, 1995.
Johnson and Quibell, "The N-(2-Hydroxybenzyl) Protecting Group for Amide Bond Protection in Solid Phase Peptide Synthesis," *Tethredron Letters*, 35(3):463-466,1994.

(Continued)

*Primary Examiner*—Chih-Min Kam
(74) *Attorney, Agent, or Firm*—Mark D. Moore; Haynes and Boone, LLP

(57) ABSTRACT

This invention relates to methods for preparing cyclic peptides and peptidomimetic compounds in solution and bound to solid supports, and to cyclic peptide or peptidomimetic libraries for use in drug screening programs. In particular, the invention relates to a generic strategy for synthesis of cyclic peptides or peptidomimetics that enables the efficient synthesis under mild conditions of a wide variety of desired compounds. Two approaches were evaluated for their improvements in solution and solid phase synthesis of small cyclic peptides: positioning reversible N-amide substituents in the sequence; and applying native ligation chemistry in an intramolecular sense. Systematic investigation of the effects of preorganising peptides prior to cyclisation by using peptide cyclisation auxiliaries, and developing new linkers and peptide cyclisation auxiliaries to aid cyclic peptide synthesis gives surprising improvements in both yields and purity of products compared to the prior art methods. The combination of these technologies provides a powerful generic approach for the solution and solid phase synthesis of small cyclic peptides. The ring contraction and N-amide substitution technology of the invention provide improved methods for the synthesis of cyclic peptides and peptidomimetics. When used in conjunction with linker strategies, this combination provides solid-phase avenues to cyclic peptides and peptidomimetics.

24 Claims, 11 Drawing Sheets

OTHER PUBLICATIONS

Kemp et al., "Intramolecular O,N-Acyl Transfer via Cyclic Intermediates of Nine and Twelve Members. Models of Extension of the Amine Capture Strategy for Peptide Synthesis," *J. Org. Chem.*, 46:490-498, 1981.

Meutermans et al., "Synthesis of Difficult Cyclic Peptides by Inclusion of a Novel Photolabile Auxiliary in a Ring Contraction Strategy," *J. Am. Shem. Soc.*, 121:9790-9796, 1999.

Pashayan et al., "Photorearrangement of Ortho-Nitrobenzaldehyde and its Derivatives," Translated from *Kimiya Vysokikh Energii*, 10(2):155-160, Mar.-Apr. 1976. Original article submitted Mar. 3, 1975.

Partial Supplementary European Search Report for European Application No. 99950390.7, counterpart to U.S. Appl. No. 09/787,840, mailed Sep. 12, 2002.

Supplementary European Search Report for European Application No. 99950390.7, counterpart to U.S. Appl. No. 09/787,840, mailed Sep. 10, 2004.

Beusen et al., "Conformational Mimicry: Synthesis and Solution Conformation of a Cyclic Somatostatin Hexapeptide Containing a Tetrazole cis Amide Bond Surrogate," *Biopolymers*, 36(2):181-260, 1995.

Botti et al., "Cyclic Peptides from Linear Unprotected Peptide Precursors Through Thiazolidine Formation," *J. Am. Chem. Soc.*, 118(42):10018-10024, 1996.

Cavelier-Frontin et al., "How to Perform Small Peptide Cyclizations," *Theochem*, 105:125-130, 1993.

Ehrlich et al., "Cyclization of All-L-Pentapeptides by Means of 1-Hydroxy-7-Azabenzotriazole-Derived Uronium and Phosphonium Reagents," *J. Organic Chem.*, 61(25):8831-8838, 1996.

Elseviers et al., "Evidence for the Bioactive Conformation in a Cyclic Hexapeptide Analogue of Somatostatin Containing a cis Peptide Bond Mimic," *Biochem. Biophys. Res. Comm.*, 154(2):515-521, 1988.

Ruckle et al., "Pseudo-Prolines in Cyclic Peptides: Conformational Stabilisation of cyclo[Pro-Thr($\psi^{Me,Me}$pro)-Pro]," *Tetrahedron*, 55(37):11281-11288, 1999.

Shao et al., "A Novel Method to Synthesize Cyclic Peptides," *Tetrahedron Ltrs.*, 39(23):3911-3914, 1998.

Zhang et al., "Lactone and Lactam Library Synthesis by Silver Ion-Assisted Orthogonal Cyclization of Unprotected Peptides," *J. Am. Chem. Soc.*, 121(14):3311-3320, 1999.

Zhang et al., "Synthesis and Application of Unprotected Cyclic Peptides as Building Blocks for Peptide Dendrimers," *J. Am. Chem. Soc.*, 119(10):2363-2370, 1997.

Partial European Search Report for European Counterpart Application No. 99948610.3, mailed Jul. 16, 2004.

European Search Report for Application No. EP 99948610.3, Feb. 5, 2005.

Examination Report for Application No. EP 99948610.3, Sep. 1999.

Shinobo Sakurada, et al., *Antinociceptive Mechanismd of [D-Arg-2]-Dermorphin Tripeptide Analogs*, The Journal of Pharmacology and Experimental Therapeutics, 1992, pp. 793-799, vol. 263, No. 2.

Severo Salvadori, et al., *Synthesis and Pharmacological Activity of Dermorphin and its N-terminal Sequences*, International Journal of Peptide Protein Research, 1982, pp. 536-542, vol. 19.

Florine Cavelier-Frontin, et al., *How to Perform Small Peptide Cyclizations*, Journal of Molecular Structure, 1993, pp. 125-130, vol. 286.

Angelika Ehrlich, et al., *Cyclization of all-L-Pentapeptides by Means of 1-Hydroxy-7-azabenzotriazole-Derived Uronium and Phosphonium Reagents*, Journal of Organic Chemistry, 1996, pp. 8831-8838, vol. 61, No. 25.

Denise D. Beusen, et al., *Conformational Mimicry: Synthesis and Solution Conformation of a Cyclic Somatostatin Hexapeptide Containing a Tetrazole cis Amide Bond Surrogate*, Biopolymers, 1995, pp. 181-200, vol. 36, No. 2.

M. Elseviers, et al., *Evidence for the Bioactive Conformation in a Cyclic Hexapeptide Analogue of Somatostatin Containing a cis-peptide Bond Mimic*, Biochemical and Biophysical Research Communications, Jul. 29, 1988, pp. 515-521, vol. 154, No. 2.

Thomas Ruckle, et al., *Pseudo-Prolines in Cyclic Peptides: Conformational Stabilisation of cyclo[Pro-Thr(PSI<Me, Me>pro)-Pro]*, Tetrahedron, 1999, pp. 11281-11288, vol. 55, No. 37.

Paolo Botti, et al., *Cyclic Peptides from Linear Unprotected Peptide Precursors through Thiazolidine Formation*, Journal of American Chemical Society, 1996, pp. 10018-10024, vol. 118, No. 42.

Lianshan Zhang, et al., Synthesis and Application of Unprotected Cyclic Peptides as Building Blocks for Peptide Dendrimers, Journal of American Chemical Society, 1997, pp. 2363-2370, vol. 119, No. 10.

Lianshan Zhang, et al., Lactone and Lactam Library Synthesis by Silver Ion-Assisted Orthogonal Cyclization of Unprotected Peptides, Journal of American Chemical Society, 1999, pp. 3311-3320, vol. 121, No. 14.

Yang Shao, et al., A Novel Method to Synthesize Cyslic Peptides, Tetrahedron Letters, 1998, pp. 3911-3914, vol. 39, No. 23.

* cited by examiner

SYNTHESIS OF CYCLIC PEPTIDES

The present application is a nationalization of International Patent Application PCT/AU99/00813, filed Sep. 24, 1999, which claims priority to Australian Patent Application PP 6164, filed Sep. 25, 1998.

FIELD OF THE INVENTION

This invention relates to methods for preparing cyclic peptides and peptidomimetics in solution and bound to solid supports, and to cyclic peptide or peptidomimetic libraries for use in drug screening programmes. In particular, the invention relates to a generic strategy for synthesis of cyclic peptides or peptidomimetics that enables the efficient synthesis under mild conditions of a wide variety of desired compounds.

BACKGROUND OF THE INVENTION

Although the development of recombinant DNA technology and the identification and isolation of proteins mediating a wide variety of biological activities has enabled the development of new drug therapies, proteins in general suffer from the disadvantage of susceptibility to breakdown by digestive and other enzymes. This means not only that these agents usually have to be administered by injection, but that they also have a short half-life in the body.

The biological activities of a protein rely on the three-dimensional structure of the protein molecule, which results predominantly from a balance between a variety of different non-covalent interactions. In an attempt to improve the stability and acceptability of protein pharmaceuticals, both relatively short peptide sequences encompassing the active site of the protein and synthetic molecules which adopt a three-dimensional structure resembling the active site have been extensively investigated. Structurally-constrained peptides in which a framework is maintained by disulphide bonds as well as by non-covalent interactions, and cyclic peptide or peptidomimetic systems in which the cyclisation provides the structural constraint, provide two particularly attractive approaches to stabilisation of these molecules.

Cyclic peptides show a wide variety of potent biological activities. They have been extensively explored in the drug development process as a means of introducing conformational constraints for the evaluation of the structural, conformational and dynamic properties that are critical to biological activity. Some cyclic peptides are useful as drugs in their own right. Others have been engineered to provide a multitude of functions, including novel biological properties, platforms for the development of protein mimetics, nanotechnology, specific metal coordination sites, and catalysts, to name a few.

Cyclisation may be accomplished by disulfide bond formation between two side chain functional groups, amide or ester bond formation between one side chain functional group and the backbone α-amino or carboxyl function, amide or ester bond formation between two side chain functional groups, or amide bond formation between the backbone α-amino and carboxyl functions.

The potential utility of this class of compound in any application is hindered by difficulties in synthesising the compounds. Whilst the synthesis of the linear precursors generally proceeds in high yield and purity, the final cyclisation reaction can be troublesome, resulting in low yields and/or impure products. This is particularly so for cyclic peptides of fewer than seven amino acid residues, with synthesis of cyclic tetrapeptides resulting in little or no cyclic material.

These cyclisation reactions have been traditionally carried out at high dilution in solution. With the advent of orthogonal protection strategies and new resins for solid phase peptide synthesis, cyclisation has been accomplished while the peptide is attached to the resin. One of the most common ways of synthesising cyclic peptides on a solid support is by attaching the side chain of an amino acid to the resin. Using appropriate orthogonal protection strategies, the C- and N-termini can be selectively deprotected and cyclised on the resin after chain assembly. This strategy is widely used, and is compatible with either tert-butyloxycarbonyl (Boc) or 9-fluorenylmethoxy-carbonyl (Fmoc) protocols. However, it is restricted to peptides that contain appropriate side chain functionality to attach to the solid support. It is therefore not amenable to the combinatorial synthesis of arrays of cyclic peptides.

A number of approaches have been used in an attempt to achieve efficient synthesis of cyclic peptides.

Linkers a) Activated Linkers

One procedure for synthesising cyclic peptides is based on cyclisation with simultaneous cleavage from the resin. After an appropriate peptide sequence is assembled by solid phase synthesis on the resin or a linear sequence is appended to resin, the deprotected amino group can react mildly with its anchoring active linkage to produce protected cyclic peptides, as shown schematically in Scheme 1.

Scheme 1

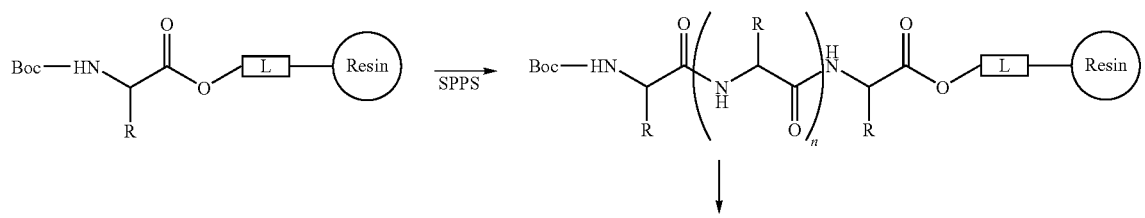

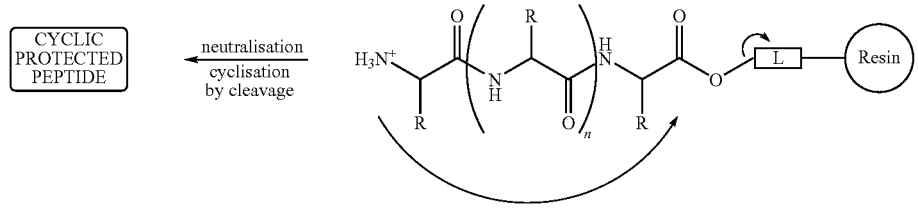

Solid Phase Cyclic Peptide Synthesis with Activated Linkers

Various linkers that have been used for the synthesis of cyclic peptides, or are amenable to their synthesis, are shown in Table 1.

TABLE 1

Examples of Activated Linkers Amendable
to Solid Phase Cyclic Peptide Synthesis

| Linker | Reference |
|---|---|
|  | Fridkin et al, 1965; Fridkin et al, 1968 |
|  | Osapay and Taylor, 1990; Osapay et al, 1990 |
|  | Rivaille et ali, 1980 |

TABLE 1-continued

Examples of Activated Linkers Amendable
to Solid Phase Cyclic Peptide Synthesis

| Linker | Reference |
|---|---|
|  | Richter et al, 1994 |
|  | Fridkin et al, 1972; Laufer et al, 1968. |

R = Peptide,

◉ = support

These cleavage-by-cyclisation strategies produce protected cyclic peptides, necessitating a final deprotection step to synthesise the target cyclic material. The cyclisation reaction is generally slow and low in yield, because extended conformational preference of the linear analogue impedes the final cyclisation reaction.

b) Safety Catch Linkers

Extensions of these concepts include supports that can be selectively modified at the end of the assembly to increase the lability of the linker. These linkers are stable during peptide assembly, and are selectively activated, leading to cyclisation and cleavage from the resin. In general, a final deprotection step is required to yield the target cyclic peptide. Examples of linkers that can be used for this approach are shown in Table 2.

TABLE 2

Examples of Safety Catch Linkers for Solid Phase Peptide Synthesis

| Safety Catch | Reagent | Activated Linker | Ref. |
|---|---|---|---|
| [structure] | H₂O₂ | [structure] | Flanigan and Marshall, 1970 |
| [structure] | mcPBA/Dioxane | [structure] | Marshall and Liener, 1970 |
| [structure] | H₂O₂ | [structure] | Flanigan, 1971 |
| [structure] | HBr | [structure] | Flanigan, 1971 |
| [structure] | CH₂N₂ | [structure] | Kenner et al, 1971 |
| [structure] | ICH₂CN | [structure] | Backes et al, 1996 |
| [structure] | CH₂N₂ | [structure] | Backes and Eliman, 1994 |

These strategies are again limited by the conformational preferences of the linear precursor.

c) Backbone Linkers

A simple extension of the concept of attaching the side chain to resin to achieve C— to N-cyclisation is the attachment of the backbone N to resin. Recently Jensen et al (1996) reported a backbone linker that has been used for synthesising linear peptides, diketopiperazines, peptide aldehydes and cyclic peptides (Jensen et al, 1998). There are several limitations to this process, these include difficulties in acylating the secondary amine to form the 'linked' amide bond and the fact that standard Fmoc SPPS leads to almost complete diketopiperazine formation at the dipeptide stage. Special protection strategies need to be employed to avoid this problem.

Scheme 2

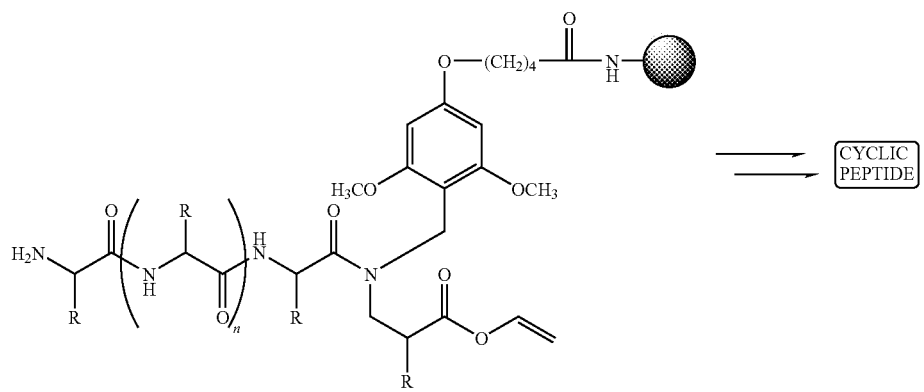

Backbone Linkers for Solid Phase Peptide Synthesis

Intraresin Chain Transfer

Another approach for synthesising cyclic peptides involves the attachment of a linker that contains two peptide attachment points to the resin, one of which is temporarily masked. Using standard solid phase techniques, the linear precursor is assembled on resin. The X and Y functionalities (Scheme 3) are then selectively unmasked and cyclised. Cleavage at the linker liberates the free C-terminal carboxylic acid group while the peptide is still attached to the resin. C- and N-cyclisation is then achieved by standard activation conditions, yielding cyclic peptides.

Preorganising Peptides for Cyclisation a) Reversible N-Substitution

The formation of a peptide ring, like any other cyclisation reaction, requires the generation of mutually reactive chain ends, and the reaction of these ends under conditions favouring intramolecular processes. The ease of formation of the ring is related to the conformational stability of the ring and to the losses of internal degrees of freedom that occur upon ring formation. Consequently the presence of turn-inducing amino acids such as Gly, Pro or a D-amino acid enhances the conformational stability of the ring and improves cyclisation yields. For linear peptides that do not contain amino acid Scheme 3

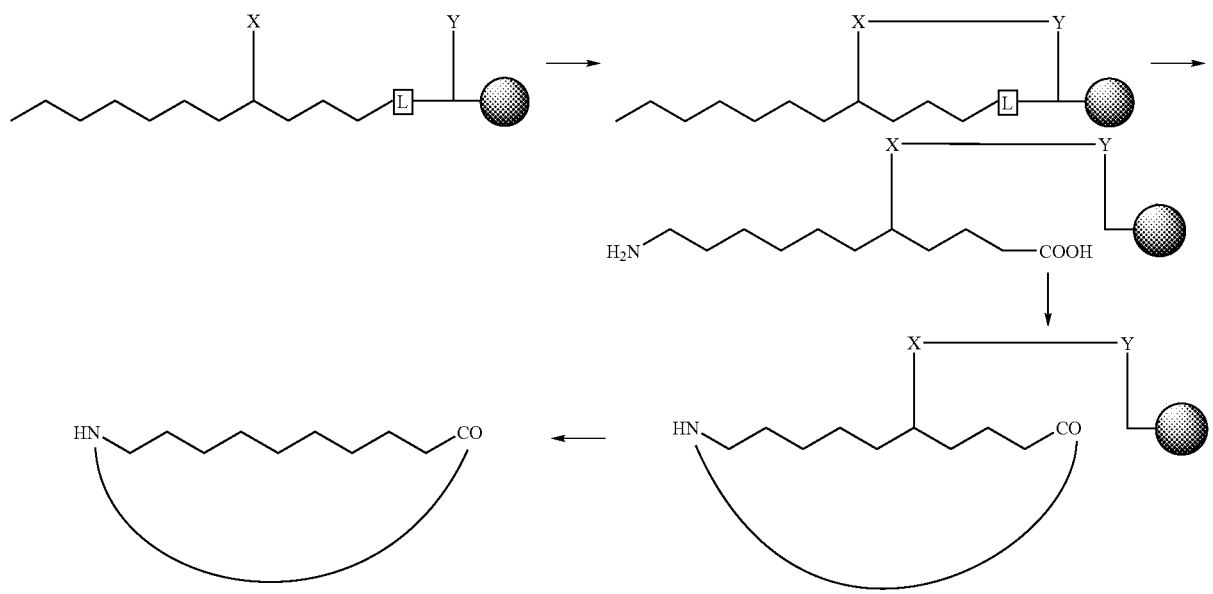

Linker Combination for Solid Phase Peptide Synthesis

This method is somewhat limited by the incorporation of the appropriate functionality X into a peptide sequence, and the complex deprotection strategies required. Once again, due to the extended nature of the linear precursors, cyclisation yields would be low.

residues that stabilise turn structures, the cyclisation reaction is likely to be an inherently improbable or slow process, due to the preference for extended conformations resulting in large strain upon ring formation.

This has led to the utilisation of various reversible chemical modifications of the peptide main chain, to enhance the cis amide bond conformation and hence reduce ring strain upon cyclisation, and to improve cyclisation yields. In the synthesis of cyclo-[Phe Phe Phe Phe] (SEQ ID NO:61), each amide N was substituted with a Boc (Cavelier-Frontin et al, 1993). In this instance the cyclisation yield increased from less than 1% to 27%. Similarly, the use of the N-(2-hydroxy-4-methoxybenzyl) (HMB) group as a reversible N-substituent has resulted in similar increases in yields of cyclic peptides (Ehrlich et al, 1996; Ehrlich et al, 1996), although no systematic study has been undertaken to quantify these effects. From the point of view of constructing peptide libraries it is impracticable to substitute every amide N of the linear precursor.

b) Ring Contraction

Ring contraction chemistry can be used for initial formation of larger flexible rings where the desired C- and N-termini are appropriately positioned to "snap shut" in a ring contraction reaction to yield the target cyclic peptide after deprotection. Ring contraction for the synthesis of cyclic peptides by intramolecular thiazolidine formation from linear unprotected peptide precursors (Scheme 4) has recently been reported (Botti et al, 1996). This procedure has the disadvantage of incorporation of the thiazolidine ring, and an additional stereo centre, into every sequence, and is not a generic procedure suitable for a combinatorial library approach.

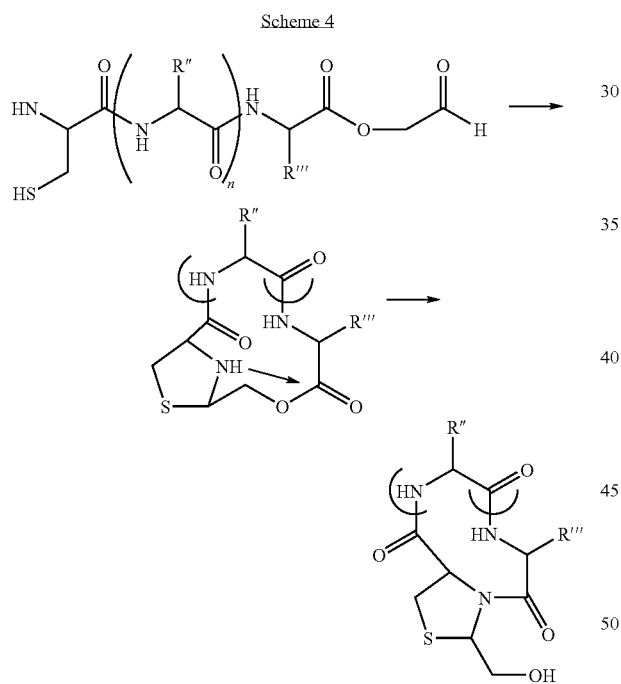

Scheme 4

Ring Contraction Chemistry for Synthesis of Cyclic Peptides

Several other research groups have also utilised ring contraction approaches for the synthesis of cyclic peptides (Camamero and Muir, 1997; Shao et al, 1998). These procedures either require the presence of a Cys or are restricted to cyclisation of peptides containing Gly at one of the termini, and are therefore not suitable for library development.

There is therefore a great need in the art for a mild, efficient, versatile synthetic strategy for the synthesis of cyclic peptides. We have now found that by introducing substituents or other moieties which preorganise peptides for cyclisation, cyclic peptides can be efficiently synthesized under mild conditions both in solution and on resin. These moieties, which we have termed peptide cyclisation auxiliaries, result in increased yields and purity of cyclic peptides. We have examined two approaches:

1. Positioning reversible N-amide substituents in the sequence.
2. Applying native ligation chemistry in an intramolecular sense.

We have evaluated these for their improvements in the solution and solid phase synthesis of small cyclic peptides.

We have systematically investigated the effects of preorganising peptides prior to cyclisation, and have developed new linkers to aid cyclic peptide synthesis. We have found surprising improvements in both yields and purity of products compared to the prior art methods. The combination of these technologies provides a powerful generic approach for the solution and solid phase synthesis of small cyclic peptides.

We have also developed linkers, and peptide cyclisation auxiliaries to aid cyclic peptide synthesis.

The ring contraction and N-amide substitution technology of the invention used in conjunction with the activated, safety catch, and backbone linker strategies of the invention provide improved methods for the solid-phase synthesis of cyclic peptides.

SUMMARY OF THE INVENTION

A feature of this invention is the combination of inducing flexibility in the peptide backbone, through reversible or irreversible N-substitution or forcing cis amide bond conformations via cis-amide bond surrogates, with novel ring contraction chemistry to preorganise peptides and facilitate the cyclisation reaction in solution. Another feature of the invention is the option of combining one or more of these preorganising technologies with novel linkers which provide attachment between peptide and resin, to provide a solid phase strategy for the mild, efficient synthesis of cyclic peptides or cyclic peptide libraries.

In its most preferred general aspect, this invention provides solution and solid-phase methods for the preparation of a cyclic peptide of the structure:

General Formula I

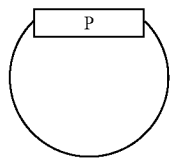

where

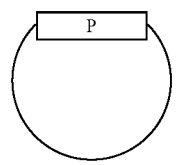

is a cyclic peptide or peptidomimetic, in which the representation of the structure follows standard conventions with the C-terminus on the right hand side of P. It comprises between 1 to 15 monomers, preferably 1 to 10 monomers, more preferably 1 to 5 monomers. This may be a monocycle, bicycle or higher order cycle, and may comprise protected or unprotected monomers.

Another general aspect of the invention provides solid-phase methods for the synthesis of cyclic peptides or peptidomimetics of the structure:

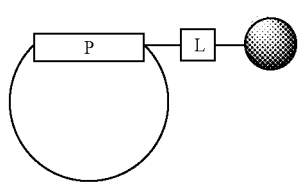

General Formula II where L is a linker unit, linking the cyclic peptide to the solid support

The linker L may be attached to any atom of the peptide, but is preferably attached to a backbone nitrogen or to an atom in the side chain of the monomer.

Thus, in a first aspect the invention provides a method of synthesis of cyclic peptides or cyclic peptidomimetic compounds, comprising the steps of:

a) inducing flexibility in the peptide or peptidomimetic compound by reversible N-substitution or by forcing a cis amide bond conformation using a cis-amide bond surrogate to facilitate cyclisation, and b) subjecting the cyclic peptide or peptidomimetic compound to a ring contraction reaction. This ring contraction reaction may occur spontaneously, so that a separate reaction may not be required.

The method is applicable to both solution phase and solid phase synthesis.

In a preferred embodiment, this aspect of the invention provides a method for solution phase synthesis of a cyclic peptide of General Formula I, comprising the steps of:

a) Preparing a linear peptide of General Formula III

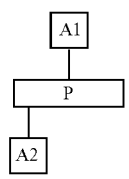

General Formula III where P is a linear peptide of 10 to 15 monomers, preferably 1 to 10 monomers, most preferably 1 to 5 monomers.

A1 is one or more N-substituents, either reversible or non-reversible, on the peptide backbone, or is a chemical moiety that forces a cis conformation of the backbone, and A2 is a covalently-bonded group of atoms comprising a reactive functionality to form an initial large cyclic peptide prior to ring contraction to the desired substituted cyclic peptide;

b) Activating the C-terminus to form a cyclic peptide of General Formula IV:

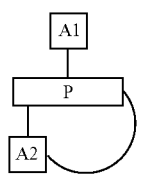

General Formula IV c) Permitting the peptide of General Formula IV to rearrange via a ring contraction reaction (which may occur spontaneously) to form a cyclic peptide of General Formula V; and optionally

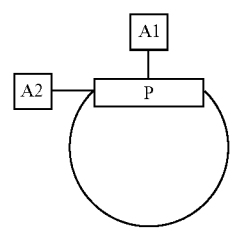

General Formula V d) Subjecting the cyclic peptide of General Formula V to a deprotection reaction to remove the groups A1 and A2 to yield the desired cyclic peptide of General Formula I.

Optionally one or more of the groups A1 or A2 may be left attached to the peptide to provide a suitable point for attaching to a solid support, for derivatising with additional chemical functionality to improve library diversity, or for dimerisation or oligomerisation with other cyclic peptides or molecules, as illustrated below.

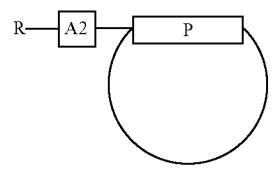

R=solid support or other chemical moiety

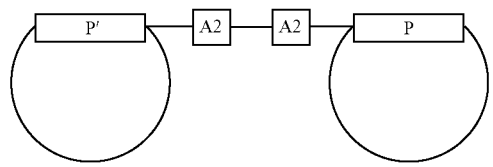

Alternatively ring contraction may lead to spontaneous elimination of A2.

Preferably A1 is a reversible N-substituent, such as 2-hydroxy-4-methoxybenzyl, 2-hydroxybenzyl or 2-hydroxy-6-nitrobenzyl substituents.

Preferably A2 comprises a nucleophile (eg. thiol or hydroxyl) that reacts rapidly with a C-terminus to form an initial large ring, which then contracts either spontaneously, or upon heating or additional chemical treatment (eg. addition of metal ions). A2 may be an irreversible substituent, may be removed after ring contraction, or may eliminate spontaneously, upon ring contraction. A2 also provides access to an additional site for substitution to increase library diversity. A2 may also be any of the compounds of General Formula I described in our co-pending U.S. application Ser. No. 09/787,840 filed Jul. 6, 2001, which is a nationalization of PCT application No. PCT/AU99/00812 corresponding to Australian provisional patent application No. PP6165 filed on 25 Sep. 1998, the same day as this the Australian priority application for the present application, entitled "Auxiliaries for Amide Bond Formation". Specific examples of these auxiliaries are exemplified herein.

In a second aspect, the invention provides a method of solid phase synthesis of cyclic peptides, comprising the steps of:

a) synthesis of a linear peptide of General Formula VI, bound to a solid support via a linker L, General Formula VI

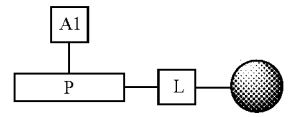

where A1 and P are as defined above and L is a linker between any atom of the peptide and the solid support, and (b) either (i) subjecting the peptide (comprising either protected or unprotected monomers) to cyclisation and concomitant cleavage from the solid support to yield a cyclic peptide of General Formula VII, General Formula VII

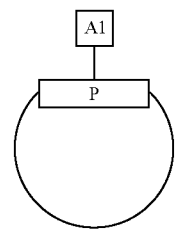

followed by selective removal or derivatisation of A1 as described above, if necessary followed by side chain deprotection of the peptide and removal of A1 to yield the desired cyclic peptide of General Formula I; or (ii) cyclisation of the peptide to yield a second solid support-bound cyclic peptide of General Formula VIII, General Formula VIII

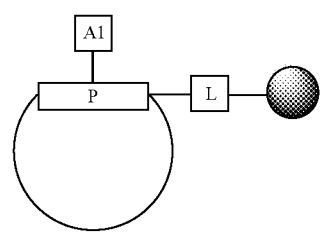

The person skilled in the art will appreciate that side chain deprotection of the peptide, removal of A1 and cleavage from the solid support may be performed separately or concurrently. Removal of peptide protecting groups, A1 and cleavage from the solid support will yield the desired cyclic peptide of General Formula I.

Alternatively both a linker unit and A2 as described above are used.

Thus in another preferred embodiment, the invention provides a method of solid-phase synthesis of a cyclic peptide, comprising the steps of:

a) preparing a linear solid support-bound peptide of General Formula IX:

General Formula IX

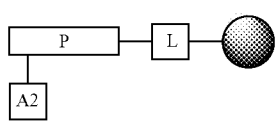

in which A2, P and L are as defined above;

b) subjecting the peptide of General Formula IX to cyclisation and concomitant cleavage from the solid support to yield a cyclic peptide of General Formula X;

General Formula X

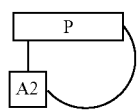

c) allowing the cyclic peptide X to undergo ring contraction (which may occur spontaneously) to yield a second cyclic peptide of General Formula XI, and General Formula XI

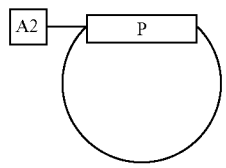

d) either derivatising the group A2, or removing A2 to yield the desired cyclic peptide of General Formula I.

In another alternative the linear solid support-bound peptide of General Formula IX may be subjected to initial cyclisation and ring contraction on the solid support to yield a solid support-bound cyclic peptide of General Formula XII, General Formula XII

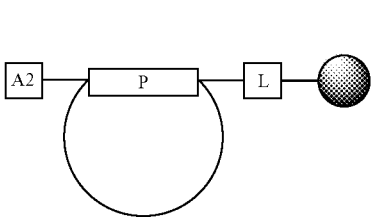

and either (i) cleaved from the solid support to yield an A2-substituted cyclic peptide, or (ii) deprotected and cleaved from the solid support to yield a cyclic peptide of General Formula I.

Alternatively, the group A2 may be derivatised either in solid phase or in solution.

Again it will be appreciated that peptide deprotection, removal of A2 and cleavage from the solid support may be performed separately or concurrently.

Most preferably the method of the invention utilises all three of (i) N-substituents, (ii) a covalently-bonded group of atoms which forms an initial large ring which subsequently contracts, and (iii) synthesis on a solid support.

Therefore in a third aspect, the invention provides a method of solid phase synthesis of a cyclic peptide, comprising the steps of a) synthesis of a linear solid support-bound peptide of General Formula XIII, General Formula XIII

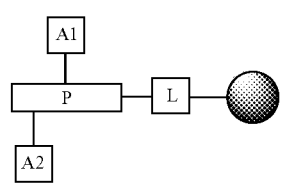

where A1, A2, P and L are as defined above;

b) subjecting the peptide of General Formula XIII to cyclisation and concomitant cleavage from the solid support to yield a cyclic peptide of General Formula XIV, General Formula XIV

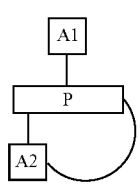

c) subjecting the cyclic peptide of General Formula XIV to ring contraction (which may be spontaneous), and d) cleaving the groups A1 and A2 to yield the desired cyclic peptide of General Formula I.

Alternatively this aspect of the invention provides a method of solid phase synthesis of cyclic peptides, comprising the steps of;

a) synthesis of a linear solid support-bound peptide of General Formula XIII, b) subjecting the linear peptide to cyclisation on the solid support to yield a cyclic peptide of General Formula XV, General Formula XV

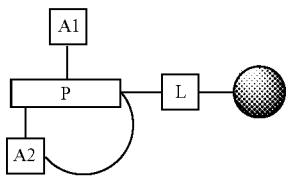

c) subjecting the cyclic peptide to ring contraction (which may occur spontaneously) to yield a cyclic peptide of General Formula XVI, General Formula XVI

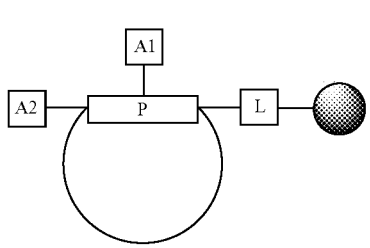

and either d) cleaving groups A1 and A2 while the peptide is bound to the solid support to yield a solid support-bound cyclic peptide of General Formula II, or General Formula II

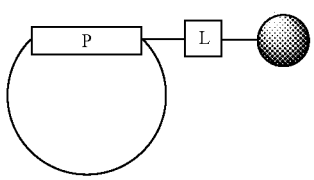

e) subjecting the cyclic peptide to deprotection and concomitant cleavage from the solid support to yield the desired cyclic peptide of General Formula I.

Once again it will be appreciated that peptide deprotection, removal of A2 and cleavage from the solid support may be performed separately or concurrently.

For the purposes of this specification, the term "monomer" includes compounds which have an amino and carboxy terminus separated in a 1,2, 1,3, 1,4 or larger substitution pattern. This includes the 20 naturally-occurring α-amino acids in either the L or D configuration, the biosynthetically-available amino acids not usually found in proteins, such as 4-hydroxy-proline, 5-hydroxylysine, citrulline and ornithine; synthetically-derived α-amino acids, such as α-methylalanine, norleucine, norvaline, Cα- and N-alkylated amino acids, homocysteine, and homoserine; and many others as known to the art. It also includes compounds that have an amine and carboxyl functional group separated in a 1,3 or larger substitution pattern, such as—β-alanine, γ-amino butyric acid, Freidinger lactam (Freidinger et al, 1982), the bicyclic dipeptide (BTD) (Freidinger et al, 1982; Nagai and Sato, 1985), aminomethyl benzoic acid (Smythe and von Itzstein, 1994), and others well known to the art. Statine-like isosteres, hydroxyethylene isosteres, reduced amide bond isosteres, thioamide isosteres, urea isosteres, carbamate isosteres, thioether isosteres, vinyl isosteres and other amide bond isosteres known to the art are also useful for the purposes of the invention. Thus the word "peptide" as used herein encompasses peptidomimetic compounds. Optionally the peptide may be protected with one or more protecting groups of the type used in the art (see for example Bodanszky, M., (1984), "*Principles of Peptide Synthesis*", Springer-Verlag, Heidelberg).

A peptide is comprised of between one and fifteen monomers, preferably between one and ten monomers, more preferably one to five monomers.

The solid support may be of any type used for solid phase synthesis of peptides, peptidomimetics, oligonucleotides, oligosacharides or organic molecules. The solid support may be in the form of a bead, a pin or another such surface which is suitable for use in solid phase synthesis. A wide variety of suitable support materials are known in the art. See for example Meldal, M., Methods in Enzymology, 1997 289 83-104. Commercially-available polystyrene supports, including aminomethyl-polystyrene, benzhydrylaminepolystyrene, polyethyleneglycol-polystyrene are especially suitable.

A "linker" means any covalently-bonded group of atoms which connects an atom or molecular fragment to another via covalent bonds. See for example Songster, M. F., Barany. G., Methods in Enzymology, 1997 289 126-175. Typically the linker will comprise an optionally substituted allyl, aryl, alkylene group containing functionality, such as an ether, ester, amide, sulfonamide, sulfide, or sulfoxide functionality, within the linker. Such a functionality will normally be used to create the connection between the two groups, or to separate the groups.

A "cis amide bond surrogate" is a chemical group, such as a tetrazole (Marshall et al, 1981), which forces a cis conformation.

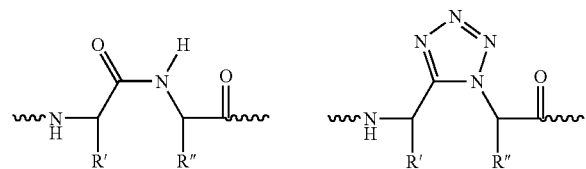

For the purposes of this specification it will be clearly understood that the word "comprising" means "including but not limited to", and that the word "comprises" has a corresponding meaning.

Coupling methods to form peptide bonds are well known to the art. See for example Albericio and Carpino, 1997. When synthesising cyclic peptides in solution or upon a side chain or backbone attachment, the choice of activation can affect the yields and purity of cyclic material. For slow cyclisations the increased lifetime of the intermediate activated linear peptide provides an opportunity for increased epimerisation at the C-terminal residue. The extent of epimerisation may be diminished by application of the azide method (Izumiya et al, 1981) or its modification using DPPA (Brady et al, 1983). However, these methods are extremely slow, usually requiring many hours or even several days (Izumiya et al, 1981; Schmidt and Neubert, 1991; Heavner et al, 1991). In comparison with DPPA, TBTU (Knorr et al, 1989) and BOP (Castro et al, 1975) provide fast cyclisation, but may lead to C-terminal epimerisation. The HOAt coupling reagents have recently been reported significantly to improve head-to-tail cyclisation of penta- and hexa-peptides with reduced epimerisation rates (Ehrlich et al, 1996).

DETAILED DESCRIPTION OF THE INVENTION

Figure 1:
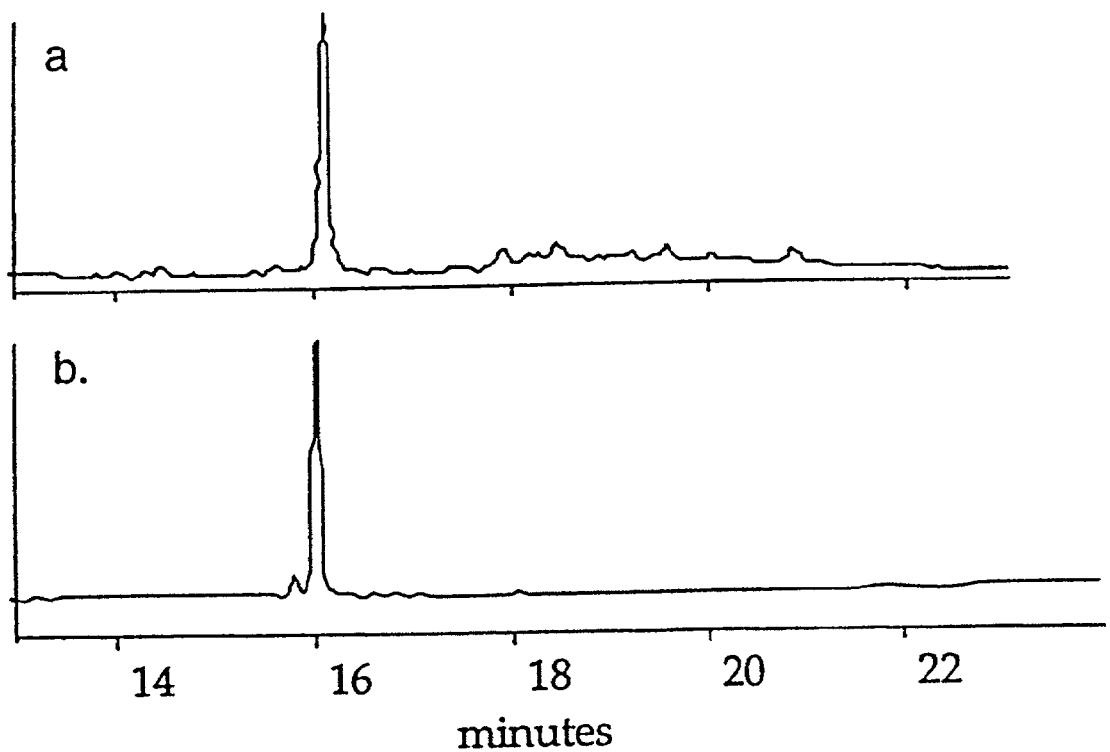
FIG. 1 shows HPLC elution profiles of the crude product of solid phase synthesis of cyclo-D-G-(Cat)-R-G (SEQ ID NO:1) following cyclisation and concomitant cleavage from the resin (Profile A) and HPLC-purified cyclo-D-G-(Cat)-R-G (SEQ ID NO:1) synthesised in solution phase (Profile B). Cat is 3-carboxy-4-aminothiophene, which is alternatively known as Act (3-amino-4-carboxythiophene).

The invention will now be described in detail by way of reference only to the following non-limiting examples, and to the figures.

Abbreviations used herein are as follows:

| | |
|---|---|
| DIEA | Diisopropylethylamine |
| DMF | dimethylformamide |
| DMSO | dimethylsulphoxide |
| DPPA | diphenylphosphoryl azide |
| BOP | benzotrizo-1-yloxy-tris(dimethylamino) phosphonium hexaflurophosphate |
| HOAt | 7-aza-1-hydroxybenzotriazole |
| HBTU | O-benzotriazole-N,N,N',N'-tetramethyluronium hexafluorophosphate |
| HMB | 2-hydroxy-4-methoxybenzyl |
| HPLC | high performance liquid chromatography |
| ISMS | ion spray mass spectrometry |
| LC-MS | liquid chromatography-mass spectrometry |
| NMR | Nuclear Magnetic Resonance |
| ROESY | rotating frame Overhauser enhancement spectroscopy |
| r.t. | room temperature |
| TOCSY | total correlated spectroscopy. |

EXPERIMENTAL

General Methods

Melting Points were determined on a Gallenkamp m.p. apparatus and are uncorrected. Solvent evaporation were carried out using a Büchi rotary evaporator. Deionised water was used throughout, and was prepared by a Milli-Q water purification system (Millipore-Waters). Screw-cap glass peptide synthesis reaction vessels (20 mL) with sintered glass filter frit were obtained from Embell Scientific Glassware (Queensland, Australia). An all-Kel-F apparatus (Peptide Institute) was used for HF cleavage. Argon, helium and nitrogen (all ultrapure grade) were from BOC gases (Queensland, Australia)

$^1$H NMR spectra were recorded on a Varian Gemini 300 spectrometer at 300 MHz, and chemical shifts are reported in δ parts per million down field from tetramethylsilane. Coupling constants (J) refer to vicinal proton-proton coupling. $^{13}$C NMR spectra were also recorded on a Varian Gemini spectrometer at 75.5 MHz. TOCSY and ROESY spectra were performed on a Büchi ARX 500 spectrometer.

Mass spectra were acquired on a PE-Sciex API-III triple quadrupole mass spectrometer equipped with an Ionspray atmospheric pressure ionization source. Samples (10 mL) were injected into a moving solvent (30 mL/min; 50/50 CH$_3$CN/0.05% TFA) coupled directly to the ionisation source via a fused silica capillary interface (50 mm i.d.×50 cm length). Sample droplets were ionized at a positive potential of 5 kV and entered the analyser through an interface plate and subsequently through an orifice (100-120 mm diameter) at a potential of 80 V. Full scan mass spectra were acquired over the mass range of 200 to 1000 daltons with a scan step size of 0.1 Da. Molecular masses were derived from the observed m/z values using the MacSpec 3.3 and Biomultiview 1.2 software packages (PE-Sciex Toronto, Canada).

Thin layer chromatography (Tlc) was performed on silica gel 60 F$_{254}$ plates (Merck Art 5735). The chromatograms were viewed under u.v. light and/or developed with iodine vapour. Preparative column chromatography was effected under pressure, using for normal phase Merck Kieselgel 60 (Merck Art 7734). Analytical reverse phase HPLC were run using a C-18 Vydac column (218TP52022), while Semi-Preparative reverse phase HPLC was carried out using a C-18 Vydac column (218TP52022). Both columns were attached to a Waters HPLC apparatus fitted with a Holochrome U.V. detector. Measurements were carried out at either λ=214 nM or 254 nM. Chromatographic separations were achieved using linear gradients of buffer B in A (A=0.1% aqueous TFA; B=90% CH3CN, 10% H2O, 0.09% TFA) at a flow rate of 0.25 mL/min (microbore), 1 mL/min (analytical) and 8 mL/min (preparative)

Materials

Boc-L-amino acids, Fmoc-L-aminoacids, Boc-Val-Polyaminomethylstyrene Resin, Merrifield resin, Boc-Gly-PAM Resin, synthesis grade dimethylformamide (DMF), trifluoroacetic acid (TFA) and diisopropylethylamine (DIEA) were purchased from Auspep (Parkville, Australia) or Novabiochem (Alexandria, Australia) Chlorotrityl Resin was purchased from Pepchem (Tubingen, Germany). HBTU and BOP were purchased from Richelieu Biotechnologies (Montreal, Canada). Tris (2-carboxyethyl)phosphine hydrochloride salt (TCEP) was purchased from Strem Chemicals Inc. Newburyport Mass. AR grade EtOAc, MeOH, CH$_2$Cl$_2$, CHCl$_3$, hexane, acetone and HPLC grade CH$_3$CN were all obtained from Laboratory Supply (Australia), HF was purchased from CIG (Australia). All other reagents were AR grade or better, and were obtained from Aldrich or Fluka.

EXAMPLE 1

Peptide Cyclisation Auxiliaries

Backbone Substitution

N-substitution has the potential to alter the cis-trans equilibrium favouring more cis conformations and enhancing cyclisation yields:

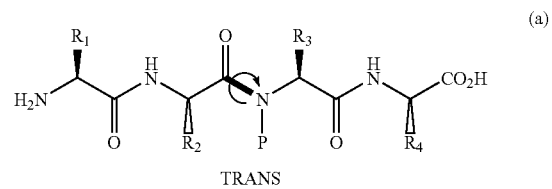

(a)

TRANS

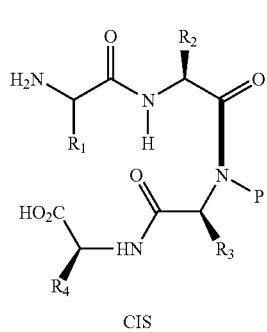

(b)

CIS

We have examined the effect of the number and position of N-methylations on cyclisation yield of tetraglycine Eight linear tetrapeptides were synthesised, including all permutations of glycine and sarcosine (N-methyl glycine) at the three C-terminal residues. These are summarised in Table 3.

TABLE 3

Linear N-substituted Tetraglycines and Corresponding Yields of Cyclisation

| Linear tetrapeptide | SEQ ID NO: | Yield of cyclisation |
|---|---|---|
| Gly-Gly-Gly-Gly | 6 | <1% |
| Gly-Gly-Gly-Sar | 7 | 8% |
| Gly-Gly-Sar-Gly | 8 | 11% |
| Gly-Sar-Gly-Gly | 9 | 1% |
| Gly-Gly-Sar-Sar | 10 | 18% |
| Gly-Sar-Gly-Sar | 11 | 2% |
| Gly-Sar-Sar-Gly | 12 | 13% (16%*) |
| Gly-Sar-Sar-Sar | 13 | ~5% |

*Yield of cyclisation for the corresponding N-HMB substituted linear tetraglycine, i.e., where sarcosine is replaced by [—N(HMB)—CH$_2$—CO—].

The yield for each cyclisation was calculated from the weight of isolated product. The results of this experiment suggest that N-substitution of the N-1 or N-2 position of a tetrapeptide significantly improves yields of cyclisation whereas N-substitution at the third residue has little effect. The effect of multiple substitution at two or more N-sites appears to be more or less additive. The best cyclisation result was obtained with the N-1 and N-2 substituted precursor Gly-Gly-Sar-Sar (SEQ ID NO:10). However, from a synthetic point of view substitution at the N-1 position is less desirable, as this facilitates diketopiperazine formation at the dipeptide stage during assembly of the linear precursor. We have found that altering the position of the backbone substituent can significantly affect the ratio of monocycle over dimer or higher oligomers.

We have extended this N-substitution approach to include reversible N-substitution. Three linear precursors, the backbone unprotected peptide X (Asp(OBu)-Val-Gly-leu; SEQ ID NO:14) and two backbone HMB-substituted analogues Y (Asp(OBu)-(HMB)Val-Gly-Leu; SEQ ID NO:15) and Z (Asp(O-Bu)-Val-(HMB)-Gly-Leu; SEQ ID NO:16), were prepared.

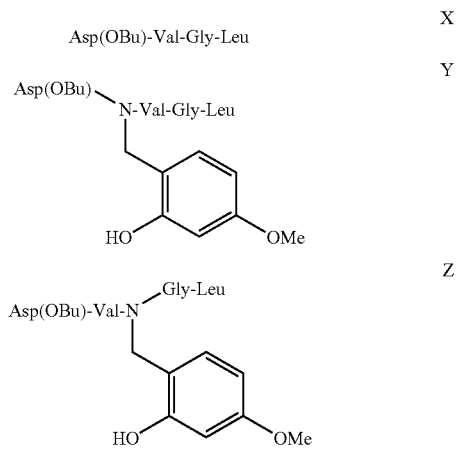

The three peptides were subjected to standard cyclisation protocols and the crude reaction mixtures analysed by HPLC and ISMS. The products (monomers and dimers) were further examined for epimerisation at the C-terminal leucine. Table 4 lists the products found and the corresponding yield of isolated material (% by weight).

TABLE 4

Yields of Isolated products from Cyclisation of Tetrapeptides X, Y and Z

|  | X | Y | Z |
|---|---|---|---|
| Linear | — | 10% | — |
| Monocycle (L-Leu) | — | 8% | 7% |
| Monocycle (D-Leu) | — | 2% | 16% |
| Dimer (L, D-Leu) | 1% | — | 8% |
| Dimer (L, L-Leu) | 17% | 19% | 15% |
| Overall % D | 3% | 5% | 43% |

As expected, the unsubstituted tetrapeptide X generates dimers, with no detectable amounts of monocycle present as assessed by ISMS. Two dimers are found in a ratio of 1/10 as assessed by HPLC. The first eluting dimer contains L-Leucine and D-Leucine in a ratio of 1/1. The second eluting dimer is formed from cyclisation of the all L-octapeptide. Considering that for cyclisation of peptide X, 0.5% D-Leu is observed and that a total yield of 18% was achieved, this equates to an overall epimerisation at the C-terminus of approximately 3% (0.5/18×100).

On the other hand, both backbone-substituted tetrapeptides Y and Z generate a significant amount of cyclic tetrapeptide (monocycle), corroborating the N-Me study described above. As for peptide X, two dimers are formed [L-Leu/D-Leu and L-Leu/L-Leu] when cyclising peptide Y. For tetrapeptide Y a total of 80% of the separated monocycle contains L-Leu, but surprisingly for tetrapeptide Z a total of 70% of the separated monocycle contains D-Leu. For peptide Y about 5% D-Leucine is found in the total separated product, and for peptide Z 43% D-Leu is found. For tetrapeptide Z, this is equivalent to almost 100% racemisation (50% D-Leu 50% L-Leu). In an attempt to minimise epimerisation of the C-terminus, cyclisation of tetrapeptide Z was performed with HATU instead of BOP. Under these conditions overall % D-leucine was halved.

Once epimerised, tetrapeptide Z cyclises more efficiently (16% D-Leu monocycle, no D-Leu/D-Leu dimer detected). Tetrapeptide Y is less reactive, as significant amounts of linear peptide are still present after three hours of activation. This may be explained by increased steric hindrance at the N-terminus.

We conclude that introduction of an HMB group on the middle amide nitrogen of the tetrapeptide X (ie. tetrapeptide Z) assists cyclisation, but significantly promotes epimerisation of the C-terminus. Substitution at the third amide nitrogen (tetrapeptide Y) assists cyclisation without increased epimerisation but reduces the reactivity of the peptide. In Example 3 below, we describe ring contraction chemistry that may help alleviate the epimerisation problems while enhancing cyclisation through N-substitution.

Experimental to Example 1

This section describes the experimental details for preorganising peptides prior to cyclisation via N-substitution.

Date in Table 3

Boc-Sar-Merrifield resin was prepared as follows: Boc-Sar-OH (380 mg, 2 mmole) was dissolved in 2 mL $H_2O$ containing $Cs_2CO_3$ (326 mg, 1 mmole). The mixture was lyophilised and residue taken up in DMF (5 mL). The solution is added to Merrifield resin (2.7 gr, 0.7 mmol/gr) and heated to 50° C. overnight. The resin is filtered, washed and dried (3.05 gr, 0.65 mmole/gr). The tetrapeptides were assembled using in situ neutralisation protocols. After assembly the peptides were cleaved using HF/p-cresol (9/1) at 0° C. for 1 hour. The HF was then evaporated and the product precipitated with cold ether (10 mL). After the ether washes (3×10 mL) the crude peptides were dissolved in water and purified by HPLC using 100% water (0.1% TFA).

Cyclisation (Table 3)

The purified peptides (0.1 mmole) were dissolved in 100 mL DMF. BOP (133 mg, 0.3 mmole) was added followed by DIEA (0.5 mmole, 87 μL). After stirring overnight, the DMF was removed in vacuo, and the residues dissolved in acetonitrile/water (1/1) containing TFA (0.1%) and loaded on a reverse phase HPLC column. The isolated products from the HPLC run (10 minutes at 100% A, then 1% gradient to 50% B) were analysed by ISMS and analytical HPLC, dried and weighed. Yields were calculated from the weight of the isolated product.

Epimerisation Studies (Table 4)

The N-substituted linear peptides were synthesised on chloro-trityl resin. The HMB-protection group was introduced via solid phase reductive alkylation of the N-terminus with 2-hydroxy-4-methoxybenzaldehyde (Ede et al, Tetrahedron Lett., 1996 37 9097). Acylation of the secondary amine was carried out by preactivating the following Fmoc-protected residue using HOAT (2Eq.) and DIC (1Eq.) for 30 min in DMF and performing the reaction at 50° C. for 12 hours. The peptide assembly was completed as described previously and linear peptide cleaved from the resin (1% TFA in DCM). All three peptides (all L-residues) were purified by reverse phase HPLC prior to cyclisation.

Cyclisation

The purified peptides (0.1 mmole) were dissolved in DMF (100 mL). BOP (133 mg, 0.3 mmole) was added, followed by DIEA (0.5 mmole, 87 μL). After 3 hours stirring the DMF was removed in vacuo, residues dissolved in acetonitrile/water (1/1) containing TFA (0.1%) and the solution loaded on a reverse phase HPLC column. The isolated products from the HPLC run (5 minutes at 80% A, then 2% gradient to 100% B) were analysed by ISMS, analytical HPLC and epimerisation of leucine determined by amino acid analysis. Yields were calculated from the weight of the isolated product and the ratio of L/D from AA-analysis.

EXAMPLE 2

Ring Contraction

Another approach to overcoming the problems in the solution and solid phase synthesis of small cyclic peptides is to utilise novel ring contraction chemistry. As previously noted, the preferred extended conformation and rigidity of amide bonds is a problem in small peptide cyclisation. By initially forming a larger, more flexible ring, through the inclusion of a flexible "linker unit", the potential for end-to-tail cyclisation is enhanced by increasing the effective concentration of the C- and N-terminus. The desired C- and N-termini are then appropriately positioned to "snap shut" in a ring contraction reaction. This is shown schematically in Scheme 5.

Scheme 5

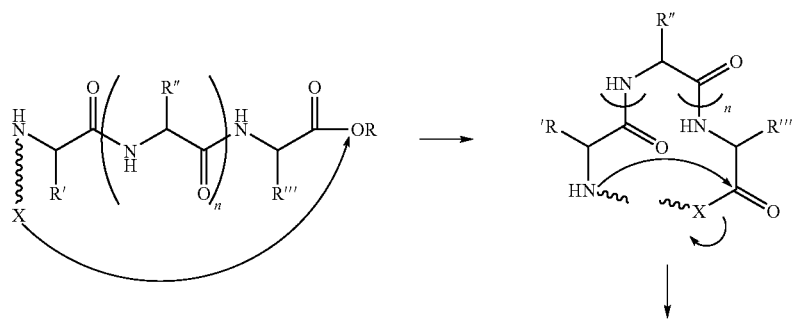

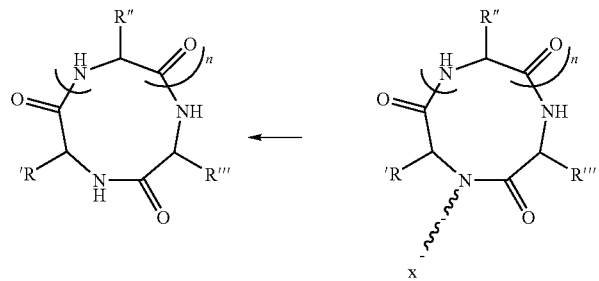

Ring Contraction Chemistry

The ring contraction auxiliaries illustrated below are evaluated for this purpose.

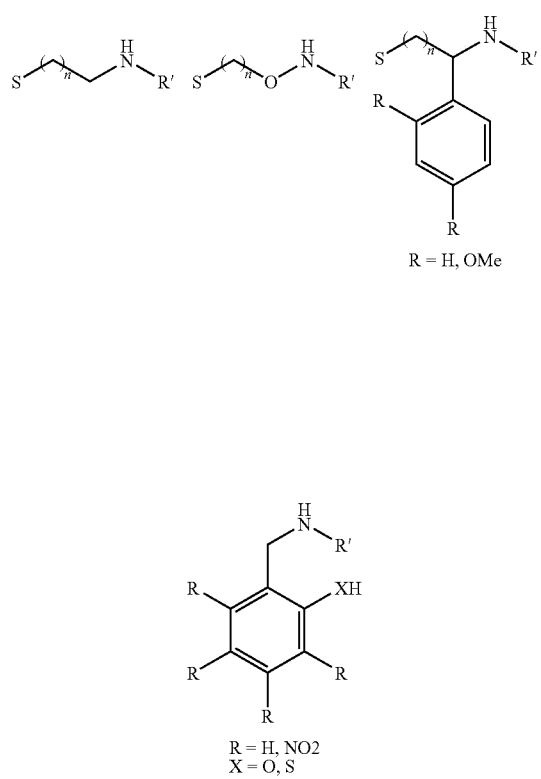

R = H, OMe

R = H, NO2
X = O, S

Examples of Ring Contraction Auxiliaries
Additional auxiliaries include:

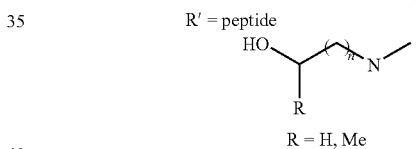

R' = peptide

R = H, Me

A Subset of Ring Contraction Auxiliaries

To examine the feasibility of the ring contraction approach, we have synthesised a number of linear pentapeptides carrying an ethane thiol group at the N-terminus. The synthesis of the linear precursors was achieved as illustrated in Scheme 6. Bromoacetic acid was coupled to the N-terminus of the resin-bound tetrapeptide using the symmetrical anhydride approach. The bromopeptide was treated with a 2M solution of cystamine in DMSO and the resulting peptide cleaved from the resin. The disulfide moiety was further reduced using TCEP in an 0.1M ammonium carbonate solution and the free sulfide purified by HPLC. The sulfide was then subjected to standard cyclisation conditions (ie $10^{-3}$ M in DMF, 3 eq. BOP, 5 eq DIEA). Presumably, the initially formed thioester spontaneously rearranges to the ethane thiol substituted cyclic peptide. The resulting product was confirmed by NMR examination and by the fact that the sulfide readily dimerises in DMF. The dimer was isolated and characterised by ISMS and NMR. Reduction of the dimer with TCEP reestablished the free sulfide-peptide in quantitative yields.

Scheme 6

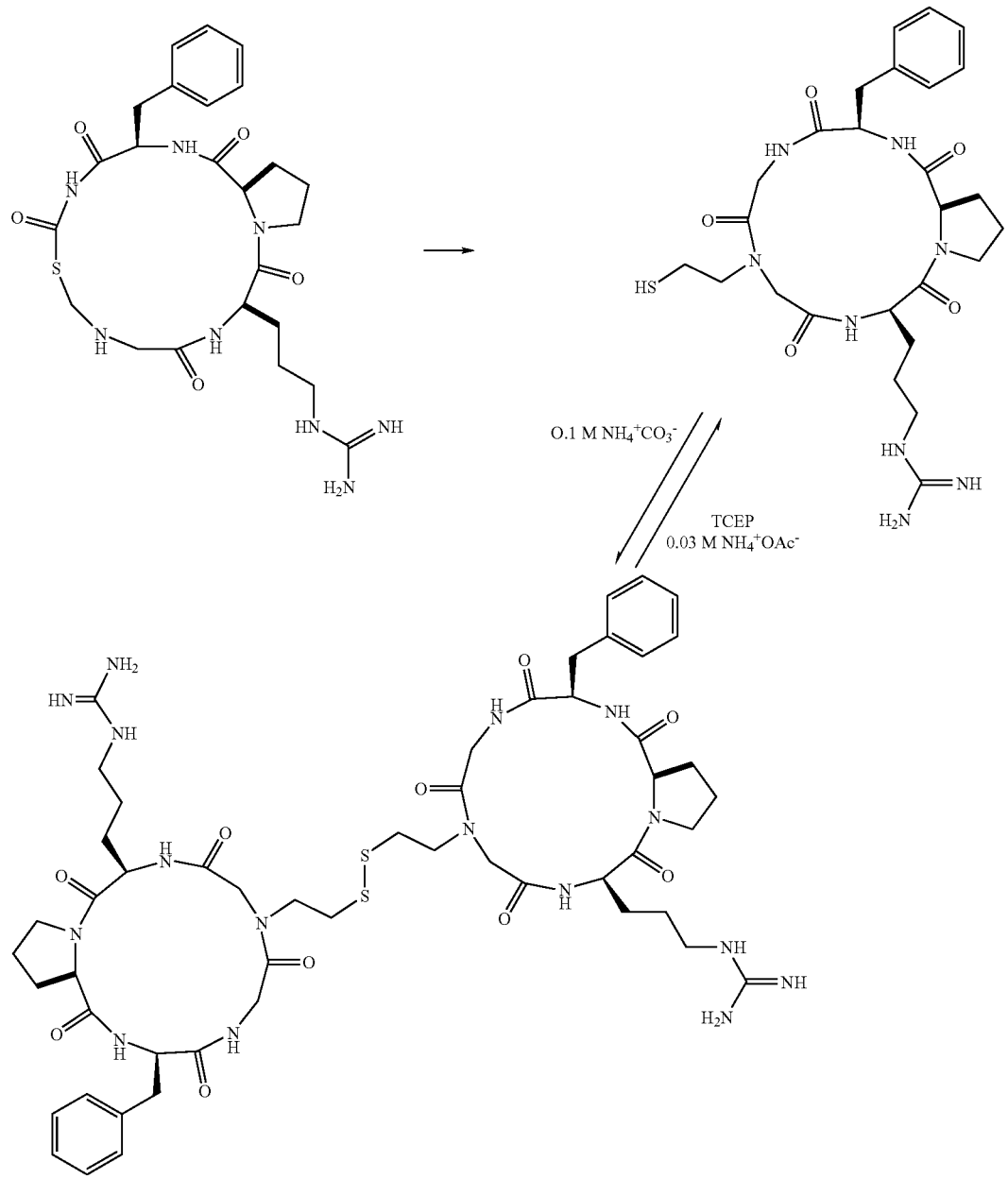

Synthesis and Cyclisation of the Linear Ethane Thiol-Substituted Precursor for Ring Contraction This process has several distinct advantages. The increased nucleophilicity of the thiol compared to the amine presumably results in rapid formation of the thioester, thereby significantly reducing the potential for epimerisation. The C- and N-termini are then appropriately positioned to snap shut in a ring contraction reaction.

In this example the ethane thiol group is irreversibly linked to the cyclic target. We have designed and tested other auxiliaries, outlined above, that allow cleavage of the auxiliary-peptide bond. The ring contraction in all the above-mentioned examples proceeds via a five or six-membered fused ring transition state.

Synthesis of a Difficult Cyclic Peptide, [cyclo[Ala-Phe-Leu-Pro-Ala] (SEQ ID NO:17):

H-Ala-Phe-Leu-Pro-Ala-OH (SEQ ID NO:18) was a recently reported example of a sequence which is difficult to cyclise (Schmidt and Langner, 1997). When subjected to cyclisation conditions, dimers and higher oligomers were generated, but no target cyclopentapeptide was formed. In the following set of experiments, summarized in Scheme 7, we demonstrate that the monocycle was accessible using a ring contraction strategy.

Cyclisation of Unsubstituted Ala-Phe-Leu-Pro-Ala.

As a control experiment we attempted to cyclise the unsubstituted linear peptide (Ala-Phe-Leu-Pro-Ala; SEQ ID NO:18) using standard cyclisation conditions (1 mM in DMF, 3 eq. BOP, 5 eq. DIEA, 3 h at rt). As expected from the previously reported results (Schmidt and Langer, 1997), only cyclic dimer and some trimer were obtained, but no target monocyclic product was isolated.

The 5-nitro-2-hydroxybenzyl auxiliary used in this and other examples was as described in our co-pending U.S. application Ser. No. 09/787,840 filed Jul. 6, 2001, which is a nationalization of PCT application No. PCT/AU99/00812, corresponding to Australian provisional application No. PP6165 filed on 25 Sep. 1998. The peptide 1a, containing the 5-nitro-2-hydroxybenzyl substituent, was synthesised and cyclised under standard conditions, yielding two monocyclic products as well as significant amounts of a side product 3a (Mr, 812 Da), caused by reaction of the phenol functionality with excess BOP in the reaction mixture (Scheme 7, A). By adjusting the amount of activating reagent and base, formation of this side product was completely avoided. The reaction conditions were further optimised by altering the temperature and amount of base after an initial cyclisation period, and monitoring the formation of monocyclic products by LC/MS analysis. The best results were obtained when after 3 h of reaction (1 mM in DMF, 1 eq BOP, 2 eq DIEA, rt) excess DIEA (10 eq) was added and the mixture left standing for 24 h or heated to 65° C. for 1 hour.

Figure 3:
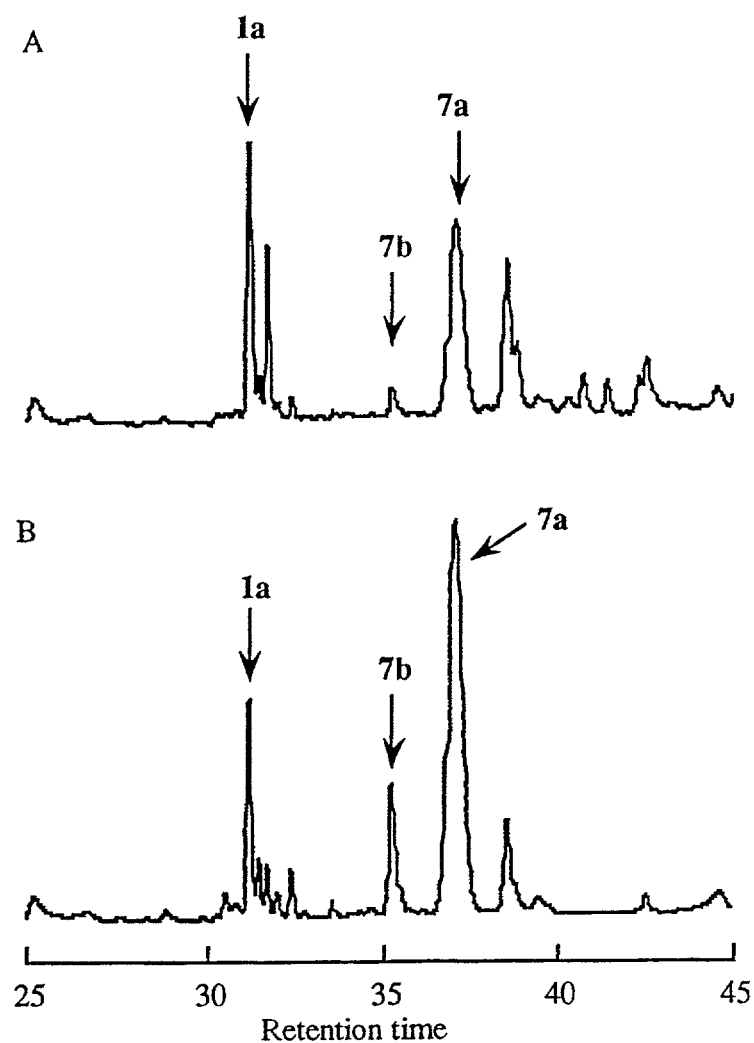
FIG. 3 shows the results of HPLC analysis of cyclisation of linear peptide 1a A) after 3 h at rt, and B) 1 h heating to 65° C. in the presence of excess DIEA. The solutions were dried under high vacuum, dissolved in 50% aqueous acetonitrile and were loaded directly onto a Vydac reversed-phase C-18 (5 μm, 300 Å, 0.46×25 cm) HPLC column. The products were separated using a linear 0-80% buffer B gradient over 40 min at a flow rate of 1 mL/min.

The HPLC profile of the crude product is depicted in FIG. 3B. The main product (50% isolated yield) was unambiguously characterised by NMR, ES-MS and chiral amino acid analysis as the all-L target monocyclic product 7a. A $^1$H NMR absorption at 11.5 ppm confirmed that the product contained the free hydroxy substituent, and thus did not have the ester structure but rather the target cyclic amide structure. Further, a small amount of the C-terminally racemised product 7b (see FIG. 3B) was also isolated. A chiral amino acid analysis of the product confirmed the presence of a D-Ala residue.

Cyclisation Using 6-nitro-2-Hydroxybenzyl Auxiliary.

As the 5-nitro-2-hydroxybenzyl auxiliary is not readily removed after cyclisation, we examined cyclisation using the 6-nitro-2-hydroxybenzyl auxiliary peptide 2a. The ortho-nitro substituent, while maintaining a similar activation effect on the ring contraction of the cyclic intermediate 6a (compared to 5a), has the added benefit that it should render the auxiliary photolabile. The linear peptide 2a was synthesised and treated as described above for the 5-nitro-2-hydroxy derivative. Thus cyclisation (at 1 mM in DMF, 1 eq. BOP/2 eq. DIEA) was performed at rt for 3 h, followed by addition of excess DIEA (10eq) and heating to 65° C. for 1 hour. The major product was isolated in 39% yield, and characterised by NMR and chiral amino acid analysis as the all-L cyclo-pentapeptide 8a. A small amount of the C-terminal racemised cyclic product (containing a D-Ala) 8b was also isolated.

A.

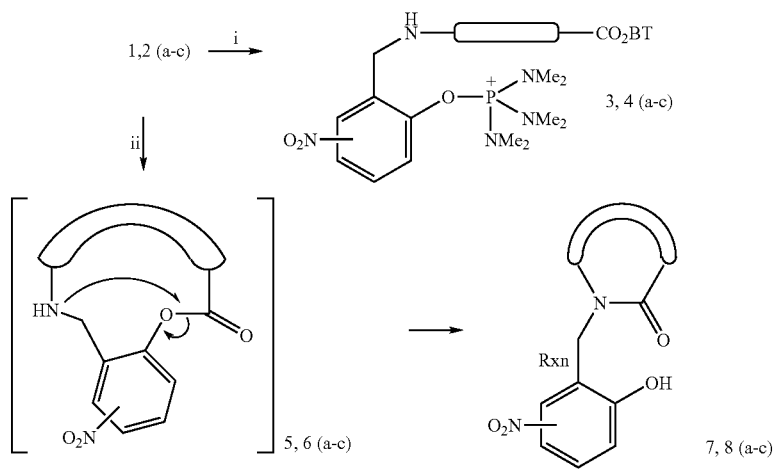

B.

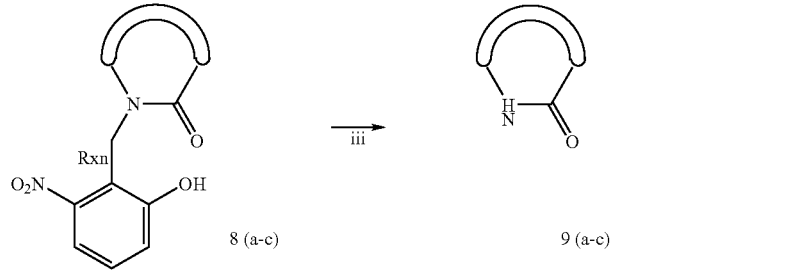

(a) ☐ = Ala-Phe-Leu-Pro-Ala
(b) = Ala-Phe-Leu-Pro-(D)Ala
(c) = Phe-Leu-Pro-Ala-Ala

Similarly N-(6-nitro-2-hydroxybenzyl)Phe-Leu-Pro-Ala-Ala 2c (SEQ ID NO:19) was assembled and cyclised as above. The all-L cyclo pentapeptide 8c was isolated in 45% yield.

Figure 4:
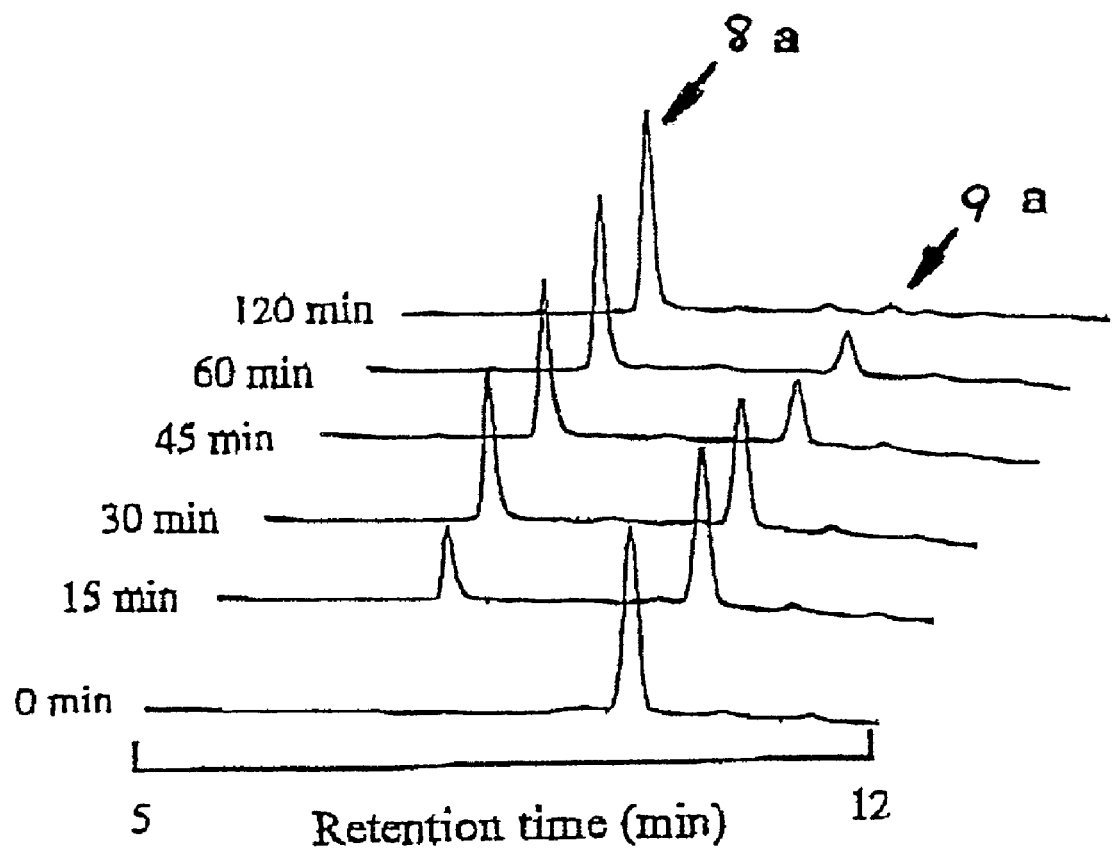
FIG. 4 shows the results of HPLC analysis of the photolysis of cyclic peptide 8a at timed intervals. A 0.15 mM solution of peptide 8a in MeOH/1% AcOH was photolysed using a standard UV lamp, and at different time intervals small aliquots were injected onto a Zorbax reversed-phase C-18 (3 μm, 300 Å, 0.21×5 cm) HPLC column. The products were separated using a linear 0-80% buffer B gradient over 10 min at a flow rate of 200 μL/min (detection at 214 nm).

Removal of the auxiliary. Cyclic peptide 8a was then subjected to photolysis at 366 nm, using a standard UV lamp, in a range of solvent conditions. In most solvents (MeOH, MeOH/AcOH, THF/AcOH, dioxane) the nitrobenzyl substituent on the backbone nitrogen is readily removed to generate the target cyclic peptide 9a (Scheme 5, B). FIG. 4 illustrates the clean and efficient conversion (8a to 9a).

The cyclic product was characterised by chiral amino acid analysis and $^1$H NMR. The spectral data were in good agreement with the reported data. Furthermore, an independent sample of cyclic peptide, prepared by the cyclisation of Phe-Leu-Pro-Ala-Ala according to Schmidt et al (1997), coeluted with the product obtained from photolysis.

The same product 9a was obtained from photolysis of the regio analogue 8c. The racemised cyclic product 8b was photolysed, and similarly produced the unsubstituted D-Ala containing product 9b, which coeluted with an independently synthesised sample.

Experimental to Example 2

This section describes the experimental details of the use of ring contraction concepts for the synthesis of small cyclic peptides.

Ring Contraction

Synthesis of Ring Contraction Auxiliaries

N-(2-Bromoethoxy)phthalimide

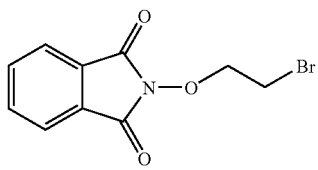

$C_{10}H_8BrNO_3$
Exact Mass: 268.97
Mol. Wt.: 270.08

N-(2-Bromoethoxy)phthalimide was synthesised by a modification of the procedure of Bauer and Suresh (Bauer et al 1963). N-Hydroxyphthalimide (80 g, 0.49 mol), triethylamine (150 mL, 1.08 mol), and 1,2-dibromoethane (175 mL, 2.30 mol) were combined in DMF (575 mL) and stirred at room temperature overnight. Solids were filtered and washed with DMF and the filtrate was diluted with water (4.0 L) and the resulting precipitate filtered, dissolved in EtOAc (500 mL), and washed with 1 N HCl (2×100 mL), water (1×100 mL), and dried over MgSO$_4$. Volatiles were removed in vacuo, and the resulting solid recrystallised from 95% EtOH to give (9) as a white solid (87.1 g, 70%): mp. 94-96° C.; lit. mp. 94-96° C. $^1$H NMR (CDCl$_3$): δ 7.82 (m, 4H), 4.49 (t, 2H, J=6.9 Hz), 3.65 (t, 2H, J=6.9 Hz).

N-[2-[S-(4-Methylbenzyl)thio]ethoxy]phthalimide

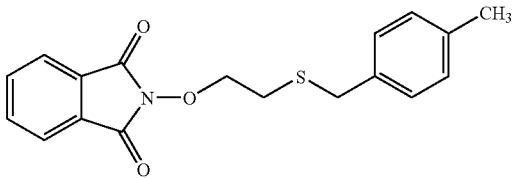

$C_{18}H_{17}NO_3S$
Exact Mass: 327.09
Mol. Wt.: 327.40

N-[2-[S-(4-Methylbenzyl)thio]ethoxy]phthalimide was synthesised by a modification of the procedure of Canne et al (Flanigan, 1971). Bromide (55.15 g 217 mmol), 4-methylbenzyl mercaptan (30 g, 217 mmol) and DIPEA (38.55 mL, 217 mmol) were combined in acetonitrile (200 mL) and stirred at room temperature for 72 h. Volatiles were removed in vacuo, EtOAc (500 mL) added and filtered. Solids were washed with EtOAc, and the organics were combined and washed with 1 N HCl (2×200 mL), brine (1×200 mL) and water (1×200 mL) and dried over MgSO$_4$. Volatiles were removed in vacuo and the resulting solid recrystallised from EtOAc:hexane, 1:1 to yield (10) as a white solid (50.14 g, 71%): mp. 82-84° C.; $^1$H NMR (CDCl$_3$) δ 7.80 (m, 4H), 7.18 (d, 2H, J=8.0 Hz), 7.04 (d, 2H, J=8.0 Hz), 4.22 (t, 2H, J=7.4 Hz), 3.75 (s, 2H), 2.79 (t, 2H, J=7.4 Hz), 2.27 (s, 3H).

S-(4-Methylbenzyl)-2-(aminooxy)ethanediol

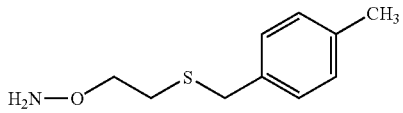

$C_{10}H_{15}NOS$
Exact Mass: 197.09
Mol. Wt.: 197.30

S-(4-Methylbenzyl)-2-(aminooxy)ethanediol was synthesised by a modification of the procedure by Osby et al (1993). The N-substituted pthalimide (20.0 g, 61.1 mmol) was suspended in a solution of 2-propanol (550 mL) and water (85 mL) and cooled to below 10° C. NaBH$_4$ (18.9 g, 252 mmol) was added portionwise so that the temperature did not exceed this temperature. The mixture was allowed to warm to room temperature and stirred overnight. Acetic acid (135 mL) was slowly added until the bubbling ceased, and the flask was stoppered and heated to 50° C. for 3 h Volatiles were removed in vacuo, and the resulting oil solution diluted with 1 N NaOH and extracted with EtOAc (4×200 mL). The hydroxylamine was then extracted into a solution of HCl (2N, 500 mL) and washed with EtOAc (2×250 mL). NaCO$_3$ was then added to the aqueous phase until bubbling ceased, and the hydroxylamine extracted into EtOAc (3×250 mL). The combined organic layers were washed with H$_2$O (2×250 mL) and dried over MgSO$_4$. Volatiles were removed in vacuo, and the resulting oil purified by flash chromatography (Hexane EtOAc, 3:1) to yield as a clear colourless oil (10.04 g, 84%): $^1$H NMR (CDCl$_3$): δ 7.21 (d, 2H, J=8.0 Hz), 7.12 (d, 2H, J=8.0 Hz), 5.40 (br s, 2H), 3.77 (t, 2H, J=6.5 Hz), 2.71 (s, 2H), 2.64 (t, 2H, J=6.5 Hz), 2.33 (s, 3H).

Application of Ring Contraction Auxiliary (Scheme 6) NH₂CH₂CH₂SSCH₂CH₂-Gly-Arg-Pro-Phe-Gly-OH (SEQ ID NO:21)

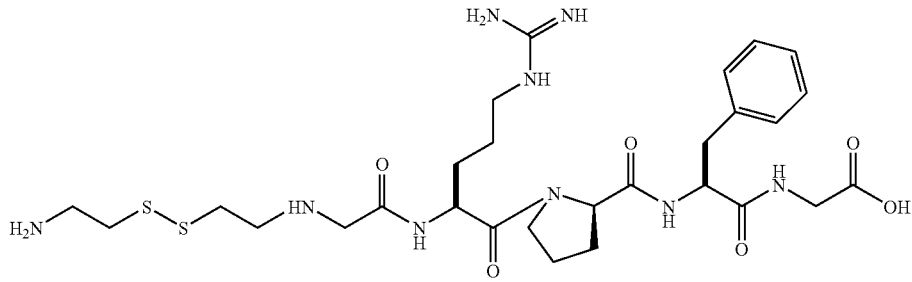

C$_{28}$H$_{45}$N$_9$O$_6$S$_2$
Exact Mass: 667.29
Mol. Wt. 667.85

The peptide NH₂CH₂CH₂SSCH₂CH₂-Gly-Arg-Pro-Phe-Gly-OH (SEQ ID NO:21) was synthesised in stepwise fashion from Boc-Gly-Pam resin (0.5 g, 0.5 mmol/g) by established methods, using in situ neutralisation/HBtU activation protocols for Boc chemistry. The Pmc protecting group was used for the Arg residue. Coupling reactions were monitored by quantitative ninhydrin assay and were typically >99.9%. After chain assembly was complete and the N-Boc group removed with neat TFA (2×1 min treatment) and neutralised with 10% DIEA in DMF (2×1 min treatment), the peptide was bromoacetylated by the method of Robey (Robey, F. A., Fields, R. L., Anal. Biochem., 1989 177 373-377). Bromoacetic acid (277.9 mg, 2.0 mmol) was dissolved in CH₂Cl₂ (2 mL), to which was added DIC (126.2 mg, 1 mmol). After activation for 10-15 min to form the symmetric anhydride, the mixture was diluted with DMF (2 mL), added to the peptide resin, and coupled for 30 min. The resin was washed with DMSO, and cystamine (2 M in DMF, 4 mL) was allowed to react with the bromoacetylated peptide resin for 16 h. The linear peptide was cleaved from resin by the addition of thiocresol: cresol, 1:1 (1 mL), followed by treatment with HF (10 mL) for 1 h at −5° C. After removal of the HF under reduced pressure, the crude peptide was precipitated in anhydrous Et₂O and filtered to remove the scavengers. The peptide was dissolved in HOAc: H₂O, 1:19, filtered and the filtrate lyophilized. NH₂CH₂CH₂SSCH₂CH₂-Gly-Arg-Pro-Phe-Gly-OH was purified by semi-preparative HPLC (20-80% B over 60 min) to give the wanted material (79.6 mg 47%) yield. MS [M+H]⁺=668.1 (expected 668.3).

HSCH₂CH₂-Gly-Arg-Phe-Gly-OH (SEQ ID NO:22)

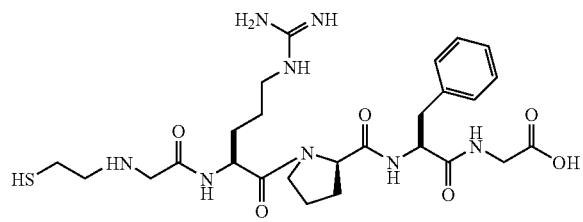

C$_{26}$H$_{40}$N$_8$O$_6$S
Exact Mass: 592.28
Mol. Wt.: 592.71

The disulfide (66.8 mg, 0.10 mmol) was dissolved in a 0.03 M solution of NH₄⁺OAc⁻ (20 mL).

Tris(2-carboxyethyl)phosphine hydrochloride salt (TCEP) (35.6 mg, 0.15 mmol) was added portionwise to the stirred solution at r.t. After a further 3 h at this temperature the resulting mixture was lyophilized to give a white powder. The peptide HSCH₂CH₂-Gly-Arg-Phe-Gly-OH (SEQ ID NO:22) was purified by semi-preparative HPLC (20-80% B over 60 min) to yield a white powder (40.1 mg, 68%); MS [M+H]⁺=593.1 (expected 593.3).

Cyclo-(SCH₂CH₂-Gly-Arg-Pro-Phe-Gly) (SEQ. ID NO:23)

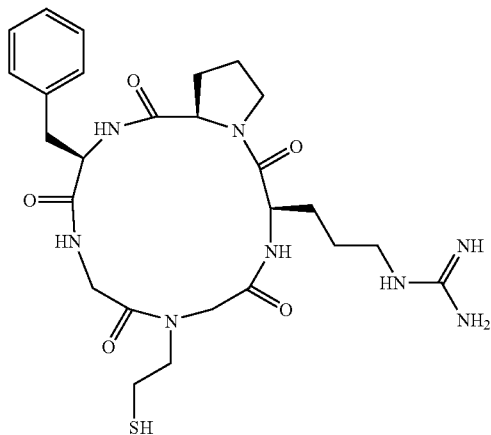

C$_{26}$H$_{38}$N$_8$O$_5$S
Exact Mass: 574.27
Mol. Wt.: 574.70

The linear peptide HSCH₂CH₂-Gly-Arg-Pro-Phe-Gly-OH (SEQ ID NO:24) (40.0 mg, 0.068 mmol) and BOP (88.4 mg, 0.2 mmol) was stirred in DMF (68 mL, 1×10⁻³ M) at −10° C. DIPEA (121 μL, 0.68 mmol) was added dropwise to the solution. The reaction was left to stir for a further 2 h at this temperature, before all volatiles were removed in vacuo. The peptide Cyclo-(SCH₂CH₂-Gly-Arg-Pro-Phe-Gly) (SEQ ID NO:23) was purified by semi-preparative HPLC (20-80% B over 60 min) to yield a white powder (12.2 mg, 31%); MS [M+H]⁺=743.2 (expected 743.4092).

Bis-[cyclo-Gly(CH₂CH₂S)-Arg-Pro-Phe-Gly] (SEQ ID NO:23)

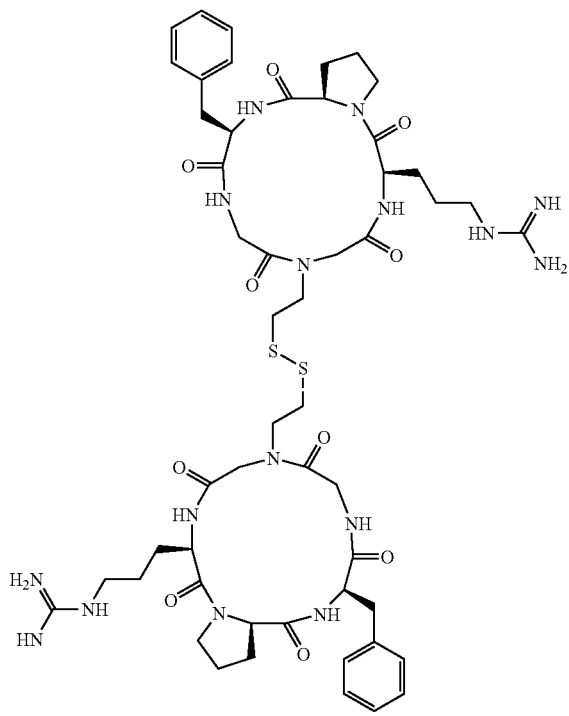

$C_{52}H_{14}N_{16}O_{10}S_2$
Exact Mass: 1146.52
Mol. Wt. 1147.38

The peptide Cyclo-(SCH₂CH₂-Gly-Arg-Pro-Phe-Gly) (SEQ ID NO:23) (12 mg, 0.016 mmol) was dissolved in a solution of Na₂HPO₄ (0.03 M) and stirred at room temperature overnight. The resulting solution was lyophilized to give a white powder. The peptide Bis-[cyclo-Gly(CH₂CH₂S)-Arg-Pro-Phe-Gly] (SEQ ID NO:23) was purified by reverse phase HPLC (20-80% B over 60 min) to yield a white powder (7.4 mg, 81%); MS $[M+2H]^{2+}$=574.22 (expected 574.27).

Cyclo-(Gly(CH₂CH₂SH)-Arg-Pro-Phe-Gly) (SEQ ID NO:25)

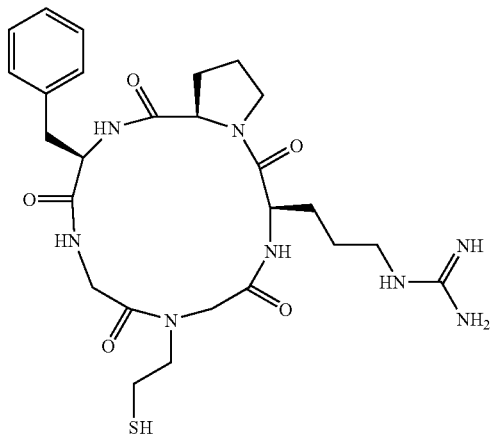

$C_{26}H_{38}N_8O_5S$
Exact Mass: 574.27
Mol. Wt.: 574.70

The disulfide (7.4 mg, 6.50 µmol) was dissolved in a 0.03 M solution of $NH_4^+OAc^-$ (20 mL). TCEP (4.75 mg, 20.0 µmol) was added portionwise to the stirred solution at r.t. After a further 3 h at this temperature the resulting mixture was lyophilized to give a white powder. The peptide Cyclo-(Gly(CH₂CH₂SH)-Arg-Pro-Phe-Gly) (SEQ ID NO:25) was purified by semi-preparative HPLC (20-80% B over 60 min) to yield a white powder (5.5 mg, 74%); MS $[M+H]^+$=575.24 (expected 575.28).

Experimental to Synthesis of cyclo[Ala Phe Leu Pro Ala] (SEQ ID NO:17) Cyclisation Experiments Cyclisation of auxiliary-containing peptides 1 and 2:1 equivalent of BOP and 2 equivalents of DIEA in DMF were added to a 1 mM solution of the linear peptide in DMF and stirred for 3 h at rt. 10 equivalents of DIEA were then added, and the solution heated at 65° C. for 1 h. DMF was removed in vacuo, and the crude product was dissolved in acetonitrile/water (1:1) and purified by RP-HPLC. Cyclisation of other linear peptides: Cyclisations were performed using a 1 mM solution of linear peptide in DMF. 3 equivalents of BOP and 5 equivalents of DIEA were added, and the solution stirred for 3 h at rt. Work-up was as described above.

Cyclo-[N-(5-nitro-2-hydroxybenzyl)-Ala-Phe-Leu-Pro-Ala] (7a) (SEQ ID NO:26). Cyclisation of N-(5-nitro-2-hydroxybenzyl)-Ala-Phe-Leu-Pro-Ala 1a (SEQ ID NO:26) (30 mg of the TFA salt, 0.038 mmol), produced 7a (12.5 mg, 0.019 mmol) in 51% yield: ES-MS Mr 650.2, calcd for $C_{33}H_{42}N_6O_8$, 650.3 (monoisotopic). ¹H NMR (500 MHz, DMSO-d₆, ppm) δ 11.5 (s, 1H, OH), 8.40 (d, 1H, $NH_{Leu}$), 8.02 (dxd, 1H, H-ar), 7.70 (d, 1H, H-ar), 7.4 (d, 1H, $HN_{Phe}$), 7.20-7.30 (m, 5H, H-Phe), 6.99 (d, 1H, H-ar), 6.54 (d, 1H, H—$N_{Ala}$), 5.00 (s, 1H, ArCHhN—), 4.91 (m, 1H, α-Ala⁵), 4.75 (q, 1H, α-Ala¹), 4.59 (m, 1H, α-Phe), 4.50 (m, 1H, α-Leu), 4.27 (t, 1H, α-Pro), 3.88 (d, 1H, ArCHhN—), 3.62 (m, 1H, δ-Pro), 3.37 (m, 1H, δ-Pro), 2.97 (m, 1H, β-Phe), 2.82 (m, 1H, β-Phe), 2.04 (m, 2H, β-Pro), 1.88 (m, 1H, γ-Pro), 1.73 (m, 1H, β-Leu), 1.65 (m, 1H, γ-Pro), 1.44 (m, 1H, γ-Leu), 1.33 (m, 1H, γ-Leu), 1.24 (d, 3H, β-Ala⁵), 0.91 (d, 3H, β-Ala¹), 0.85 (m, 6H, δ-Leu). ¹³C NMR (75 MHz, DMSO-d₆, ppm) 172.61, 170.34, 170.07, 169.95, 169.47, 160.40, 139.73, 136.88, 129.31, 128.14, 126.50, 125.72, 124.21, 122.65, 115.00, 61.04, 56.50, 55.74, 48.70, 46.31, 44.34, 41.37, 38.28, 31.30, 24.20, 22.81, 22.68, 21.17, 18.97, 15.35.

Cyclo-[N-(6-nitro-2-hydroxybenzyl)-Ala-Phe-Leu-Pro-Ala] (8a) (SEQ ID NO. 27). From cyclisation of N-(6-nitro-2-hydroxybenzyl)-Ala-Phe-Leu-Pro-Ala 2a (SEQ ID NO. 27) (20 mg of the TFA salt, 0.025 mmol), 8a (6.5 mg, 0.010 mmol) was obtained in 39% yield: ES-MS Mr 650.6, calcd for $C_{33}H_{42}N_6O_8$: 650.3 (monoisotopic). ¹³C NMR (75 MHz, CD₃OD, ppm) δ 178.07, 176.95, 174.54, 174.32, 173.72, 159.11, 153.19, 140.41, 131.99, 129.96, 129.54, 127.57, 121.18, 116.57, 62.75, 60.67, 58.55, 54.05, 51.15, 44.54, 43.41, 34.85, 33.67, 25.03, 24.13, 22.30, 21.31, 15.49, 13.89.

Cyclo-[N-(6-nitro-2-hydroxybenzyl)-Phe-Leu-Pro-Ala-Ala] (8c) SEQ ID NO:28). From cyclisation of the N-(6-nitro-2-hydroxybenzyl)-Phe-Leu-Pro-Ala-Ala (SEQ ID NO:28 (20 mg of the TFA salt, 0.025 mmol), 8a (7.3 mg, 0.011 mmol) was obtained in 44% yield: ES-MS Mr 650.2, calcd for $C_{33}H_{42}N_6O_8$: 650.3 (monoisotopic). ¹³C NMR (75 MHz, DMSO-d₆, ppm) δ 171.43, 171.00, 169.46, 167.56, 156.65, 138.43, 129.24, 129.05, 128.32, 128.18, 126.08, 119.50, 115.87, 114.60, 62.18, 60.69, 51.07, 49.38, 46.57, 45.46, 41.54, 38.17, 33.65, 31.43, 24.37, 22.73, 22.32, 21.06, 17.87, 16.92.

Cyclo-[Ala-Phe-Leu-Pro-Ala] (9a) (SEQ ID NO:17). a) Cyclo-[N-(6-nitro-2-hydroxybenzyl)-Ala-Phe-Leu-Pro-Ala] (SEQ ID NO:27 (1 mM MeOH) was purged with nitrogen for 30 minutes and then photolysed with a standard laboratory UV lamp (366 nm, 0.25 A) for three hours. The MeOH was evaporated and the residue dissolved in 50% buffer B, and the solution loaded directly onto a Vydac C18 column (preparative) for HPLC purification. Cyclo-[Ala-Phe-Leu-Pro-Ala] (SEQ ID NO:17) was isolated in 52% yield. The product coeluted with an independently synthesised sample. ES-MS Mr 499.4, calcd for $C_{26}H_{37}N_5O_5$, 499.3 (monoisotopic). b) Photolysis of purified cyclo-[N-(6-nitro-2-hydroxybenzyl)-Phe-Leu-Pro-Ala-Ala] (SEQ ID NO:28) was perfomed as described above. Cyclo-[Phe-Leu-Pro-Ala-Ala] (SEQ ID NO:30) was isolated in 28% yield. The product coeluted with a independently synthesised sample. ES-MS Mr 499.1, calcd for $C_{26}H_{37}N_5O_5$, 499.3 (monoisotopic).

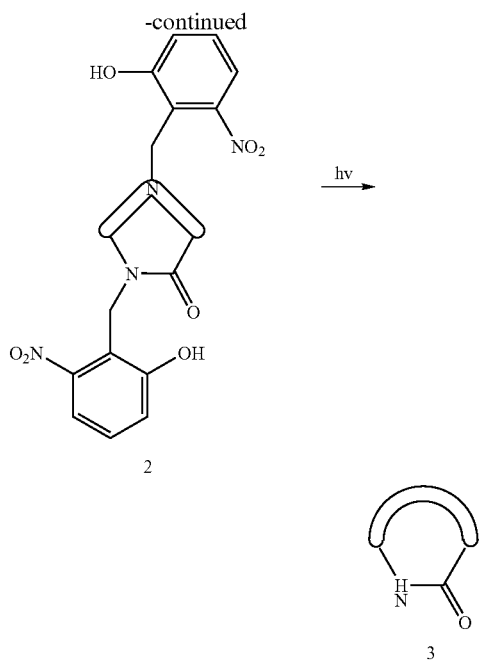

EXAMPLE 3

Backbone Substitution and Ring Contraction in Solution

In this example we demonstrate that cyclisation via ring contraction is significantly more facile for backbone substituted peptides than for their backbone unsubstituted analogues. We have employed the 6-nitrobenzyl-2-hydroxy auxiliary both as a backbone substituent and a ring contraction auxiliary. The person skilled in the art will appreciate that the Hnb-group could readily be replaced by many other auxiliaries, such as those described above. The general reaction scheme is as follows: Cyclisation of the disubstituted linear peptide 1 produces disubstituted head-to-tail cyclic peptide 2. Both substituents on the backbone are then removed by photolysis to form the target cyclic peptide 3.

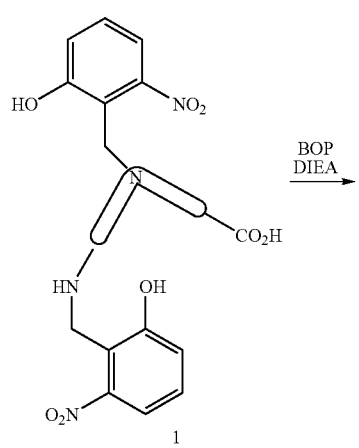

Scheme 8: A Combination Approach: Backbone Substitution and Ring Contraction.

In order to evaluate the roles of ring contraction and position of the backbone substituent in the formation of cyclic tetrapeptides, we synthesised the following set of linear peptides:

1a. [Hnb]Tyr-Arg-Phe-Gly (SEQ ID NO:31)

1b. Tyr-[Hnb]Arg-Phe-Gly (SEQ ID NO:32)

1c. Tyr-Arg-[Hnb]Phe-Gly (SEQ ID NO:33)

1d. [Hnb]Tyr-[Hnb]Arg-Phe-Gly (SEQ ID NO:34)

1e. [Hnb]Tyr-Arg-[Hnb]Phe-Gly (SEQ ID NO:35)

All peptides were cyclised in parallel under the same conditions (either rt or 65° C.), on a 1 mg peptide scale. A 1 nM solution of the peptide (1a-e) in DMF was treated with 1 eq. of BOP and 2 eq of DIEA. After 3 hours at rt, 10 eq DIEA was added, and stirring continued at rt for 6 h or at 65° C. for 1 h. The solvent was then removed, and the residue was dissolved in acetonitrile/water and analysed by HPLC and MS.

Peptide 1a readily underwent initial ring closure, but ring contraction to the target product was slow and required heating for extended periods (65° C./20 h). If cyclisation of 1a was carried out at rt (6 h) no cyclic peptide was detected in the crude product. The control peptide 1c generated mainly cyclic dimer (MW: calcd for $C_{66}H_{76}N_{16}O_{16}$=1348.6, exp=1348.2) and linear diner (MW: calcd for $C_{66}H_{78}N_{16}O_{17}$=1366.5 (monoisotopic), exp=1366.7), with only small amounts of target monocycle formed. Control peptide 1b under cyclisation conditions generated a complex mixture of products.

Figure 5:
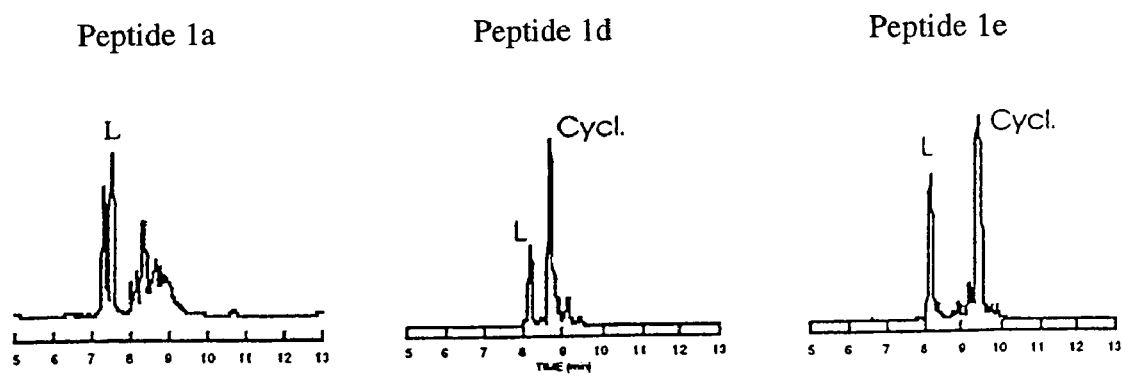
FIG. 5 shows the HPLC profile of the reaction products from cyclisation of peptides 1a, 1d and 1e, (i) 1 eq BOP, 2 eq DIEA, 1 mM in DMF; (ii) 10 eq DIEA, 6 h at rt. L=Linear peptide, Cycl=head-to-tail cyclic product.

In contrast, for peptides 1d and 1e, which contain both a backbone substitutent and a ring contraction auxiliary, ring closure and ring contraction was almost complete under the same mild reaction conditions (6 h at rt). FIG. 5 shows the cyclisation profiles of peptides 1a, 1d and 1e after 6 h at rt. Under these mild conditions, peptide 1a did not undergo any significant ring contraction, and the crude product contained largely linear peptide (L). Peptides 1d and 1e on the other hand produced the target cyclic peptides cyclo-[(Hnb)Tyr-(Hnb)Arg-Phe-Gly] 2d (SEQ ID NO:36) and cyclo-[(Hnb)Tyr-Arg-(Hnb)Phe-Gly] 2e (SEQ ID NO:37) respectively (MW: calcd for $C_{40}H_{43}N_9O_{11}$=825.3 (monoisotopic), exp (Cycl peptide 2d)=825.1, exp (Cycl peptide 2e)=825.1) in excellent purity and yield. Note that the cyclic products have the same molecular weight but different substitution patterns.

These results clearly demonstrates that the N-backbone substituent plays a vital role in facilitating the ring contraction for highly constrained ring systems such as tetrapeptides. It is also clear from this that our combination strategy will allow access to a range of cyclic tetrapeptides and peptidomimetics.

Large scale cyclisation of peptide 1d (10 mg) produced the cyclic (disubstituted) product 2d in 61% yield after HPLC isolation. Photolysis of this product (3 h/DMF) generated the target cyclo-[Tyr-Arg-Phe-Gly] 3. The overall yield after cyclisation, purification, photolysis and HPLC isolation was 28% (by weight).

Evaluating Racemisation

To examine the extent of racemisation during cyclisation we elected to synthesise and cyclise the following set of peptides:

1f. [Hnb]Gly-[Hnb]Tyr-Arg-Phe (SEQ ID NO:38)

1g. [Hnb]Gly-Tyr-[Hnb]Arg-Phe (SEQ ID NO:39)

1h. [Hnb]Gly-Tyr-Arg-[Hnb]Phe (SEQ ID NO:40)

Figure 6:
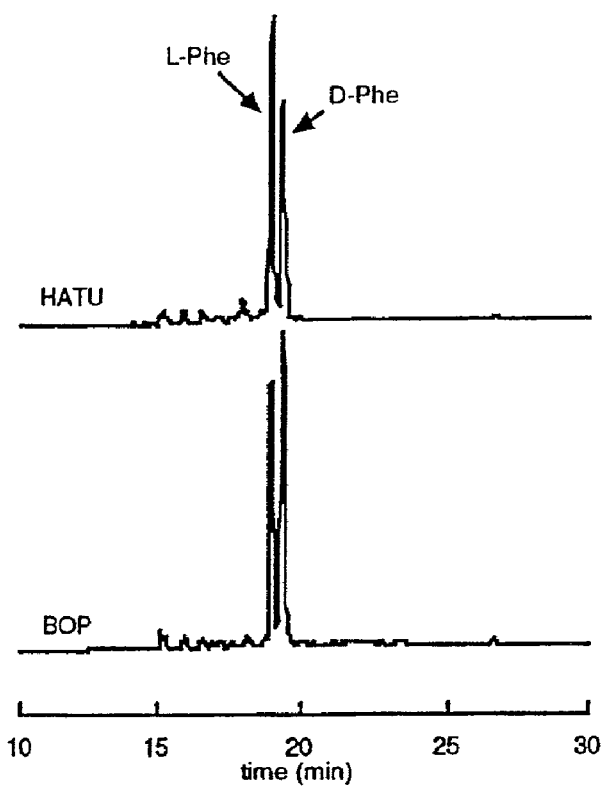
FIG. 6 shows an HPLC comparison of the crude cyclisation products of peptide 1f using either HATU or BOP as cyclisation reagent. The two major peaks in the chromatograms have a molecular weight of 825 g/mol, corresponding to the target cyclic product cyclo-[(Hnb)Gly-(Hnb)Tyr-Arg-Phe] (SEQ ID NO:2). The first eluting product is the all-L isomer, the second product contains D-Phe.

Note that cyclisation of these peptides will generate cyclic products of different structure but the same MW. Cyclisations were initially carried out on small scale (1 mg). Peptides 1f and 1g under our 'standard' cyclisation conditions generated two monocyclic products of the correct molecular weight. No starting material or other products were detected. The HPLC profile for peptide 1f is shown in FIG. 6.

Cyclisation of peptide 1h on the other hand was somewhat slower, and generated mainly D-Phe cyclic product; the product contains 60% linear peptide.

In order to investigate racemisation further, the following combination of reagents and solvents were evaluated:

| Solvent: | Dioxane or DMF. |
|---|---|
| Activating reagents: | BOP or HATU. |
| Base: | DIEA or Symmetric collidine. |
| time/temp: | 20 h at rt or 1 h at 70° C. |

A total of 16 reaction conditions were applied in parallel including all combinations of the above solvents, reagents, bases and conditions (1 eq activating reagent, 2 eq base, 1 mM of peptide 1f in solvent). The reaction products were analysed by removing the solvent in the Genevac and resuspending the residue in acetonitrile/water, followed by HPLC analysis. Dioxane proved to be a poor solvent for the cyclisation. In most of the cases examined, only starting material could be detected. This is most likely due to the fact that the linear peptide is hardly soluble in dioxane. For the DMF experiments, HATU activation generated more L-cyclic peptide, but the effect is small (see FIG. 4). Changing collidine for DIEA had no effect on the product profile, with the same amount of racemisation being observed.

A large scale cyclisation was performed on peptide 1f, and two cyclic products were isolated by HPLC as a mixture in 68% yield (by weight). The two products could be separated by HPLC and photolysed to generate one unsubstituted cyclic peptide each (MW=523 gr/mol) (non-coeluting). One of the products coeluted with the product from peptide 1d, and therefore was assigned to be the all-L cyclo-[Gly-Tyr-Arg-Phe] (SEQ ID NO:41). The second eluting product was assigned to be the cyclo-[Gly-Tyr-Arg-(D)phe] (SEQ ID NO:41). Photolysis of the mixture generated a mixture of the two cyclic unsubstituted peptides in 34% yield (overall yield 23%). The first product coelutes with the product obtained by cyclisation and subsequent photolysis of peptide 1d.

Combination of Ring Contraction and Backbone Substitution for the Synthesis of cyclo-[Tyr-Arg-Phe-Ala] (SEQ ID NO:42), with Cyclisation at the Tyr-to-Ala Site.

As mentioned in the background section of this specification, turn-inducing elements such as Gly and Pro can favour cyclisation. Here we apply our combination technology to the synthesis of peptides that do not contain turn-inducing amino acids. In this example we employ the combination strategy (backbone substitution and ring contraction auxiliaries) for the synthesis of a very difficult target, an all-L cyclic tetrapeptide cyclo-[Tyr-Arg-Phe-Ala] (SEQ ID NO:42).

4[Hnb]Tyr-Arg-[Hnb]Phe-Ala (SEQ ID NO:43)

Small scale (1 mg peptide) cyclisation was investigated using the following conditions:

i. 1 mM solution of peptide in DMF, 1 eq BOP, 2 eq DIEA, 3 h at rt ii. addition of 10 eq. DIEA iii. 20 h at rt; or 1 h at 70° C.; or 20 h at 70° C.

Peptide 4 under these cyclisations conditions provided cyclic product of the correct molecular weight.

To verify whether cyclisation of peptide 4 could be improved, an optimisation was carried out, in which solvent and temperature conditions were altered in the above standard protocols:

Solvents: Temperature conditions in (iii):

| DMF | 20 h | rt |
|---|---|---|
| DMSO | 1 h | 70° C. |
| Dioxane | 20 h | 70° C. |
| Toluene | | |

Figure 7:
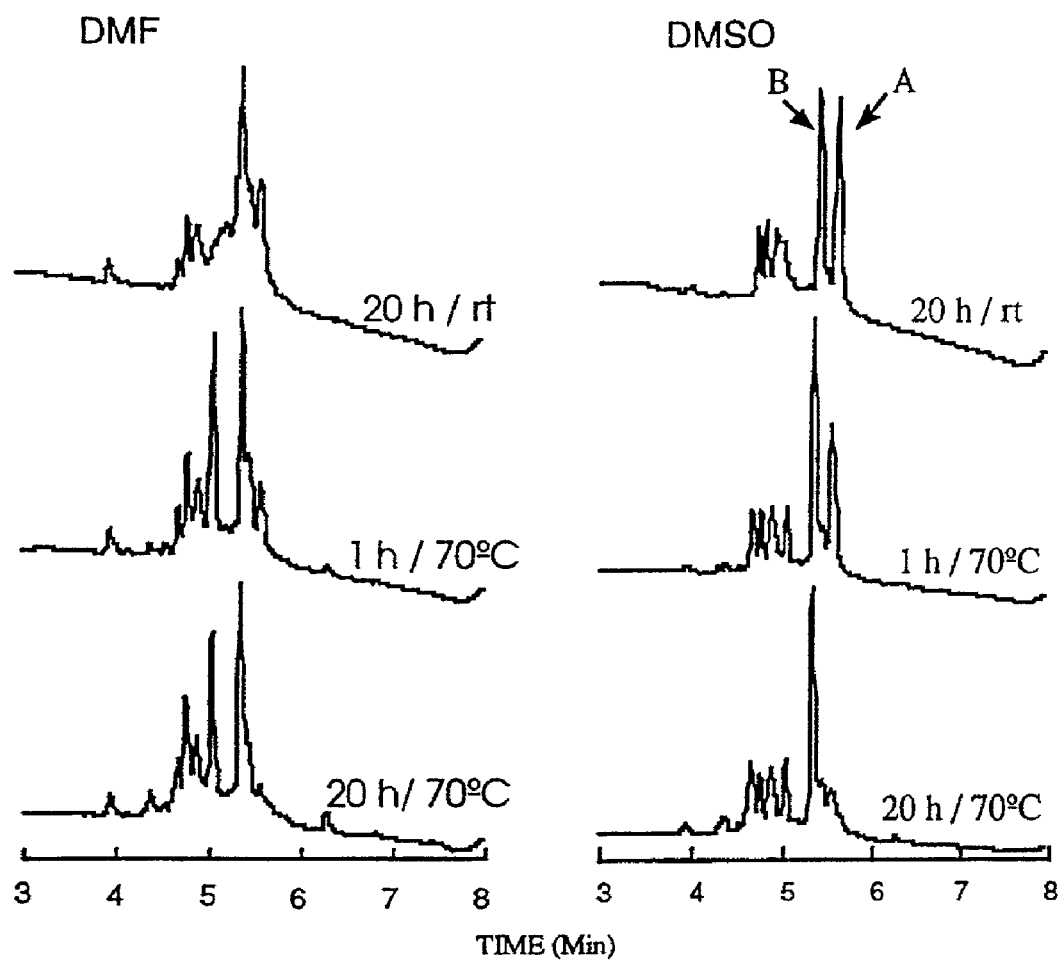
FIG. 7 shows the reaction profiles obtained from cyclisation of peptide 4 under a range of reaction conditions.

With dioxane or toluene as solvent, very poor yields of cyclic product were obtained at any of the temperatures used. In general, DMSO produced significantly cleaner reaction profiles when compared to DMF, as illustrated in FIG. 7.

The results of the DMSO experiments can be summarised as follows:

20 h/rt: Two main cyclic products are formed (A and B) both display the correct molecular weight in ES-MS (MH+ at 840 m/z).

1 h/70° C.: Similar results, but one of the two monocyclic products (A) is decreased in intensity.

20 h/70° C.: Only one monocyclic product is formed (B). Monocyclic product (A) is not present.

A large scale cyclisation (60 mg of linear peptide) was carried out in DMSO at rt (20 h), and the two monocyclic products were isolated by HPLC (combined yield: 46%, ratio is about 1/1).

The two cyclic products were subjected to heating and to photolysis:

Product A: Unstable to heat; the product fully decomposed upon heating for 20 h at 70° C. in DMSO. Stable to hydrolysis (aqueous buffer at pH 9).

Photolysis of this compound in DMSO proceeded reasonably well; both HnB groups were removed, and cyclo-[Tyr-Arg-Phe-(D)Ala] (SEQ ID NO:42) was isolated by HPLC in 42% yield.

The presence of D-Ala was confirmed by chiral amino acid analysis.

Product B: Stable to heat and to hydrolysis conditions aqueous buffer at pH 9).

Photolysis did not proceed very readily.

Chiral amino acid analysis confirmed the presence of L-Ala.

This product is the all-L cyclo-[(Hnb)Tyr-Arg-(Hnb)Phe-Ala] (SEQ ID NO:44).

To further assess the versatility of the combination approach, we examined cyclisation of peptide 5 under the 'normal' conditions:
(i) 1 eq Bop, 2 eq DIEA, 1 mM DMF (3 h, rt);
(ii) 10 eq DIEA (12 h at rt).

5. [Hnb]Ala-Tyr-[Hnb]Arg-Phe (SEQ ID NO:45)

The cyclisation at the Ala-to-Phe site was carried out on a large scale (30 mg). One cyclic product, which displayed the expected molecular weight and isotope distribution pattern in ES-MS, was isolated by preparative HPLC in 53% yield.

The surprising results reported in this example illustrate the power of the combination approach for the synthesis of cyclic peptides and peptidomimetics. One skilled in the art will also realise the potential of applying this combination to the synthesis of cyclic peptides on solid supports.

Experimental to Example 3

Peptide synthesis: The linear peptides 1a-e were synthesised on chlorotrityl resin (0.91 mmol/g) Fmoc-Gly-OH was loaded on the resin in the manner recommended by the supplier (Pepchem). The peptides were then assembled using Fmoc-SPPS protocols. Removal of the Fmoc group was carried out by treating the Fmoc-peptide resin with 50% piperidine in DMF (2×2 min). Coupling of the following amino acid was carried out as follows: 4 equivalents of Fmoc amino acid was dissolved in DMF containing 4 equivalents of HBTU (0.5 M solution of HBTU). After 1 min the solution was added to the amino-peptide resin and the resin shaken for 10 min. A ninhydrin test was performed to ensure complete acylation. If acylation was not complete, the reaction mixture was left longer until ninhydrin test was negative (>99% coupling). The 2-hydroxy-6-nitrobenzyl auxiliary was attached via reductive amination, as described in Example 2. After introduction of the Hnb-group, the next residue was coupled using the same HBTU activation protocol, but coupling reaction was left at rt for 20 h. The peptides were then cleaved from the resin by treatment with 95% TFA/5% water (45 min at rt). The TFA was evaporated, and the peptide precipitated with ether. The precipitate was dissolved in acetonitrile/water and loaded onto a preparative HPLC column, and a 2%/min gradient (100% A to 20% A) used to elute the products. The fractions containing the target products were then combined and analysed by HPLC (purity) and ES-MS.

Peptide 1a was isolated in 50% yield (from the theoretical substitution value of the resin).

ES-MS: calcd for $C_{33}H_{40}N_8O_9$=692.3 (monoisotopic), exp=692.4.

Peptide 1b was isolated in 54% yield (from the theoretical substitution value of the resin). ES-MS: calcd for $C_{33}H_{40}N_8O_9$=692.3 (monoisotopic), exp=692.2. Peptide 1c was isolated in 25% yield (from the theoretical substitution value of the resin)

ES-MS: calcd for $C_{33}H_{40}N_8O_9$=692.3 (monoisotopic), exp=692.2.

Peptide 1d was isolated in 28% yield (from the theoretical substitution value of the resin)

ES-MS: calcd for $C40H_{45}N_9O_{12}$=843.3 (monoisotopic), exp=843.2.

Peptide 1e was isolated in 22% yield (from the theoretical substitution value of the resin)

ES-MS: calcd for $C_{40}H_{45}N_9O_{12}$=843.3 (monoisotopic), exp=843.2.

Large scale cyclisation of peptide 1d: 0.011 mmol of linear peptide 1d (10 mg of the TFA salt) was dissolved in DMF (5 mL) containing 0.012 mmol BOP (5.2 mg). DMF (5 mL) containing 0.025 mmol DIEA (4.3 µL) was added, and the mixture stirred for 3 hours (rt). 0.25 mmol DIEA (40 µL) was added and the reaction left stirring for another 20 hours. The solvent was evaporated under high vacuum, the residue dissolved in acetonitrile/water and loaded on a preparative HPLC column. A 1.5% gradient was used to elute the products (100% buffer A to 20% buffer A). Cyclo-[(Hnb)Tyr-(Hnb)Arg-Phe-Gly] 2d (SEQ ID NO:46) (5.3 mg, 0.0064 mmol, 61%) was isolated: ES-MS: calcd for $C_{40}H_{43}N_9O_{11}$=825.3 (monoisotopic), exp=825.1.

The product 2d (5 mg, 6×10$^{-3}$ mmol) was then dissolved in DMF (10 mL), the solution placed in a beaker and photolysed for 3 hours using a UV lamp (350-365 nm, 20 W, Black/White/Blue). The DMF was removed under vacuum, the residue dissolved in acetonitrile/water, the solution filtered and loaded on a preparative HPLC column. A 1.5% gradient from 100% A to 20% A was used to elute the products. Cyclo-[Tyr-Arg-Phe-Gly] (SEQ ID NO:47) was isolated in 47% yield (1.5 mg, 2.8 10$^{-3}$ mmol): ES-MS: calcd for $C_{26}H_{33}N_7O_5$=523.2 (monoisotopic), exp=523.3.

Evaluating Racemisation

Peptide synthesis: Peptides 1f and 1g were synthesised as described above. Peptide 1f was isolated in 39% yield (from the theoretical substitution value of the resin) ES-MS: calcd for $C_{40}H_{45}N_9O_{12}$=843.3 (monoisotopic), exp=842.9. Peptide 1g was isolated in 28% yield (from the theoretical substitution value of the resin) ES-MS: calcd for $C_{40}H_{45}N_9O_{12}$=843.3 (monoisotopic), exp=843.3. Peptide 1 h was synthesised on Boc-Phe-PAM resin using Boc SPPS protocols as described above, and was isolated in 28% yield (from the theoretical substitution value of the resin) ES-MS: calcd for $C_{40}H_{45}N_9O_{12}$=843.3 (monoisotopic), exp=843.2.

Standard Cyclisation Conditions:
i. Linear peptide at 1 mM in DMF, 1 eq BOP, 2 eq DIEA, 3 h at rt.
ii. Addition of 10 eq of DIEA and 20 h at rt or 1 h at 70° C.

Following this the solvents were removed under vacuum, the residue dissolved in acetonitrile/water and the crude product solutions analysed by ES-MS and HPLC.

Large scale cyclisation of peptide 1f: Peptide 1f (30 mg of the TFA salt, 0.0355 mmol) was dissolved in DMF (30 mL) and 6 eq DIEA (18.3 µL) added. After addition of 1 eq BOP (17.1 mg) the reaction was stirred for 20 h. The solvent was then removed (high vacuum), the residue dissolved in acetonitrile/water and the solution loaded directly onto a preparative HPLC column. A 1.5% gradient from 100% A to 20% A was used to elute the products. The fractions containing cyclic product were collected, combined and lyophilised. 17.5 mg of a mixture of two products was obtained (68% yield): ES-MS: Calcd for $C_{40}H_{43}N_9O_{11}$=825.3 (monoisotopic), Exp=825.1. The mixture of two products (17 mg) was dissolved in DMF (20 mL) and photolysed for 3 hours. The solvent was removed, the residue dissolved in acetonitrile/water and the solution loaded onto a preparative HPLC column. A 1.5% gradient from 100% A to 20% A was used to elute the products. The target cyclic products, cyclo-[Gly-Tyr-Arg-(L)Phe] (SEQ ID NO:48) and cyclo-[Gly-Tyr-Arg-(D)Phe] (SEQ ID NO:48) were isolated as a mixture (3.8 mg, 35% yield): ES-MS: calcd for $C_{26}H_{33}N7O_5$=523.2 (monoisotopic), Exp=523.3. The ratio of L-Phe/D-Phe was determined by chiral amino acid analysis to be 2/3. Of the mixture of two cyclic products, the first eluting one coeluted with the all-L cyclo-[Tyr-Arg-Phe-Gly] 1d (SEQ ID NO:47) synthesised as described above.

Combination of Ring Contraction and Backbone Substitution for the Synthesis of cyclo-[Tyr-Arg-Phe-Ala] (SEQ ID NO:42), Cyclisation at the Tyr-to-Ala Site.

Peptide synthesis: Peptide synthesis and cleavage was performed on Fmoc-Ala-Wang resin (0.45 mmol/gr) as described above. Peptide 4b was isolated in 77% yield (from the theoretical substitution value of the resin): ES-MS: calcd for $C_{41}H_{47}N_9O_{12}$: 857.9, Exp.: 857.4. Peptide 5 was isolated in 28% yield: ES-MS: calcd for $C_{41}H_{47}N_9O_{12}$: 857.9, exp.: 857.4.

Large scale cyclisation of peptide 4: Peptide 4 (60 mg of the TFA salt, 0.062 mmol) was dissolved in DMSO (60 mL) and 1 eq BOP (31.2 mg) added. 2 eq DIEA (24 µL) were added and the reaction stirred at rt for 3 h. 10 eq DIEA (240 µL) were added and stirring continued for another 20 h. The solvent was removed (high vacuum), the residue dissolved in acetonitrile/water and the solution loaded directly onto a preparative HPLC column. A 2% gradient from 95% A to 10% A was used to elute the products. Two cyclic products were separated:

Product A (9 mg, 18%) ES-MS: calcd for $C_{41}H_{45}N_9O_{11}$=839.3 (monoisotopic), exp=839.5. Chiral amino acid analysis of the product showed the presence of L-Tyr, L-Arg, L-Phe and D-Ala. Product A=cyclo-[(Hnb)Tyr-Arg-(Hnb)Phe-(D)Ala] SEQ ID NO:44). Product B (7 mg, 13%) ES-MS: calcd for $C_{41}H_{45}N_9O_{11}$=839.3 (monoisotopic), exp=839.5. Chiral amino acid analysis showed the presence of L-Tyr, L-Arg, L-Phe and L-Ala. Product B=cyclo-[(Hnb)Tyr-Arg-(Hnb)Phe-Ala] (SEQ ID NO:44). Another 8 mg of a mixture of products A and B (15%) was isolated, giving a total cyclisation yield of 46%.

Photolysis of cyclo-[(Hnb)Tyr-Arg-(Hnb)Phe-(D)Ala] (SEQ ID NO:44): Product A (9 mg) was dissolved in DMF (100 mL) and photolysis carried out for 3 h. The solvent was removed, the residue dissolved in acetonitrile/water and the solution loaded onto a preparative HPLC column. A 1.5% gradient from 95% A to 10% A was used to elute the products. The cyclic product, cyclo-[Tyr-Arg-Phe-(D)Ala] (SEQ ID NO:42) was isolated (2.4 mg, 42% yield): ES-MS: calcd for $C_{27}H_{35}N_7O_5$=537.61 (monoisotopic), exp=537.2. Chiral amino acid analysis of this product showed presence of L-Tyr, L-Arg, L-Phe and D-ALa.

Large scale cyclisation of peptide 4: Peptide 4 (30 mg of the TFA salt, 0.031 mmol) was dissolved in DMF (35 mL) and 1 eq BOP (15.5 mg) added. 3 eq DIEA (18.2 µL) were added and the reaction stirred at rt for 3 h. 10 eq DIEA (61 µL) were added and stirring continued for another 20 h. The solvent was removed (high vacuum), the residue dissolved in acetonitrile/water and the solution loaded directly onto a preparative HPLC column. A 2%/min gradient from 95% A to 10% A was used to elute the products. One cyclic product was separated:

Cyclo-[(Hnb)Tyr-Arg-(Hnb)Phe-Ala] (SEQ ID NO:44): (15.6 mg, 60%) ES-MS: calcd for $C_{41}H_{45}N_9O_{11}$=839.3 (monoisotopic), exp=839.2.

EXAMPLE 4

Activated Linkers

Activated linkers of the general formula

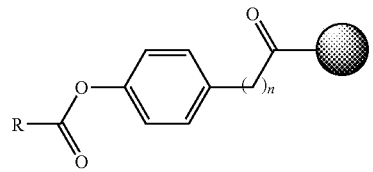

n = 0-2 have been evaluated for their stability during chain assembly and their lability in the final cyclisation reaction. For the n=0 linker we have synthesised a series of constrained cyclic peptides, as illustrated in Table 5 below.

A general outline of the procedure used is shown in Scheme 9. The hydroxybenzoic acid (1) was acylated with Boc-Gly-OH. The resulting ester link was found to be stable to TFA treatment, as confirmed by treating compound (2) with TFA and subsequent 1H NMR analysis of the products (3).

Scheme 9

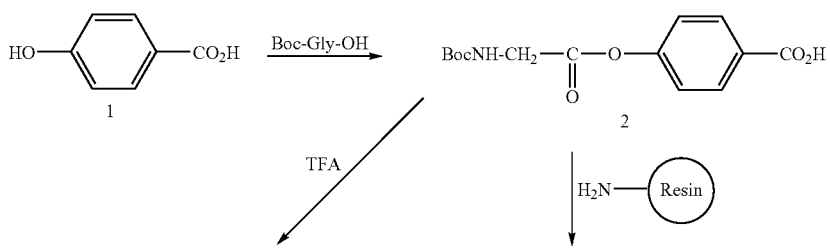

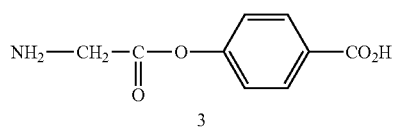

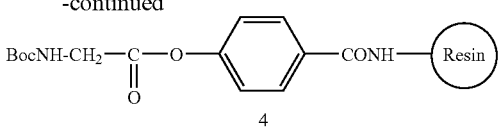

-continued

3

4

↓ SPPS

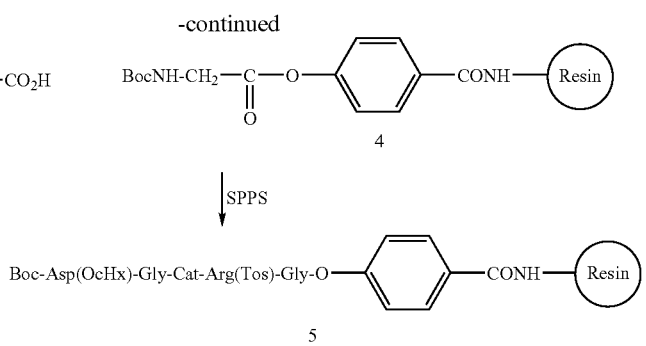

5

↓ HF/anisol

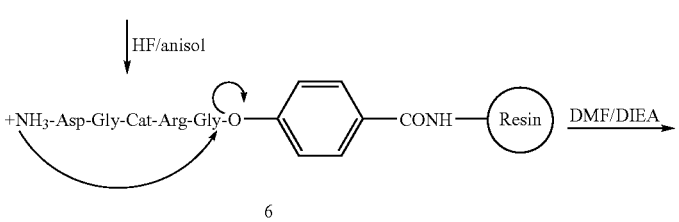

6

'Cyclisation by Cleavage' Experiments

Compound (2) was attached to amino-methylated resin (polystyrene) (substitution value (sv)=0.21 mmol/g) using HBTU in DMF (Scheme 9). Peptide assembly was monitored by quantitative ninhydrin tests, and indicated successful assembly of the linear sequence. This was confirmed by the increase in resin weight. The deprotection of the side chain protecting group was achieved by treatment with HF/anisole (9/1) at −5° C. for 1 hour. After HF evaporation, the resin was washed with ether.

Cyclisation and accompanying cleavage was achieved by treatment with 10 equivalents DIEA in DMF for 3 days. The reaction mixture was worked up by filtration and the filtrate diluted with water and lyophilised. The crude lyophilised product was redissolved in acetonitrile/water (1/1) and further analysed by analytical and preparative HPLC.

The HPLC profile of the crude product is shown in FIG. 1. The major component is the target peptide, as is evidenced by HPLC comparison and a coelution experiment with solution phase synthesised material. This result illustrates the potential power of this strategy in synthesising constrained cyclic peptides, particularly when considering the surprising purity of the crude material. The yields of cyclic material are given in Table 5.

TABLE 5

Yields of Cyclic Peptide Using Activated Linker

| [Linear] tetrapeptide | Yield of Cyclisation |
|---|---|
| cyclo-[DG-Act-RG] (SEQ ID NO:1) | 11% |
| cyclo-[DG-Amb-RG] (SEQ ID NO:50) | 7%; 3% dimer |
| cyclo-[D-Amb-GRG] (SEQ ID NO:51) | 5% monomer; 5% dimer |

Experimental to Example 4

This section describes the experimental details for the synthesis of the activated linker and model peptides. Linear DG-Act-RG is SEQ ID NO:49.

Synthesis of Model Compounds Using Activated Linkers Cyclo [DGActRG] (Table 5)

Cat is 3-carboxy-4-aminothiophene, which is alternatively known as Act (3-amino-4-carboxythiophene). Amb is 3-aminobenzoic acid.

Linker Resin

The aminomethylated resin (2.38 gr, 0.5 mmole) was first washed with 10% DIEA in DMF (5 min) and then washed with DMF (3×5 ml). Hydroxybenzoic acid (276 mg, 2 mmole) was dissolved in 4 ml 0.5M HBTU in DMF and DIEA (400 μL, 2.3 mmol) added. The activated solution was then added to the neutralised resin. After 10 min the resin was drained and washed with DMF (3×5 mL). A solution of aquous sodium hydroxide (1M, 2 mL) in DMF (4 mL) was added to the resin and mixed for 10 minutes. The sodium hydroxide treatment was repeated, and the resin washed with DMF/water (1/1) (3×5 mL) and then with DMF (3×5 mL).

Assembly of the Peptide

Boc-glycine was first coupled to the linker as follows. BocGlycine (350 mg, 2 mmole) was dissolved in 2 mL DCM and DIC (156 μL, 1 mmole) added. After 15 min the solution was diluted with 2 mL DMF, and added to the resin with DIEA (400 μL, 2.3 mmole). After 30 min, the resin was drained and washed with DMF (3×5 mL). The Boc group was then removed using neat TFA (2×1 min). The next residues were coupled using the following in situ neutralisation protocol: 2 mmole of the Boc-protected amino acid was dissolved in 4 mL of an 0.5M HBTU solution in DMF, and activated through addition of DIEA (460 μL, 2.6 mmole). The activated solution was then added to the resin and mixed for 10 minutes. The resin was drained and washed with DMF. Neat TFA (2×1 min) was used again for deprotection of the N-terminus. The following residues were coupled in series: Boc-Arg(Mts)OH, Boc-Gly-Cat-OH, Boc-Asp(OcHx)-OH.

Side-Chain Deprotection

After assembly the N-terminal Boc-group was removed with TFA as above, and the resin dried. The side chains were removed using HF treatment as follows: 1 gr of resin was mixed with 1 mL thioanisole and 9 mL of HF were added. The mixture was stirred at −5° C. for 1 hour and the HF removed under reduced pressure. The resin was washed with diethylether (3×20 mL) and dried.

Cyclisation

The resin was stirred in DMF (10 mL) containing DIEA (100 μL) for 12 hours. The resin was filtered off and the DMF removed in vacuo. The residue was dissolved in a minimal amount acetonitrile/water (1/1) and loaded directly on a preparative reverse phase column for HPLC separation of the product. Cyclo-[DGCatRG] (SEQ ID NO:1) (27 mg, 11% yield from the starting resin) was obtained.

The same protocols were followed to assemble, deprotect and cyclise the following peptides: cyclo-[DGAmbRG] (SEQ ID NO:50): 7.6% yield (3% dimer); cyclo-[DAmbGRG] (SEQ ID NO:51): 5% yield (5% dimer).

EXAMPLE 5

Safety Catch Linkers

We have also evaluated the safety catch linkers of the general class

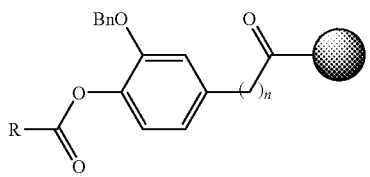

n = 0-2

Examples of Safety Catch Linker's

Activation of this linker is achieved by removal of the benzyl group. The safety-catch linker (n=2) was synthesised as shown in Scheme 10.

We have found that better results are obtained when n is 1 or 2, and therefore safety catch linkers of this type are preferred.

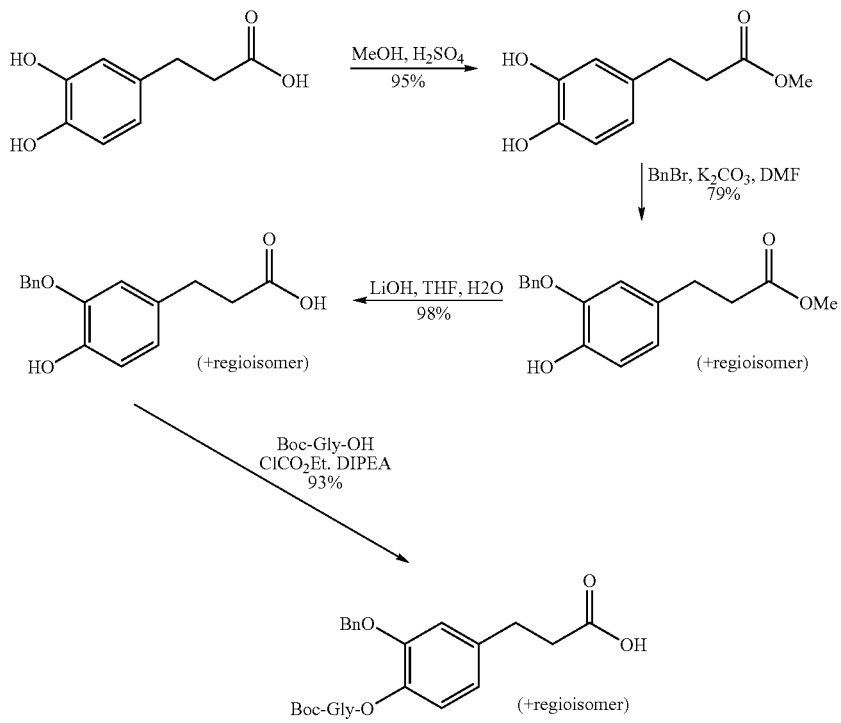

Scheme 10

Synthesis of Safety Catch Linker

Figure 2:
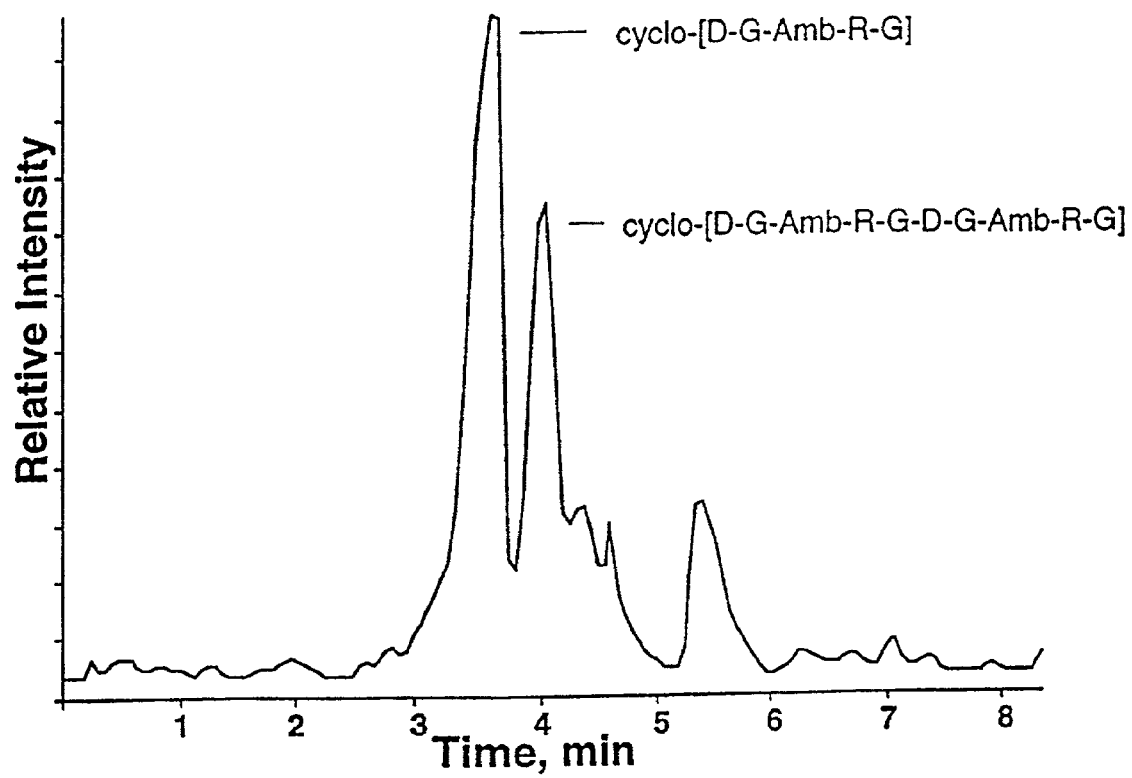
FIG. 2 shows an LC-MS profile of the crude filtrate obtained after HF cleavage and base cyclisation of a cyclic peptide synthesised using a safety catch linker of n=2. Cyclo-[D-G-Amb-R-G] is SEQ ID NO:50 and cyclo-[D-G-Amb-R-G-D-G-Amb-R-G] is SEQ ID NO:52.

This safety-catch linker was attached to aminomethylated polystyrene using HBTU/DIPEA in DMF, then peptide assembly was accomplished using standard Boc protocols. Treatment of the resin with anhydrous HF in the presence of anisole as a scavenger at −5° C. resulted in deprotection of the amino-acid side-chains, with concomitant removal of the benzyl group of the linker. The HF was evaporated and the resin was washed with diethyl ether to remove scavenger. Treatment of the resin with DIPEA in DMF for 48 h gave the crude cyclised product. An LC-MS profile of the crude cyclic material is shown in FIG. 2. The major component is the desired cycle, and an appreciable amount of the cyclodimer is also present. Preparative-scale HPLC gave a mixture of the monomer and dimer, in an overall yield of approximately 50%.

Experimental to Example 5

This section describes the synthesis of one type of safety catch linker and model peptides.

Synthesis of Model Compounds Using Safety Catch Linkers

Benzyl 4-Benzyloxy-3-hydroxybenzoate

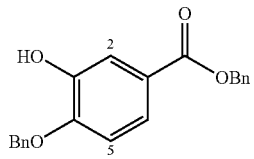

Benzyl bromide (1.50 cm$^3$, 2.16 g, 12.6 mmol) was added to a stirred suspension of 3,4-dihydroxybenzoic acid (1.00 g, 6.49 mmol), potassium carbonate (1.97 g, 14.3 mmol) and a catalytic amount of tetrabutylammonium iodide in N,N-dimethylformamide (50 cm$^3$). The suspension was stirred under nitrogen overnight then water (500 cm$^3$) and 5% hydrochloric acid (50 cm$^3$) were added, and the mixture was extracted with diethyl ether (3×100 cm$^3$). The combined extracts were washed with water (3×100 cm$^3$) and brine (100 cm$^3$), then dried (Na$_2$SO$_4$) and evaporated to an orange oil. Flash column chromatography (eluent: 10-20% ethyl acetate in light petroleum) gave first benzyl 3,4-dibenzyloxybenzoate (168 mg, 6%), identical to that prepared above. Further elution then gave benzyl 4-benzyloxy-3-hydroxybenzoate (1.312 g, 60%) as a pale yellow oil. The position of the benzyloxy group was deduced from an n.O.e. observed between the proton at position 5 and the methylene protons of the benzyloxy group at position 4.

$R_f$ 0.18 (20% EtOAc in light petroleum).
$\nu_{max}$ (thin film, NaCl) 3600-3200, 1715, 1615, 1590 cm$^{-1}$.
$^1$H NMR (300 Hz, CDCl$_3$) 5.17, 2H, s, CH$_2$; 5.34, 2H, s, CH$_2$; 5.73, 1H, bs, OH; 6.95, 1H, d (J 8.2). H5; 7.32-7.46, 10H, Ar—H, 7.65, 1H, dd (J 2.0, 10.6), H6; 7.66, 1H, s, H2; OH not observed.
$^{13}$C NMR (75 MHz, CDCl$_3$) δ6.5, CH$_2$; 71.1, CH$_2$; 111.2, 115.9, 122.9, 123.6, 127.8, 128.0, 128.1, 128.2, 128.5, 128.6, 128.8, 135.5, 136.2, 145.4, 149.6, 166.0, CO$_2$.
Mass spectrum: 335 (MH$^+$).
Found: δ 334.1205; C$_{21}$H$_{19}$O$_4$ requires M$^+$ 334.1205.

4-Benzyloxy-3-hydroxybenzoic Acid

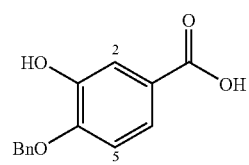

A solution of lithium hydroxide hydrate (300 mg, 7.15 mmol) in water (15 cm$^3$) was added dropwise to a stirred solution of benzyl 4-benzyloxy-3-hydroxybenzoate (1.177 g, 3.52 mmol) in tetrahydrofuran (35 cm$^3$). The resulting emulsion was stirred overnight, by which time a clear, pale yellow solution had formed. More lithium hydroxide hydrate (300 mg, 7.15 mmol), water (25 cm$^3$) and tetrahydrofuran (25 cm$^3$) were added, and stirring was continued for 24 h. The tetrahydrofuran was removed under reduced pressure. Water (100 cm$^3$) was added to the residual mixture, which was washed with diethyl ether (2×50 cm$^3$), acidified to pH 1 with 5% HCl and extracted with dichloromethane (3×100 cm$^3$). The combined extracts were washed with brine (50 cm$^3$), dried (NaSO$_4$) and evaporated to give 4-benzyloxy-3-hydroxybenzoic acid as a white solid (638 mg, 74%). The diethyl ether washings were extracted with 1 M potassium hydroxide (2×25 cm$^3$). The combined extracts were acidified to pH 1 with 5% HCl and extracted with dichloromethane (3×100 cm$^3$). The combined extracts were dried over MgSO$_4$ and evaporated to give a further 119 mg of product (total yield 757 mg, 88%), m.p. 163-165° C.

$\nu_{nax}$ (KBr disc) 3555, 3200-2400, 1676, 1619, 1592 cm$^{-1}$.
$^1$H NMR (300 Hz, CDCl$_3$) 5.19, 2H, s, CH$_2$; 5.71, 1H, br s, OH; 6.98, 1H, d (J 9.0), H5; 7.38-7.45, 5H, Ar—H, 7.67, 1H, dd (J 8.9, 2.1), H6; 7.68, 1H, d (J 2.0), H2; CO$_2$H not observed.
$^{13}$C NMR (75 MHz, CDCl$_3$) 71.2, CH$_2$; 111.2, 116.3, 122.6, 123.5, 127.9, 128.7, 128.9, 135.4, 145.5, 150.2, 170.6, CO$_2$.
Mass spectrum: 245 (MH$^+$)
Found: H, 244.0740; C$_{14}$H$_{12}$O$_4$ requires M$^+$ 244.0736.

Allylation of 3,4-Dihydroxybenzoic Acid: Preparation of Propen-2-yl 3,4-Bis(propen-2-yloxy)benzoate, Propen-2-yl 3-hydroxy-4-(propen-2-yloxy)benzoate and Propen-2-yl 3,4-dihydroxybenzoate

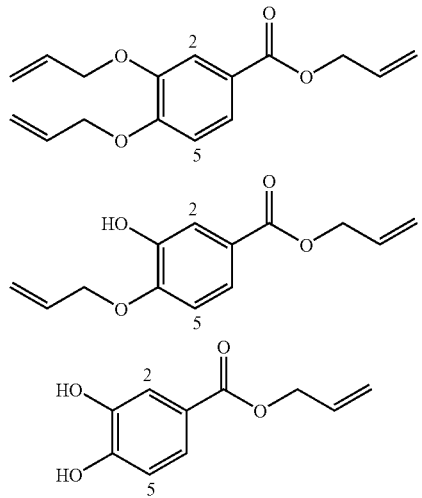

Allyl bromide (1.18 cm$^3$, 1.65 g, 13.6 mmol) was added to a stirred suspension of 3,4-dihydroxybenzoic acid (1.00 g, 6.49 mmol) and potassium carbonate (1.97 g, 14.3 mmol) in dry N,N-dimethylformamide (50 cm$^3$). After stirring overnight under an atmosphere of nitrogen, the mixture was poured into water (500 cm$^3$), acidified with 5% hydrochloric acid and extracted with ethyl acetate (3×100 cm$^3$). The combined extracts were washed with water (3×100 cm$^3$) and brine (50 cm$^3$), then dried over MgSO$_4$ and evaporated to a brown oil which was purified by flash column chromatography (eluent: 10-50% ethyl acetate in light petroleum). The first compound to elute was propen-2-yl 3,4-bis(propen-2-yloxy)benzoate as a pale yellow oil (460 mg, 26%).

$R_f$ 0.43 (20% EtOAc in light petroleum).
$\nu_{max}$ (thin film, NaCl) 1718, 1648, 1600, 1270 cm$^{-1}$.
$^1$H NMR (300 Hz, CDCl$_3$) 4.64, 2H, dt (J 1.6, 5.2), OCH$_2$; 4.66, 2H, dt (J 1.7, 5.1), OCH$_2$; 4.79, 2H, dt (J 1.5, 5.7), OCH$_2$; 5.24-5.47, 6H, m, 3x=CH$_2$; 5.97-6.15, 3H, m, 3x=CH; 6.88, 1H, d (J 8.5), H5; 7.58, 1H, d (J 2.0), H2; 7.67, 1H, dd (J 2.0, 8.4), H6.

$^{13}$C NMR (75 MHz, CDCl$_3$) δ 5.3, 69.6 and 69.8, 3x CH$_2$O; 112.3 and 114.6, C2 and C5; 117.9, 117.9 and 118.0, 3x=CH$_2$; 122.7, C1; 123.7, C6; 132.4, 132.6 and 132.9, 3x CH=CH$_2$; 147.9, C3; 152.5, C4; 165.9, C=O.

Mass spectrum: 275 (MH$^+$), 217 (MH—C$_3$H$_5$O)

Found: M 274.1204; C$_{16}$H$_{18}$O$_4$ requires M$^+$ 274.1205.

Next to elute was propen-2-yl 3-hydroxy-4-(propen-2-yloxy)benzoate as a pale pink oil (782 mg, 51%).

R$_f$ 0.26 (20% EtOAc in light petroleum).

$v_{max}$ (thin film, NaCl) 3422 br, 1718, 1616, 1590, 1508 cm$^{-1}$.

$^1$H NMR (300 Hz, CDCl$_3$) 4.67, 2H, dt (J 5.5, 1.4), OCH$_2$; 4.79, 2H, dt (J 5.5, 1.5), OCH$_2$; 5.25-5.45, 4H, m, 2x=CH$_2$; 5.70, 1H, s, OH; 5.96-6.12, 2H, m, 2xCH=CH$_2$; 6.87, 1H, d (J 8.7), H5; 7.62, 1H, dd (J 7.7, 2.2), H6; 7.63, 1H, br s, H2.

$^{13}$C NMR (75 MHz, CDCl$_3$) δ 5.4, OCH$_2$; 69.8, OCH$_2$; 111.1 and 115.8, C2 and C5; 118.0 and 119.0, 2x=CH$_2$; 122.7, C6; 123.5, C1; 132.1 and 132.4, 2x=CH; 145.4, C3; 149.4, C4; 165.9, C=O.

Mass spectrum: 235 (MH$^+$), 177 (MH—C$_3$H$_5$O), 149 (MH—C$_4$H$_5$O$_2$)

Found: M 234.0892; C$_{13}$H$_{14}$O$_4$ requires M$^+$ 234.0892.

Last to elute was propen-2-yl 3,4-dihydroxy-benzoate as a pale yellow semi-solid (80.2 mg, 6%).

R$_f$ 0.30 (50% EtOAc in light petroleum).

$v_{max}$ (KBr disc) 3468br, 3344br, 1693, 1613, 1445, 1300 cm$^{-1}$.

$^1$H NMR (300 Hz, CDCl$_3$) 4.78, 2H, d (J 5.4), OCH$_2$; 5.27, 1H, br d (J 10.5), =CHH; 5.39, 1H, br d (J 18.6), =CHH; 5.94-6.07, 1H, m, CH=CH$_2$; 6.90, 1H, d (J 7.8), H5; 7.56, 1H, d (J 7.8), H6; 7.64, 1H, br s, H2; OHs not observed.

$^{13}$C NMR (75 MHz, CDCl$_3$) 65.7, OCH$_2$; 114.8 and 116.3, C2 and C5; 118.3, =CH$_2$; 122.1, C1; 123.7, C6; 132.1, =CH; 143.3, C3; 149.2, C4; 166.9, C=O.

Mass spectrum: 195 (MH$^+$)

Found: M 194.0578; C$_{10}$H$_{10}$O$_4$ requires M$^+$ 194.0579.

Propen-2-yl 3-Benzyloxy-4-(propen-2-yloxy)benzoate

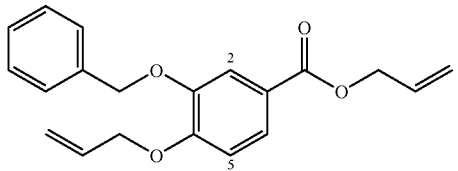

Benzyl bromide (0.440 cm$^3$, 634 mg, 3.70 mmol) was added to a stirred mixture of propeny-2-yl 3-hydroxy-4-(propen-2-yloxy)benzoate (782 mg, 3.34 mmol) and potassium carbonate (553 mg, 4.00 mmol) in N,N-dimethylformamide (30 cm$^3$). The mixture was stirred under nitrogen overnight, then poured into water (300 cm$^3$) and extracted with ethyl acetate (3×100 cm$^3$). The combined extracts were washed with water (3×50 cm$^3$) and brine (50 cm$^3$), then dried over MgSO$_4$ and evaporated to a colourless oil. This was dissolved in dichloromethane and filtered through a plug of silica. Evaporation of the filtrate gave propen-2-yl 3-benzyloxy-4-(propen-2-yloxy)benzoate as a colourless oil (1.096 mg, 100%).

R$_f$ 0.42 (20% EtOAc in light petroleum)

$v_{max}$ (thin film, NaCl) 1714, 1600, 1514, 1428 cm$^{-1}$.

$^1$H NMR (300 Hz, CDCl$_3$) 4.67, 2H, dt (J 5.2, 1.6), =CH—CH$_2$; 4.79, 2H, dt (J 5.6, 1.5), =CH—CH$_2$; 5.19, 2H, s, PhCH$_2$; 5.29, 2H, ddt (J 10.2, 2.8, 1.5), =CH$_2$; 5.41, 2H, ddt (J 17.2, 3.1, 1.6), =CH$_2$; 5.96-6.15, 2H, m, 2x=CH; 6.91, 1H, d (J 8.5), H5; 7.30-7.49, 5H, PhCH$_2$; 7.66, 1H, d (J 2.0), H2; 7.69, 1H, dd (J 8.4, 2.0), H6.

$^{13}$C NMR (75 MHz, CDCl$_3$) 66.3, 69.6 and 71.0, 3x CH$_2$O; 112.5 and 115.2, 2x=CH; 117.9, 2x=CH$_2$; 122.7, C1; 127.3, 127.9, 128.5, 132.4 and 132.6, 5x CH; 136.7; 148.0 and 152.7, C3 and C4; 165.9, C=O.

Mass spectrum: 325 (MH$^+$).

Found: M 324.1361; C$_{20}$H$_{20}$O$_4$ requires M$^+$ 324.1362.

3-Benzyloxy-4-Hydroxybenzoic Acid

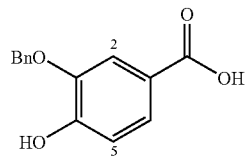

A mixture of propen-2-yl 3-benzyloxy-4-(propen-2-yloxy)benzoate (1.0356 g, 3.19 mmol), tris(triphenyl-phosphine)rhodium chloride[1] (204 mg, 0.22 mmol) and 1,4-diazabicyclo[2.2.2]octane (74 mg, 0.66 mmol) in ethanol (18 cm$^3$) and water (2 cm$^3$) was heated under reflux under an atmosphere of nitrogen for 16 h. The cooled mixture was poured into 1 M hydrochloric acid (100 cm$^3$), stirred for 60 min, then extracted with dichloromethane (3×100 cm$^3$). The combined extracts were dried over MgSO$_4$ and evaporated to an orange solid which was purified by flash column chromatography (eluent: 1:1 EtOAc:light petroleum) to give 3-benzyloxy-4-hydroxybenzoic acid as an orange solid (650 mg, 83%), m.p. 167.2-171.3° C.

R$_f$ 0.25 (50% EtOAc in light petroleum).

$v_{max}$ (KBr disc) 3528, 3200-2600, 1700, 1673, 1611 cm$^{-1}$.

$^1$H NMR (300 Hz, CDCl$_3$) 5.18, 2H, s, CH$_2$; 6.13, 1H, br s, OH; 7.00, 1H, d (J 8.3), H5; 7.37-7.50, 5H, m, Bn—H, 7.71, 1H, d (J 1.9), H2; 7.75, 1H, dd (J 1.9, 8.3), H6; CO$_2$H not observed.

$^{13}$C NMR (75 MHz, CDCl$_3$) 71.4, CH$_2$; 113.5, 114.4, 121.2, 125.5, 128.1, 128.7, 128.8, 135.6, C1; 145.4 and 151.0, C3 and C4; 171.0, C=O Mass spectrum: 245 (MH$^+$)

Found: M 244.0731; C$_{14}$H$_{12}$O$_4$ requires M$^+$ 244.0736.

1. Corey, E. J. and Suggs, J. W., J. Org. Chem., 1973 38 3224.

Benzyl 3-(tert-Butyldimethylsilyloxy)-4-benzyloxybenzoate

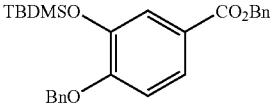

A solution of tert-butyldimethylsilyl chloride (579 mg, 3.84 mmol) in dichloromethane (10 cm$^3$) was added to a stirred solution of benzyl 4-benzyloxy-3-hydroxy-benzoate (642.3 mg, 1.92 mmol) and imidazole (327 mg, 4.80 mmol) in dichloromethane (15 cm$^3$). A thick precipitate formed immediately. After 1 h the mixture was poured into water (50 cm$^3$). The layers were shaken and separated and then the aqueous phase was further extracted with dichloromethane (2×50 cm³). The combined extracts were washed with brine (50 cm³) then dried (Na₂SO₄) and evaporated to a pale yellow oil. This was taken up in 20% ethyl acetate in petroleum ether and filtered through a plug of silica. Evaporation of the filtrate gave the title compound as a pale yellow oil (936 mg) which was used immediately for the next step.

R$_f$ 0.49 (20% EtOAc in hexane).

$v_{max}$ (NaCl film) 1718, 1599, 1509, 1427, 1290, 1213, 837 cm⁻¹.

¹H NMR (300 Hz, CDCl₃) 0.11, 6H, s, SiMe₂; 0.96, 9H, s, Cme₃; 5.10, 2H, s, CH; 5.33, 2H, s, CH₂; 6.92, 1H, d (J 8.7), H5; 7.31-7.45, 10H, 10xBn—H, 7.59, 1H, d (J 1.5), H2; 7.67, 1H, dd (J 2.2, 8.9), H6.

¹³C NMR (75 MHz, CDCl₃)-4.6, SiMe₂; 18.4, CMe₃; 25.6, CMe₃; 66.4 and 70.7, 2xCH₂; 112.5, 122.2, 124.3, 127.8, 127.9, 128.1, 128.2, 128.3, 128.5, 136.2, 136.4, 144.9, 154.5, Ar—C, 166.1; C=O.

3-(tert-Butyldimethylsilyloxy)-4-hydroxybenzoic Acid

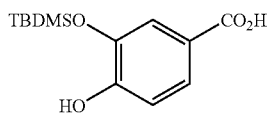

A solution of the crude silyl ether (936 mg, 2.09 mmol) in ethanol (50 cm⁻¹) containing 10% palladium-on-carbon (80 mg) was shaken under an atmosphere of hydrogen at 25 p.s.i. for 48 h. The mixture was filtered through celite and evaporated, then the residue was taken up in ethyl acetate and filtered through a plug of silica to give the title compound as a pale green oil (424 mg, 76%).

$v_{max}$ (NaCl film) 3516, 3400-2600, 1682, 1597, 1298 cm⁻¹.

¹H NMR (300 Hz, CDCl₃) 0.33, 6H, s, SiMe₂; 1.04, 9H, s, CMe₃; 6.05, 1H, brs, OH; 6.99, 1H, d (J 8.4), H5; 7.60, 1H, d (J 2.1), H2; 7.73, 1H, dd (J 1.9, 8.5), H6.

¹³C NMR (75 MHz, CDCl₃) -4.4, SiMe₂; 18.2, CMe₃; 25.6, CMe₃; 114.6, 119.3, 121.3, 125.5, 142.1, 152.5, 6xArC; 171.9, C=O.

Benzyl 4-benzyloxy-3-(tert-Butyldiphenylsilyloxy)benzoate

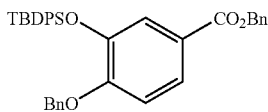

A solution of tert-butyldiphenylsilyl chloride (850 mg, 3.09 mmol) in dichloromethane (10 cm³+5 cm³ rinse) was added to a stirred solution of benzyl 4-benzyloxy-3-hydroxybenzoate (827 mg, 2.47 mmol) and imidazole (421 mg, 6.18 mmol) in dichloromethane (15 cm³). After a few minutes a precipitate formed. The mixture was stirred overnight under an atmosphere of nitrogen, then was poured into water (50 cm³) The layers were shaken and separated, then the aqueous phase was further extracted with dichloromethane (2×50 cm³). The combined extracts were washed with brine (50 cm³) and evaporated to a pale yellow oil. This was filtered through a short silica column and eluted with 20% ethyl acetate in petroleum ether. Evaporation of the filtrate gave benzyl 3-(tert-butyldiphenylsilyloxy)-4-benzyloxybenzoate (1.646 g) as a very pale yellow oil, containing some tert-butyldiphenyl-silanol, which was used directly for the next step.

R$_f$ 0.37 (20% EtOAc in hexane).

$v_{max}$ (NaCl, thin film) 1715, 1599, 1510, 1427, 1291 cm⁻¹.

¹H NMR (300 Hz, CDCl₃) 1.13, 9H, s, CMe₃; 4.93, 2H, s, CH₂O; 5.25, 2H, s, CH₂O; 6.84, 1H, d (J 8.9), H5; 7.21-7.43, 16H, m, 16xAr—H, 7.55, 1H, d (J 2.1), H2; 7.63, 1H, dd (J 2.1, 8.4), H6; 7.70-7.79, 4H, m, 4xAr—H.

¹³C NMR (75 MHz, CDCl₃) 19.7, CMe₃; 26.6, CMe₃; 66.2 and 70.3, 2xCH₂O; 112.4, 121.4, 122.6, 124.1, 127.4, 127.5, 127.7, 127.8, 127.9, 128.3, 128.4, 129.7, 133.1, 134.8, 135.3, 136.2, 144.7 and 153.8, 18xAr—C, 165.9; C=O.

Synthesis of Model Compounds Using Safety Catch Linker.

Methyl 3-(3,4-Dihydroxyphenyl)Propionate

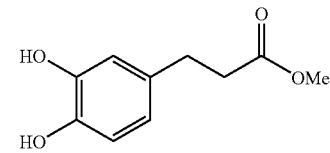

A solution of 3-(3,4-dihydroxyphenyl)propionic acid (1.00 g, 5.49 mmol) and concentrated H₂SO₄ (10 drops) in methanol (25 cm³) was heated under reflux overnight. The solvent was evaporated and the residue was shaken with water (50 cm³) and extracted into CHCl₃ (3×50 cm³). The combined extracts were dried (Na₂SO₄) and evaporated to gave the methyl ester a pale yellow oil which crystallised on standing (1.12 g, 100%), m.p. 71.9-74.1° C. (lit. ¹m.p. 74-76° C.)

n$_{max}$ (KBr disc) 3485, 3311, 1712 cm⁻¹.

¹H NMR (300 Hz, CDCl₃) 2.61, 2H, t (J 7.5), CH₂CO₂; 2.83, 2H, t (J 7.6), ArCH₂; 3.69, 3H, s, OMe; 5.40, 2H, br s, 2xOH; 6.61, 1H, dd (J 2.1, 8.1), H6; 6.71, 1H, d (J 2.0), H2; 6.77, 1H, d (J 8.1), H5.

¹³C NMR (75 MHz, CDCl₃) 30.2 and 35.9, 2xCH₂; 51.9, OMe; 115.4, C2 and C6; 120.5, C5; 133.2, C1; 142.1 and 143.6, C3 and C4; 174.3, C=O.

Mass spectrum: (MH⁺)

Found: M 196.0739; C₁₀H₁₂O₄ requires M⁺ 196.0736. Freudenberg and Heel, (1953)

Methyl 3-(3-Benzyloxy-4-hydroxyphenyl)Propionate and Methyl 3-(4-Benzyloxy-3-hydroxyphenyl)Propionate

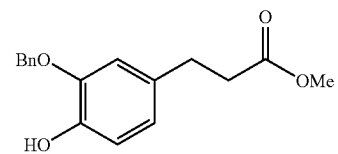

-continued

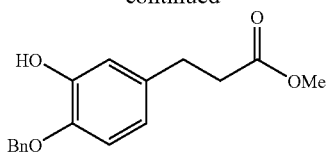

Benzyl bromide (0.606 cm³, 872 mg, 5.20 mmol) was added to a stirred suspension of methyl 3-(3,4-dihydroxyphenyl)propionate (1.000 g, 5.10 mmol), K₂CO₃ (845 mg, 6.12 mmol) and a catalytic amount of tetrabutylammonium iodide in DMF (25 cm³). The suspension was stirred overnight under an atmosphere of nitrogen. Water (500 cm³) and 5% HCl (50 cm³) were added, and the mixture was extracted with diethyl ether (3×100 cm³). The combined extracts were washed with water (3×100 cm³) and brine (100 cm³), then dried (Na₂SO₄) and evaporated to a brown oil which was purified by flash chromatography (5-20% EtOAc in petrol) to give a 1:1 mixture of the monobenzyl ethers as a colourless oil (1.150 g, 79%)

$n_{max}$ (NaCl thin film) 3446, 1732, 1592, 1514 cm⁻¹.

¹H NMR (300 Hz, CDCl₃) 2.60, 4H, t (J 7.4), 2xCH₂CO₂; 2.87, 2H, t (J 7.8), CH₂CH₂CO₂; 2.89, 2H, t (J 7.7), CH₂CH₂CO₂; 3.67, 3H, s, OMe; 3.68, 3H, s, OMe; 5.08, 2H, PhCH₂; 5.09, 2H, PhCH₂; 6.67, 1H, dd (J 8.2, 2.1), H6; 6.73, 1H, dd (J 8.0, 1.6), H6; 6.81, 2H, br s, H2.2; 6.82, 1H, d (J 8.0), H5; 6.88, 1H, d (J 8.2), H5; 7.30-7.50, 10H, Ar—H.

¹³C NMR (75 MHz, CDCl₃) 30.3, 30.6, 35.7 and 36.0, 2xCH₂CH₂; 51.5, 2xOMe; 71.0 and 71.1, PhCH₂; 112.2, 112.4, 114.6 and 114.7, C2 and C6; 119.6 and 121.2, C5; 127.2, 127.3, 127.7, 127.8, 128.2, 128.3, 128.4 and 128.6, Bn—C, 132.4 and 134.2, C1; 144.2, 145.6 and 145.8, C3 and C4; 173.3, CO₂.

3-(3-Benzyloxy-4-hydroxyphenyl)Propionic Acid and 3-(4-Benzyloxy-3-hydroxyphenyl)Propionic Acid A solution of lithium hydroxide monohydrate (5.25 g, 125 mmol) in water (150 cm³) was added to a stirred solution of the mixture of methyl esters (11.95 g, 41.7 mmol) in THF (150 cm³). The resulting mixture was stirred under an atmosphere of nitrogen. Next morning a clear, pale yellow solution had formed. The THF was evaporated and the residue was diluted with water (150 cm³ and acidified to pH 3 with 5% HCl. The mixture was extracted with CHCl₃ (3×350 cm³) and the combined extracts were dried (Na₂SO₄) and evaporated to a brown oil which solidified on standing. This was taken up in EtOAc and passed through a short silica column. Evaporation of the eluent gave the product as a tan solid (11.12 g, 98%).

$n_{max}$ (KBr disc) 3533, 3471, 3300-2600, 1718, 1699, 1515 cm⁻¹.

¹H NMR (300 Hz, CDCl₃) 2.66, 4H, t (J 7.6), CH₂CO₂; 2.90, 2H, t (J 7.6), CH₂CH₂CO₂; 2.91, 2H, t (J 7.7), CH₂CH₂CO₂; 5.09, 2H, s, PhCH₂; 5.10, 2H, s, PhCH₂; 6.69, 1H, dd (J 8.3, 2.1), H6; 6.75, 1H, dd (J 8.1, 2.0), H6; 6.83, 1H, d (J 1.9), H2; 6.84, 1H, d (J 2.0), H2; 6.87, 1H, d (J 8.4), H5; 6.90, 1H, d (J 8.2), H5; 7.30-7.50, 10H, m, Ar—H; CO₂H not observed.

¹³C NMR (75 MHz, CDCl₃) 29.9, 30.2, 35.7 and 35.9, 2xCH₂CH₂; 71.1 and 71.2, PhCH₂; 112.3, 112.4, 114.6 and 114.7, C2 and C6; 119.6 and 121.2, C5; 127.2, 127.3, 127.7, 127.8, 128.3, 128.4 and 128.7, Bn—C, 132.0 and 136.2, C1; 144.3, 145.6 and 145.8, C3 and C4; 179.2, CO₂.

3-(3-Benzyloxy-4-(N-tert-Butoxycarbonyl)glycyloxy)Phenyl-propionic Acid and 3-(4-Benzyloxy-3-(N-tert-Butoxycarbonyl)glycyloxy)Phenyl Propionic Acid

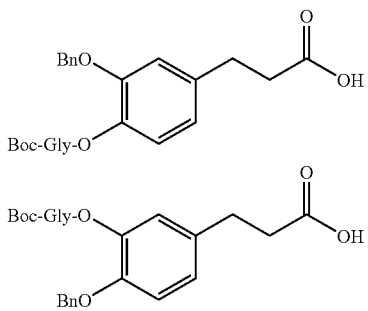

Triethylamine (1.40 cm³, 1.01 g, 10.0 mmol) and ethyl chloroformate (0.960 cm³, 1.085 g. 10.0 mmol) were added to a stirred, chilled (−20° C.) solution of Boc-Gly-OH (1.75 g, 10.0 mmol) in dichloromethane (20 cm³). The solution was stirred for 20 min at −10--15° C. during which time a precipitate formed. A solution of regioisomeric mixture of benzyloxyacids (2.86 g, 10.0 mmol) and triethylamine (1.40 cm³, 1.01 g, 10.0 mmol) in dichloromethane (20 cm³+5 cm³ rinse) was then added dropwise. The resulting solution was stirred at −5--0° C. for 2 h, then was washed with 10% citric acid (2×10 cm³) and brine (10 cm³), then dried (Na₂SO₄) and evaporated to a syrup. This was dissolved in a little 1:1 ethyl acetate/ petroleum ether and passed through a short silica column. Evaporation of the eluent gave the mixture of title carboxylic acids as a colorless syrup (3.986 g, 93%).

H NMR (300 Hz, CDCl₃) 1.47, 9H, s, CMe₃; 2.65, 2H, br t (J 6.6), CH₂CO₂H, 2.85-2.95, 2H, m, CH₂CH₂CO₂H, 4.15-4.17, 2H, m, NHCH₂; 5.07, 2H, s, PhCH₂O; 5.08-5.15, 1H, m, NH; 6.66-7.04 and 7.29-7.46, 8H, Ar—H; CO₂H not observed.

¹³C NMR (75 MHz, CDCl₃) 28.3, CMe₃; 29.6, 30.4, 35.3 and 35.6, 2xCH₂CH₂; 42.3, NHCH₂; 70.7 and 71.3, 2xPhCH₂O; 80.1, CMe₃; 155.6, NCO₂; 178.0 and 178.4, 2xCO₂.

Solid-Phase Synthesis of cyclo-[D-G-Amb-R-G] (SEQ ID NO:50)

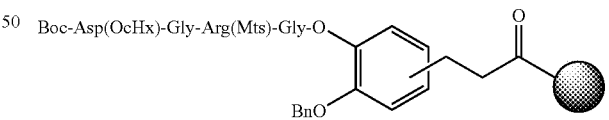

Aminomethyl resin (Peptide Institute, 0.83 mmol/gram, 602 mg, 0.50 mmol) was shaken with 10% DIPEA in DMF for 30, then drained and washed well with DMF.

The benzyloxy linker (429 mg, 1.0 mmol, 2.0 equiv.) was coupled using standard HBTU/DIPEA protocols overnight. The remaining residues were coupled using standard HBTU/ DIPEA protocols for ten minutes each. The final yield of the dried resin was 906 mg. Of this, 725 mg (ca. 0.4 mmol) was cleaved with anhydrous HF using anisole as the scavenger. The resin was washed well with diethyl ether, dried at suction, then gently stirred in 5.0 cm³ DMF containing 0.5 cm³ DIPEA for 48 h. The resin was filtered off and washed well with DMF. Evaporation of the filtrate, followed by preparative HPLC gave cyclo-[D-G-Amb-R-G] (SEQ ID NO:50) as a fluffy white solid (103 mg, 49%). Analysis of the product by LC-MS indicated the presence of the cyclodimer, cyclo-[D-G-Amb-R-G-D-G-Amb-R-G] (SEQ ID NO:52). The ratio of monomer to dimer was approximately 3:2.

EXAMPLE 6

Backbone Substitution and Activated or Safety Catch Linker

This example illustrates that the use of the safety-catch linker with backbone substitution is a useful combination for the synthesis of cyclic peptides.

The sequence Ala-Phe-Leu-Pro-Ala (SEQ ID NO:18) does not cyclize under solution conditions (Schmidt and Lagner, 1997) using BOP/DIEA or under on-resin conditions using the safety-catch linker. However, when the backbone substitution method is applied in combination with the safety-catch linker a substantial amount of cyclic product is obtained. For example, the synthesis and cyclisation of Ala-(Me)Phe-Leu-Pro-Ala (SEQ ID NO:53) yields cyclic product as characterised by ES-MS. Although in this instance the backbone substitution was a methyl group, one skilled in the art would realise that numerous other substituents may also be used, including reversible substituents such as HMB and HnB.

Experimental to Example 6

The assembly of the peptide was carried out using standard in situ neutralization Boc-SPPS protocols on aminomethylated polystyrene resin (sv=0.26 meq/g) derivatised with the safety-catch linker as previously described (see Example 5). After coupling of Boc-(Me)Phe-OH and removal of the Boc group, the peptide was acylated using a solution of the symmetric anhydride of Boc-Ala, prepared from Boc-Ala (10eq) and DIC (5 eq) in DCM. The resin was then treated with TFMSA/TFA/p-cresol (1:10:1) for 2 h to remove the benzyl group for linker activation. The resin was then washed with TFA (3×10 mL), DCM (3×10 mL) and DMF (3×10 mL). The resin was then treated with 2% DIEA in DMF overnight. The solvent was removed on the Genevac and the residue resuspended in acetonitrile/water and analyzed by ES-MS and reversed phase HPLC. The ES-MS spectrum displayed a major peak at the expected m/z value for the cyclo-[Ala-(Me)Phe-Leu-Pro-Ala] (SEQ ID NO:54) calculated for $C_{27}H_{39}N_5O_5$=513.3 (monoisotopic), exp=513.3.

EXAMPLE 7

Ring Contraction and Activated or Safety Catch Linker

In Example 2, a ring contraction auxiliary (HnB) was used to synthesise a difficult cyclic pentapeptide. In this example, we examine the combination of these auxiliaries with activated or safety catch linkers.

The array of compounds listed below is synthesised using activated or safety catch linkers and ring contraction auxiliaries. The effects of this combination on the yield and purity of the product are evaluated.

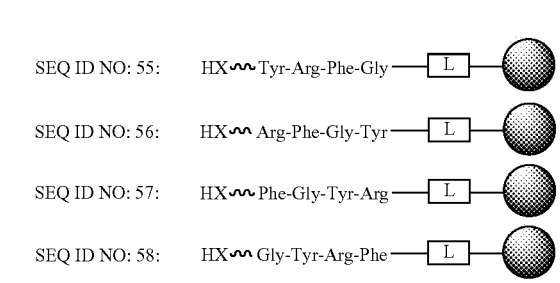

SEQ ID NO: 55:   HX∿∿ Tyr-Arg-Phe-Gly—[L]—●
SEQ ID NO: 56:   HX∿∿ Arg-Phe-Gly-Tyr—[L]—●
SEQ ID NO: 57:   HX∿∿ Phe-Gly-Tyr-Arg—[L]—●
SEQ ID NO: 58:   HX∿∿ Gly-Tyr-Arg-Phe—[L]—●

HX∿∿ = ring contraction auxiliary;
X = O, S; L = activated or safety catch linker

EXAMPLE 8

Ring Contraction, Backbone Substitution and Activated or Safety Catch Linker

The combination of all three approaches provides the pre-organising advantages of backbone substitution and ring contraction with the advantages of activated and safety catch linker cyclisation and concomitant cleavage.

Scheme 11

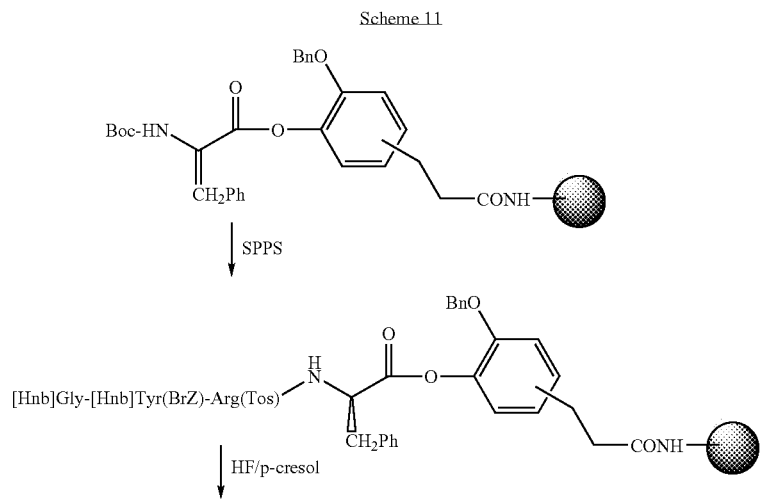

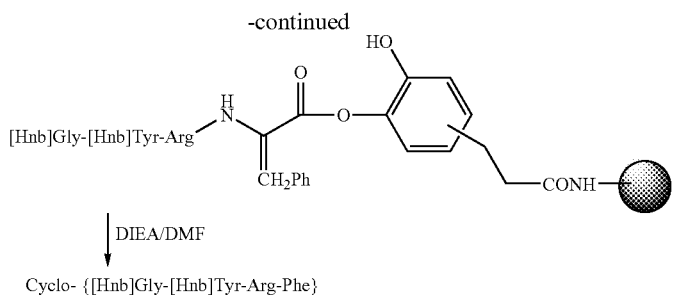

Cyclo-{[Hnb]Gly-[Hnb]Tyr-Arg-Phe}

In this example we show that the combination of ring contraction and backbone substitution can also be applied in an on-resin cyclisation strategy. The selected sequence, [Hnb]Gly-[Hnb]Tyr-Arg-Phe (SEQ ID NO:38), cyclises readily in solution, as illustrated in Example 3. We have applied our safety-catch linker (Example 5) to generate the target cyclic peptide directly from resin.

Experimental to Example 8

The assembly of the peptide was carried out on Boc-Phe-Linker-resin, which was synthesised in the standard manner (see example 6; the resin was aminomethylated resin, sv=0.26 meq/gr). The peptide was then assembled using in situ neutralisation protocols and Boc-SPPS as described previously. The Hnb group was introduced using the standard reductive amination approach. Special care was taken to minimise the time of exposure to NaBH$_4$ (1 eq of NaBH$_4$ for 1 min), as this can cause premature-cleavage of the peptide from the resin. After introduction of the first Hnb group, Boc-Gly was attached via its HBTU activated ester (overnight). The resin was further treated with 1% piperidine (5 min) to remove the O-acylation on the phenol (Hnb). Following introduction of the second HnB group as described above, the resin was treated with HF/p-cresol (9/1; 1 h at 0° C.) to remove the side-chain protection groups and the benzyl group for linker activation. The resin was then washed with ether (3×10 mL), DMF (3×10 mL), DCM/MeOH (10 mL) and dried under high vacuum for 2 h. The resin was then treated with 1% DIEA in DMF overnight. After removal of the solvent, the residue was resuspended in acetonitrile/water and analysed by ES-MS and reversed phase HPLC. The ES-MS spectrum displayed a major peak at the expected m/z value for the cyclo-[[Hnb]Gly-[Hnb]Tyr-Arg-Phe] (SEQ ID NO:2) (calculated for $C_{40}H_{43}N_9O_{11}$=825.3 (monoisotopic), exp M=825.4 gr/mol).

Backbone Linkers

A common approach to synthesising cyclic peptides is attachment of a C-terminal protected amino acid to the resin through its side chain:

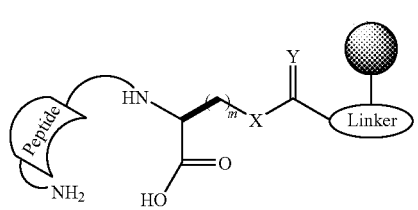

Method A

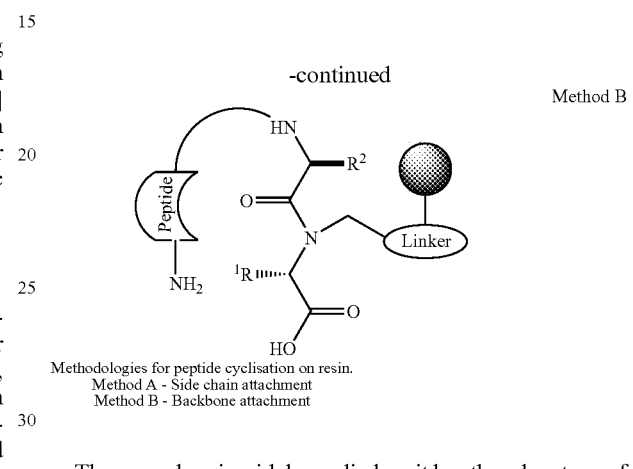

Methodologies for peptide cyclisation on resin.
Method A - Side chain attachment
Method B - Backbone attachment The procedure is widely applied, as it has the advantage of performing the cyclisation while the peptide is still attached to the resin, thus providing a pseudo-dilution environment. The cyclised peptide is then deprotected and cleaved to yield unprotected cyclic peptide. However, from a library perspective this strategy is inadequate because it is restricted to the attachment of specific amino acids to the resin. In an attempt to overcome these problems we have developed two backbone linkers which anchor the peptide to the resin via the first N-amide at the C-terminus.

The main advantage of the backbone linking approach is that it allows flexibility in selecting the linear precursor, ie. the position of cyclisation. This is important, as yields of cyclisation are known to be dependent on the selection of the linear precursor. We have designed and developed two backbone linkers. Linker (7) permits Boc chemistry, ie. stable to neat TFA but is cleaved with HF, while linker (8) permits Fmoc chemistry, ie. is cleaved by TFA (95%):

(7)

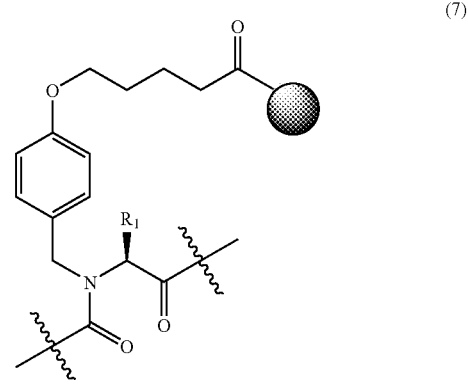

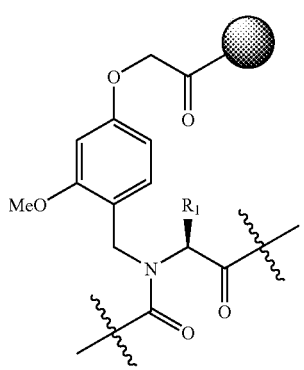

Backbone Linkers Investigated

EXAMPLE 9

Linker (7)

As an example we studied the synthesis of stylostatin. This cyclic heptapeptide was originally isolated from *Stylotella aurantium*, and found to be highly cytotoxic.

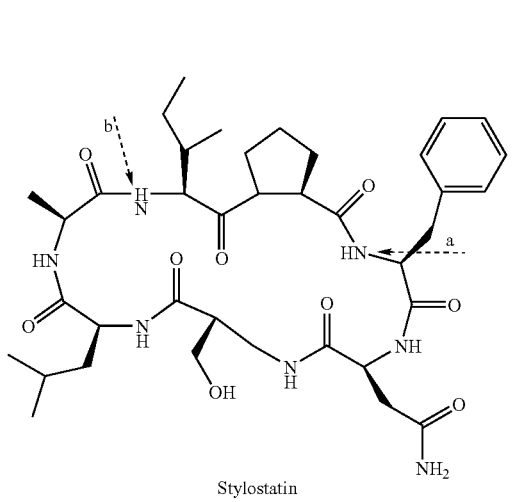

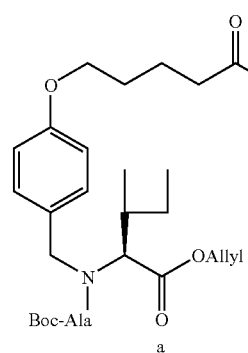

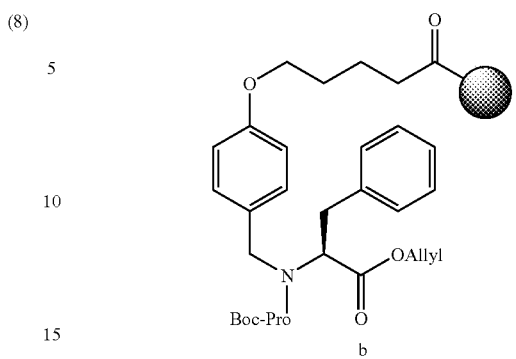

Linker-Dipeptide Units

The Structure of Stylostatin and the Two Linkers a and b that are Used for the Synthesis of Stylostatin The two linker-dipeptide units, depicted above, were prepared in solution as outlined in Scheme 9, and linked to aminomethylated resin; a and b refer to the linking position on the stylostatin backbone on which the attachment to resin is made.

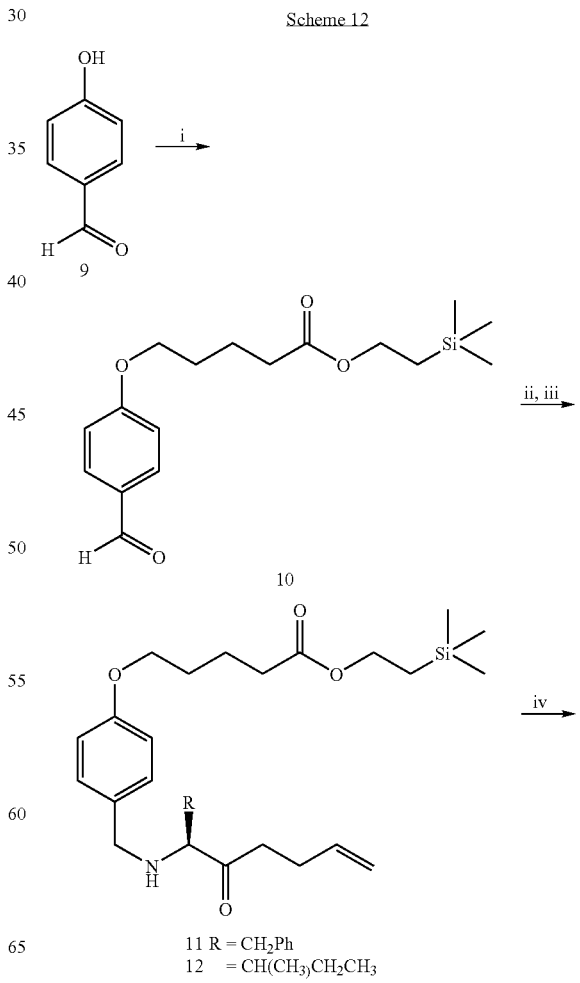

Scheme 12

-continued

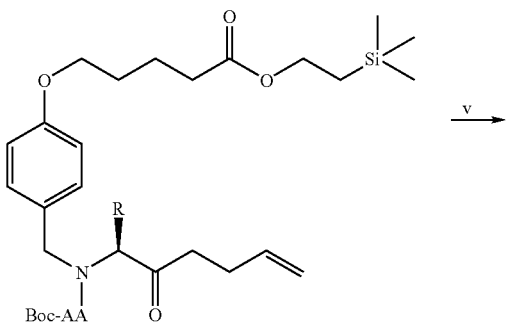

13 R = CH₂Ph
   AA = Boc-Pro
14 R = CH(CH₃)CH₂CH₃
   AA = Boc-AlA

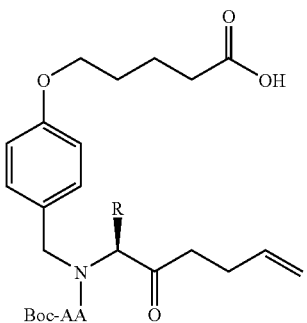

15 R = CH₂Ph
   AA = Boc-Pro
16 R = CH(CH₃)CH₂CH₃
   AA = Boc-AlA

Reagents and Conditions:

i, BrCH₂CH₂CH₂CH₂CO₂Si(CH₃)₃, K₂CO₃, Acetone, Δ, 16 h;

ii, H-Phe-OAllyl or H-Ile-OAllyl, MgSO₄, CH₂Cl₂, r.t., 3 h;

iii, NaBH₃CN, MeOH, r.t., 2 h;

iv, (Boc-Pro)₂-O, DIEA, DMF, r.t, 16 h.; or
    Boc-Ala-F, DIEA, THF, r.t., 30 min.;

v, TBAF, THF, r.t., 2 h.

The linear precursor sequences were then assembled on resin using in situ neutralisation protocols. Removal of the C-terminal allyl protection group was accomplished using Pd(Ph3P)₄. The resin-bound linear peptide was further cyclised using BOP/DIEA activation. After deprotection and cleavage (HF), products were separated, analysed and weighed. The reaction products consisted mainly of cyclic monomer and cyclic dimer. The results are shown in Table 6, in which the amino acid sequence is given in single-letter code. PFNSLAI is SEQ ID NO:59 and NSLAIPF is SEQ ID NO:60.

TABLE 6

Yields of Cyclic Peptides Using Backbone Linker Approach

| Resin-bound linear sequence | Backbone linking position | C-terminal | N-terminal | Yield monocycle | dimer |
|---|---|---|---|---|---|
| PFNSLAI | a | Ile | Pro | 25 | <1 |
| NSLAIPF | B | Phe | Asn | 10 | 24 |

These results emphasise several interesting points. First of all, the backbone linking strategy is a feasible route towards generating cyclic peptides. The yields of isolated material, based on the substitution value of the starting resin, compare well with the overall yields obtained from solution phase cyclisation. Secondly, the cyclisation yields differ significantly for the two precursors in terms of monomer versus dimer. This illustrates the advantage of the backbone linking approach over previous on-resin cyclisation approaches, ie. being able to choose several precursors to the same cyclic peptide. It is generally impossible to predict the optimal precursor for cyclisation. This solid phase strategy allows one to simultaneously assemble several precursors and compare their cyclisation profiles in a fast and efficient way.

Experimental to Example 9

This section describes the synthetic details for the synthesis of a backbone linker and model peptides using Boc chemistry.

Synthesis of Backbone Linker (Scheme 12) and Model Compounds Using Boc Chemistry (Table 6)

4-[5-oxy-(trimethylsilylethylvalerate)]benzaldhyde

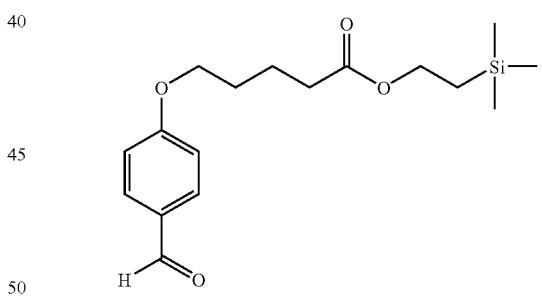

$C_{17}H_{26}O_4Si$
Exact Mass: 322.16
Mol. Wt.: 322.47

4-Hydroxybenzaldehyde (12.2 g, 0.10 mmol), 5-bromo (trimethylsilylethyl)valerate (13.82 g, 0.20 mol), and K₂CO₃ (40.0 g, 0.29 mol) were refluxed in acetone (250 mL) for 16 h. Solids were filtered, washed with acetone and the volatiles were removed in vacuo. The product was purified by column chromatography (Hexane EtOAc, 8:1) to yield a colourless oil (28.2 g, 87%) ¹HNMR (CDCl₃): δ 9.87 (s, 1H, C$\underline{H}$O), 7.82 (d, 2H, J=7.0 Hz, H$_{arom}$), 6.98 (d, 2H, J=7.0 Hz, H$_{arom}$), 4.20 (t, 2H, J=6.9 Hz, OC$\underline{H}_2$), 4.05 (t, 2H, J=6.0 Hz, OC$\underline{H}_2$), 2.42 (m, 2H, C$\underline{H}_2$CO), 1.80 (m, 4H, C$\underline{H}_2$C$\underline{H}_2$), 0.96 (t, 2H, J=6.9 Hz, C$\underline{H}_2$Si), 0.10 (s, 9H, Si(C$\underline{H}_3$)₃; ¹³CNMR (CDCl₃) δ 190.80, 173.45, 164.026, 131.99, 131.99, 129.87, 114.72, 114.72, 67.82, 62.63, 34.00, 28.49, 21.55, 17.35, −1.49; MS [M+H]$^+$=323.4 (expected 323.2).

N-[4-(5-oxy-(trimethylsilylethylvalerate))benzyl]-L-Phenylalanine Allyl Ester

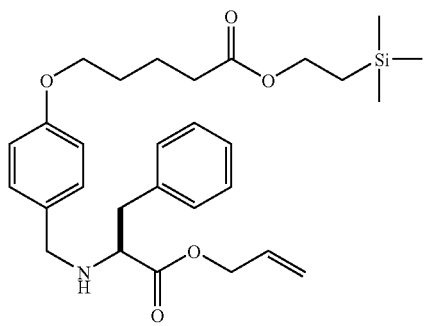

C$_{29}$N$_{41}$NO$_5$Si
Exact Mass: 511.28
Mol. Wt.: 511.73

The aldehyde (16.2 g, 50.2 mmol), phenylalanine allyl ester (20.5, 100 mmol) and excess MgSO$_4$ (~40 g) were stirred in CH$_2$Cl$_2$ (75 mL) at r.t. for 16 h. Solids were filtered and volatiles were removed in vacuo to yield the crude imine as a yellow oil. MeOH (200 mL) and HOAc (3 mL) was added and the reaction mixture was cooled to 10° C. NaCNBH$_3$ (6.1 g, 100 mmol) was added portionwise to the stirred solution. The reaction mixture was allowed to warm to room temperature before being stirred for a further 2 h. Voltiles were removed in vacuo and the resulting residue diluted with H$_2$O (100 mL) and extracted with EtOAc (3×100 mL). The combined EtOAc extractions were washed with saturated brine (1×200 mL) and water (1×200 mL) before being dried over MgSO$_4$. Volatiles were removed in vacuo, and the resulting oil purified by flash chromatography (Hexane EtOAc, 1:1) to yield a clear colourless oil (20.2 g, 79%): $^1$HNMR (CDCl$_3$) δ 7.28 (m, 5H, H$_{arom}$), 7.20 (d, 2H, J=7.0 Hz, H$_{arom}$), 6.85 (d, 2H, J=7.0 Hz, H$_{arom}$), 5.80 (m, 1H, CH=CH$_2$), 5.28 (dd, 1H, J=12.1 Hz, 1.7 Hz, CH=CH$_2$), 5.23 (dd, 1H, J=10.0 Hz, 1.7 Hz, CH=CH$_2$), 4.55 (d, 2H, J=6.4 Hz, PheCH$_2$NH$_2$), 4.15 (t, 2H, J=6.9 Hz, OCH$_2$), 3.92 (m, 2H, OCH$_2$), 3.80 (dd, 2H, J=12.2 Hz, 1.2 Hz, CH$_2$—CH), 3.65 (dd, 2H, J=11.7 Hz, 1.2 Hz, CH$_2$—CH), 3.58 (m, 1H, CHNH), 3.05 (m, 1H, CH$_2$Ph), 2.25 (m, 2H, CH$_2$CO), 1.80 (m, 4H, CH$_2$CH$_2$), 0.95 (t, 2H, J=6.9 Hz, CH$_2$Si), 0.10 (s, 9H, Si(CH$_3$)$_3$); CNMR (CDCl$_3$) δ 173.56, 173.00, 158.32, 136.78, 131.96, 130.67, 129.57, 129.57, 129.27, 129.27, 128.39, 128.39, 126.76, 118.77, 114.36, 114.36, 67.33, 66.48, 62.51, 61.60, 51.13, 39.18, 34.08, 28.68, 21.62, 17.32, −1.51; MS [M+H]$^+$=512.1 (expected 512.3).

Boc-L-Pro-[N-(4-(5-oxy-(trimethylsilylethylvalerate))-benzyl)]-L-Phenylalanine Allyl Ester

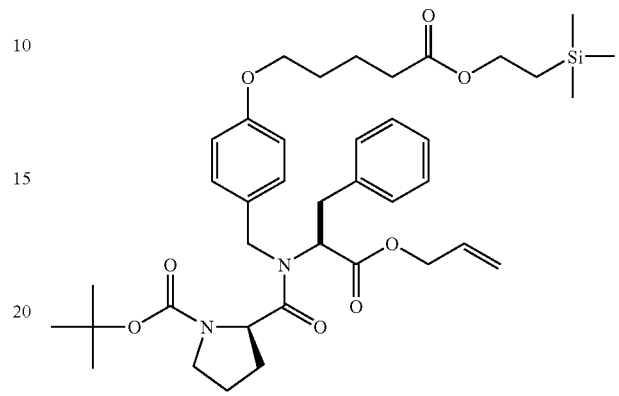

C$_{39}$H$_{56}$N$_2$O$_8$Si
Exact Mass: 708.38
Mol. Wt.: 708.96

Boc-Pro-OH (8.61 g, 40.0 mmol) was dissolved in EtOAc (3.0 mL), to which was added DCCI (4.12 g, 20.0 mmol). After activation for 10-15 min to form the symmetric anhydride, the mixture was filtered and the filtrate was added to a solution of the amine (6) (5.11 g, 10.0 mmol) and DIEA (2.67 mL, 15 mmol). The reaction was stirred at r.t. for 16 h. EtOAc (100 mL) was added and the reaction mixture was washed with 10% K$_2$CO$_3$ solution (2×250 ml), brine (1×250 mL) and H$_2$O (1×250 mL) before dried over MgSO$_4$. Volatiles were removed in vacuo, and the resulting oil purified by flash chromatography (Hexane:Et$_2$O, 5:1) to yield a clear colourless oil (3.55 g, 60%): $^1$HNMR (CDCl$_3$) δ 7.20 (m, 7H, H$_{arom}$), 6.85 (d, 2H, J=7.0 Hz, H$_{arom}$), 5.98 (m, 1H, CH=CH$_2$), 5.20 (m, 2H, CH=CH$_2$), 4.50 (m, 3H, CH$_2$CH and PheCH$_2$N), 4.20 and 4.13 (rotamers, dd, 1H, J=7 Hz, 2 Hz, NCH), 4.15 (t, 2H, J=6.9 Hz, OCH$_2$), 3.92 (m, 2H, OCH$_2$), 3.71 (m, 2H, CH$_2$—CH), 3.31 (m, 4H, CH$_2$Ph and CH$_2$N), 2.25 (m, 2H, CH$_2$CO), 2.05 (m, 4H, CH$_2$CH$_2$), 1.80 (m, 4H, CH$_2$CH$_2$), 1.48 (br s, 9H, C(CH$_3$)$_3$, 0.95 (t, 2H, J=6.9 Hz, CH$_2$Si), 0.10 (s, 9H, Si(CH$_3$)$_3$); $^{13}$CNMR (CDCl$_3$) δ rotomers 173.54 and 173.00, 172.42, rotomers 170.08 and 169.47, rotomers 158.68 and 158.50, rotomers 154.31 and 153.98, rotomers 138.35 and 138.05, rotomers 132.45 and 131.96, 129.40, 129.40, 129.10, 128.91, 128.63, 128.63, 127.52, rotomers 126.75 and 126.62, rotomers 118.26 and 118.06, 114.32, 114.32, rotomers 79.96 and 79.19, 67.34, rotomers 65.96 and 65.80, 62.55, rotomers 60.68 and 60.58, rotomers 57.44 and 56.94, 51.37, rotomers 46.83 and 46.77, rotomers 35.11 and 34.97, 34.07, rotomers 30.84 and 29.78, 28.67, 28.46, rotomers 24.02 and 22.77, 21.68 17.32, −1.50; MS [M+H]$^+$=709.6 (expected 709.4).

Boc-L-Pro-[N-(4-(5-oxyvaleric acid)benzyl)]-L-Phenylalanine Allyl Ester

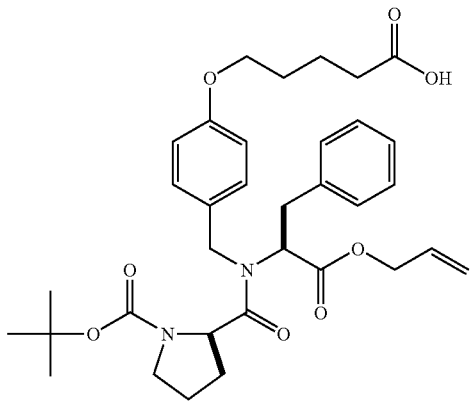

$C_{34}H_{44}N_2O_8$
Exact Mass: 608.31
Mol. Wt.: 608.72

The ester (2.0 g, 2.82 mmol) was stirred in a solution of THF (20 mL) at r.t. TBAF (3 ml, 1M) was added dropwise and saponification proceeded for 3 h. $H_2O$ (100 mL) and HOAc (3 mL) was added to the reaction mixture. The acid was extracted into EtOAc (3×100 mL) and was washed $H_2O$ (1×250 mL) before being dried over $MgSO_4$. Volatiles were removed in vacuo, and the resulting oil purified by flash chromatography (Hexane:$Et_2O$, 5:1) to yield a clear colourless oil. The tertiary amide (product) was purified by column chromatography ($CH_2Cl_2$:MeOH, 19:1) to yield a white solid (2.54 g, 90%); mp. 28-30° C.: $^1$HNMR (CDCl$_3$) δ 8.89 (br s, 1H, O$\underline{H}$), 7.20 (m, 7H, H$_{arom}$), 6.75 (dd, 2H, J=7.1 Hz, 1.9 Hz, H$_{arom}$), 5.88 (m, 1H, C$\underline{H}$=CH$_2$), 5.25 (m, 2H, CH=C$\underline{H}_2$), 4.50 (m, 3H, CH$_2$C$\underline{H}$ and PheC$\underline{H}_2$N), 4.20 and 4.13 (rotomers, dd, 1H, J=6.9 Hz, 1.9 Hz, NC$\underline{H}$), 3.88 (m, 2H, C$\underline{H}_2$O), 3.71 (m, 2H, C$\underline{H}_2$—CH), 3.41 (m, 4H, C$\underline{H}_2$N, C$\underline{H}_2$Ph), 2.25 (m, 2H, C$\underline{H}_2$CO), 2.05-1.85 (m, 8H, 2xC$\underline{H}_2$C$\underline{H}_2$), 1.48 (br s, 9H, C(C$\underline{H}_3$)$_3$; $^{13}$CNMR (CDCl$_3$) δ rotomers 179.09 and 177.04, 173.05, rotomers 170.08 and 169.48, rotomers 158.64 and 158.44, rotomers 154.28 and 153.96, rotomers 138.31 and 138.02, rotomers 132.43 and 131.94, 129.41, 129.41, 128.99, 128.69, 128.48, 128.48, 127.50, rotomers 126.78 and 126.65, rotomers 118.30 and 118.10, 114.37, 114.37 rotomers 80.17 and 79.38, 67.30, rotomers 65.99 and 65.84, rotomers 60.72 and 60.54, rotomers 57.49 and 57.00, 51.40, rotomers 46.86, rotomers 35.09 and 34.95, 33.56, rotomers 30.83 and 29.78, rotomers 28.46 and 20.76, rotomers 24.00 and 22.78, 21.39; MS [M+H]$^+$=609.3 (expected 609.3).

N-[4-(5-oxy-(trimethylsilylethylvalerate))benzyl]-L-Isoleucine Allyl Ester

The aldehyde (16.2 g, 50.2 mmol), isoleucine allyl ester (20.5, 100 mmol) and excess $MgSO_4$ (~40 g) were stirred in $CH_2Cl_2$ (75 mL) at r.t. for 3 h. Solids were filtered and volatiles were removed in vacuo to yield the crude imine as a yellow oil. MeOH (200 mL) and HOAc (3 mL) was added and the reaction mixture was cooled to 10° C. NaCNBH$_3$ (6.1 g, 100 mmol) was added portionwise to the stirred solution. The reaction mixture was allowed to warm to room temperature before being stirred for a further 2 h. Volatiles were removed in vacuo and the resulting residue diluted with $H_2O$ (100 mL) and extracted with EtOAc (3×100 mL). The combined EtOAc extractions were washed with saturated brine (1×200 mL) and water (1×200 mL) before being dried over $MgSO_4$. Volatiles were removed in vacuo, and the resulting oil purified by flash chromatography (1:1 hexane EtOAc) to yield a clear colourless oil (20.2 g, 79%). $^1$HNMR (CDCl$_3$): δ 7.24 (d, 2H, J=8.0 Hz, H$_{arom}$), 6.85 (d, 2H, J=8.0 Hz, H$_{arom}$), 5.98 (m, 1H, C$\underline{H}$=CH$_2$), 5.31 (d, 1H, J=27.2 Hz, CH=C$\underline{H}_2$), 5.27 (dd, 1H, J=13.2 Hz, 1.7 Hz, CH=C$\underline{H}_2$), 5.10 (dd, 1H, J=11.2 Hz, 1.7 Hz, CH=C$\underline{H}_2$), 4.65 (m, 2H, PheC$\underline{H}_2$N), 4.15 (t, 2H, J=6.9 Hz, OC$\underline{H}_2$), 3.92 (m, 2H, OC$\underline{H}_2$), 3.81 (d, 1H, J=13 Hz, C$\underline{H}_2$—CH), 3.60 (d, 1H, J=13 Hz, C$\underline{H}_2$—CH), 3.17 (m, 1H, C$\underline{H}$), 2.90 (m, CH$_2$C$\underline{H}$CH$_3$), 2.35 (m, 2H, CHC$\underline{H}_2$CH$_3$), 1.80 (m, 2H, C$\underline{H}_2$CH$_2$), 1.52 (m, 1H, CHC$\underline{H}_2$CH$_3$), 1.20 (m, 1H, CHC$\underline{H}_2$CH$_3$), 0.95 (t, 2H, J=6.9 Hz, C$\underline{H}_2$Si), 0.92 (d, 3H, J=7.6 Hz, C$\underline{H}_3$CH), 0.90 (t, 3H, J=7.0 Hz, C$\underline{H}_2$CH$_3$), 0.10 (s, 9H, Si(C$\underline{H}_3$)$_3$); $^{13}$CNMR (CDCl$_3$) δ 174.55, 174.25, 158.96 132.66, 131.22, 130.48, 130.48, 119.45, 115.02, 115.02, 68.05 65.92, 65.52, 63.20, 52.36, 38.74, 34.78, 29.39, 29.39, 26.35, 22.34, 18.02, 16.23, 12.13, −0.81; MS [M+H]$^+$=478.3 (expected 478.3).

Boc-L-Ala-[N-(4-(5-oxy-(trimethylsilylethylvalerate))-benzyl)]-L-Isoleucine Allyl Ester

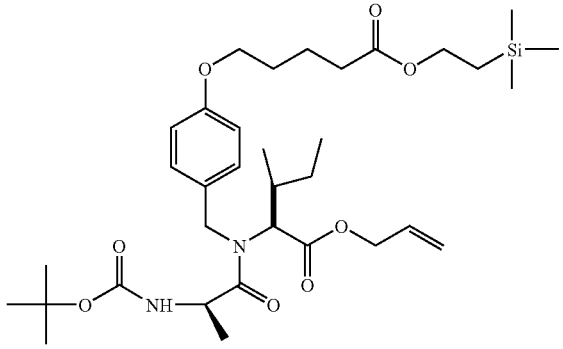

$C_{34}H_{16}N_2O_8Si$
Exact Mass: 648.38
Mol. Wt.: 648.90

Boc-Ala-OH (2.89 g, 15.0 mmol) was dissolved in $CH_2Cl_2$ (30 mL), to which was added DAST (4.12 g, 20.0 mmol). After activation for 10-15 min to form the acid fluororide, the mixture was washed with cold ($H_2O$, dried over $MgSO_4$ and the volatiles were removed in vacuo. The acid fluoride was then added immediately to a solution of the amine (4.78 g, 10.0 mmol) and DIEA (2.67 mL, 15 mmol) in THF (20 mL). The reaction was stirred at r.t. for 16 h. EtOAc (100 mL) was added and the reaction mixture was washed with 10% $K_2CO_3$ solution (2×250 ml), brine (1×250 mL) and $H_2O$ (1×250 mL) before being dried over $MgSO_4$. Volatiles were removed in vacuo, and the resulting oil purified by flash chromatography (hexane:diethyl ether, 1:5) to yield a clear colourless oil (2.86 g, 44%) $^1$HNMR (CDCl$_3$): δ 7.24 (d, 2H, J=8.0 Hz, H$_{arom}$), 6.85 (d, 2H, J=8.0 Hz, H$_{arom}$) 5.98 (m, 1H, C$\underline{H}$=CH$_2$), 5.31

(d, 1H, J=14.2 Hz, CH=C$\underline{H}_2$), 5.23 (d, 1H, J=12.0 Hz, CH=C$\underline{H}_2$) 4.65 (m, 3H, PheC$\underline{H}_2$N, C$\underline{H}$CH$_3$), 4.15 (t, 2H, J=6.9 Hz, OC$\underline{H}_2$), 3.92 (m, 2H, OC$\underline{H}_2$), 3.81 (d, 1H, J=13 Hz, C$\underline{H}_2$—CH), 3.60 (d, 1H, J=13 Hz, C$\underline{H}_2$—CH), 3.17 (m, 1H, C$\underline{H}$), 2.90 (m, CH$_2$C$\underline{H}$CH$_3$), 2.35 (m, 2H, CHC$\underline{H}_2$CH$_3$), 1.80 (m, 2H, C$\underline{H}_2$CH$_2$), 1.52 (m, 1H, C$\underline{H}$CH$_2$CH$_3$), 1.45 (s, 9H, C(C$\underline{H}_3$)$_3$), 1.20 (m, 1H, CHC$\underline{H}_2$CH$_3$), 0.95 (t, 2H, J=6.9 Hz, C$\underline{H}_2$Si), 0.97 (s, 3H, C$\underline{H}_3$), 0.92 (d, 3H, J=7.6 Hz, C$\underline{H}_3$CH), 0.90 (t, 3H, J=7.0 Hz, CH$_2$C$\underline{H}_3$), 0.10 (s, 9H, Si(C$\underline{H}_3$)$_3$); MS [M+H]$^+$=649.5 (expected 649.4).

CH=C$\underline{H}_2$), 5.22 (d, 1H, J=11.0 Hz, CH=C$\underline{H}_2$), 4.65 (m, 3H, PheC$\underline{H}_2$N, C$\underline{H}$CH$_3$), 3.92 (m, 2H, OC$\underline{H}_2$), 3.81 (d, 1H, J=13 Hz, C$\underline{H}_2$—CH), 3.60 (d, 1H, J=13 Hz, C$\underline{H}_2$—CH), 3.17 (m, 1H, C$\underline{H}$), 2.90 (m, CH$_2$C$\underline{H}$CH$_3$), 2.35 (m, 2H, CHC$\underline{H}_2$CH$_3$), 1.80 (m, 2H, C$\underline{H}_2$CH$_2$), 1.52 (m, 1H, CHC$\underline{H}_2$CH$_3$), 1.45 (s, 9H, C(C$\underline{H}_3$)$_3$), 1.20 (m, 1H, CHC$\underline{H}_2$CH$_3$), 0.97 (s, 3H, C$\underline{H}$3), 0.92 (d, 3H, J=7.6 Hz, C$\underline{H}_3$CH), 0.90 (t, 3H, J=7.0 Hz, CH$_2$C$\underline{H}_3$); δ MS [M+H]$^+$=549.1 (expected 549.3).

H-Asn-Ser-Leu-Ala-Ile-Pro-Phe-OH (SEQ ID NO:60)

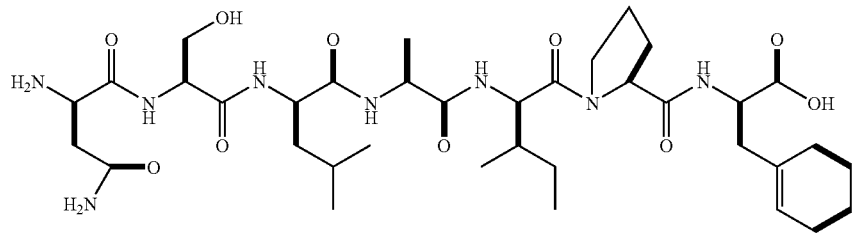

$C_{36}H_{56}N_8O_{10}$

Exact Mass: 760.41

Mol. Wt.: 760.88

The peptide was synthesised in stepwise fashion by established methods using in situ neutralisation/HBtU activation protocols for Boc chemistry. 13 The Xanthyl protecting group was used for the Asn residue and the Benzyl ether for the Ser residue. Coupling reactions were monitored by quantitative ninhydrin assay and were typically >99.9%. After chain assembly was complete the removal of the allyl protecting group was achieved by the addition of tetrakis (triphenylphosphine) palladium [Pd(PPh$_3$)$_4$] (580 mg, 0.5 mmol, 3 molar equiv.) to the resin in a solution of CHCl$_3$ HOAc: NMM. Vigorous shaking was initiated and continued for 14 h. The solvent was removed and the residue was washed with a 10% solution of diethyldithiocarbamic acid, sodium salt trihydrate [(C$_2$H$_5$)$_2$N$_2$CS$_2$Na.3H$_2$O] in DMF (2×10 mL), DMF (2×10 mL) MeOH CH$_2$Cl$_2$, 1:1 (2×10 mL) and CH$_2$Cl$_2$ (2×10 mL). The N$^\alpha$-Boc group removed with neat TFA (2×1 min treatment) and the peptide was cleaved from resin (200 mg, 0.166 mmol/g) using HF:p-cresol, 11 mL, 10:1, for 1 h at −5° C. After removal of the HF under reduced pressure, the crude peptide was precipitated in anhydrous ether before being dissolved in the HPLC buffer and lyophilized. The peptide H-Asn-Ser-Leu-Ala-Ile-Pro-Phe-OH (20) was purified by semi-preparative HPLC (30-90% B over 60 min) to yield a white powder (25 mg 78%); MS [M+H]$^+$=761.21 (expected 761.42)

Boc-L-Ala-[N-(4-(5-oxyvaleric acid)benzyl)]-L-Isoleucine Allyl Ester

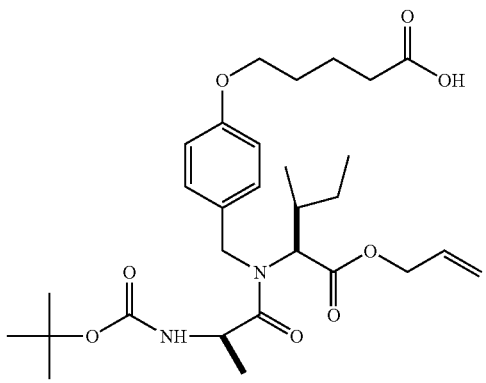

$C_{29}H_{44}N_2O_8$

Exact Mass: 548.31

Mol. Wt.: 548.67

The ester (2.0 g, 2.82 mmol) was stirred in a solution of THF (20 mL) at r.t. TBAF (3 ml, 1M) was added dropwise and saponification proceeded for 3 h. H$_2$O (100 mL) and HOAc (3 mL) was added to the reaction mixture. The acid was extracted into EtOAc (3×100 mL). The combined EtOAc extractions were washed with saturated brine (1×100 mL) and water (1×100 mL) before being dried over MgSO$_4$. Volatiles were removed in vacuo, and the resulting oil purified by semi-preparative HPLC (0-60% B over 60 min) to yield the tertiary amide as a colourless oil (2.54 g, 44%): $^1$HNMR (CDCl$_3$): δ 7.22 (d, 2H, J=8.0 Hz, H$_{aroma}$), 6.80 (d, 2H, J=8.0 Hz, H$_{aroma}$), 5.91 (m, 1H, C$\underline{H}$=CH$_2$), 5.21 (d, 1H, J=14.2 Hz, H-Pro-Phe-Asn-Ser-Leu-Ala-Ile-OH (SEQ ID NO:59)

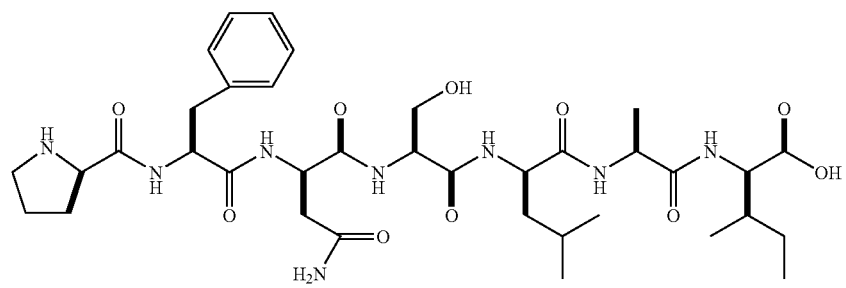

$C_{36}H_{56}N_8O_{10}$
Exact Mass: 760.41
Mol. Wt.: 760.88

The peptide was synthesised using a similar procedure to that in the previous experiment above using the precursor Boc-Ala-[Backbone attachmenet]-Ile-O-Allyl (200 mg, 0.180 mmol/g). The peptide H-Pro-Phe-Asn-Ser-Leu-Ala-Ile (SEQ ID NO:59) was purified by semi-preparative HPLC (30-90% B over 60 min) to yield a white powder (10.5 mg, 39%); MS $[M+H]^+$=761.2 (expected 761.4).

Solution Cyclization

Method 1: Cyclo-(Pro-Phe-Asn-Ser-Leu-Ala-Ile) (SEQ ID NO:63)

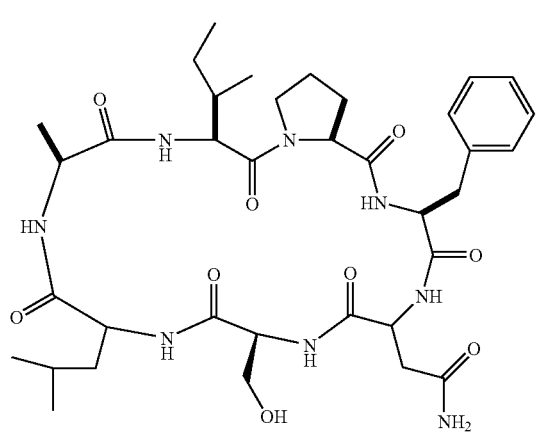

$C_{36}H_{54}N_8O_9$
Exact Mass: 742.40
Mol. Wt.: 742.86

The linear peptide H-Asn-Ser-Leu-Ala-Ile-Pro-Phe-OH (SEQ ID NO:60) (15.0 mg, 0.020 mmol) and BOP (26.1 mg, 0.060 mmol) was stirred in DMF (19.7 mL, $1\times10^{-3}$ M) at $-10°$ C. DIPEA (35 µL, 0.197 mmol) was added dropwise to the solution. After the reaction was left to stir for a further 2 h at this temperature, all volatiles were removed in vacuo. The peptide Cyclo-(Pro-Phe-Asn-Ser-Leu-Ala-Ile) (SEQ ID NO:63) was purified by semi-preparative HPLC (30-90% B over 60 min) to yield a white powder (7.0 mg, 48%). $^1$HNMR (DMSO): δ MS $[M+H]^+$=743.2 (expected 743.4092). Also isolated was the dimer, Cyclo-(Asn-Ser-Leu-Ala-Ile-Pro-Phe-Asn-Ser-Leu-Ala-Ile-Pro-Phe) (SEQ ID NO:64) (3 mg, 21%); MS $[M+H]^+$=1486.2 (expected 1486.8), and the trimer, Cyclo-(Asn-Ser-Leu-Ala-Ile-Pro-Phe-Asn-Ser-Leu-Ala-Ile-Pro-Phe-Asn-Ser-Leu-Ala-Ile-Pro-Phe) (SEQ ID NO:65) (0.7 mg, 5%); MS $[M+H]^{2+}$=1115.1 (expected 1115.1)

Method 2: Cyclo-(Pro-Phe-Asn-Ser-Leu-Ala-Ile) (SEQ ID NO:63)

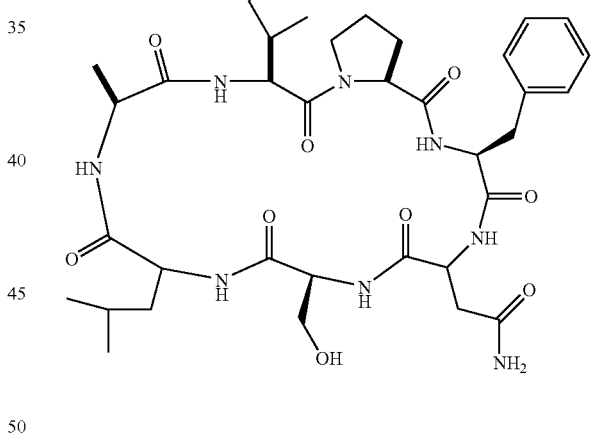

$C_{36}H_{54}N_8O_9$
Exact Mass: 742.40
Mol. Wt.: 742.86

The peptide was synthesized using a similar procedure to Method 1 above using H-Pro-Phe-Asn-Ser-Leu-Ala-Ile-OH (SEQ ID NO:59) (100 mg, 0.131 mmol), BOP (174 mg, 0.393 mmol), and DIPEA (228 µL, 1.31 mmol). The peptide cyclo-(Pro-Phe-Asn-Ser-Leu-Ala-Ile) (SEQ ID NO:63) was purified by semi-preparative HPLC (10-70% B over 60 min) to yield a white powder (10.5 mg, 67%); MS $[M+H]^+$ =743.2 (expected 743.4092). All other physical characteristics ($^1$H NMR, m.p., HPLC retention time, and amino acid analysis) were also consistent with the results reported for Method 1.

On-Resin Cyclization

Method 1: Cyclo-(Pro-Phe-Asn-Ser-Leu-Ala-Ile) (SEQ ID NO:63)

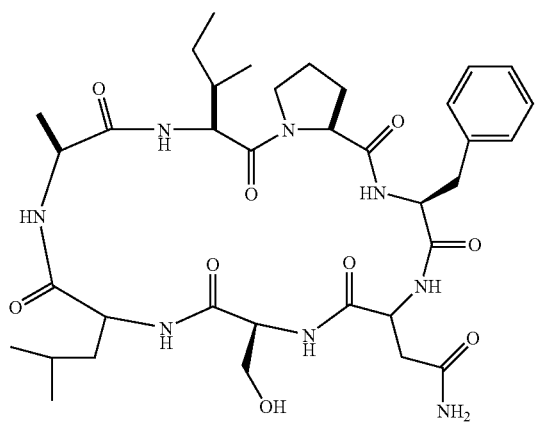

$C_{36}H_{54}N_8O_9$
Exact Mass: 742.40
Mol. Wt.: 742.86

After chain assembly for the linear peptide was complete (synthesised from the solid support where the linker was attached between Boc-Pro-Phe-O-Allyl). The allyl protecting group and the $N^\alpha$-Boc group was removed with [Pd(PPh$_3$)$_4$] (580 mg, 0.5 mmol) and TFA (2×1 min treatment) the reaction mixture was then cooled to −10° C. and BOP (221 mg, 0.5 mmol) was added. 2, 6 Lutidene (194 μL, 1.66 mmol) was then added dropwise and the reaction continued until the ninhydrin assay found an absence of amine <0.1%. The organic material was filtered from the resin (250 mg, 0.167 mmol/g) and the cyclic peptide was cleaved from resin using HF:p-cresol, 11 mL, 10:1, for 1 h at −5° C. After removal of the HF under reduced pressure, the crude peptide was precipitated in anhydrous ether before being dissolved in the HPLC buffer and lyophilized. The peptide Cyclo-(Pro-Phe-Asn-Ser-Leu-Ala-Ile) (SEQ ID NO:63) was purified by semi-preparative HPLC (30-90% B over 60 min) to yield a white powder (3.1 mg, 10%): $^1$HNMR (DMSO) δ MS [M+H]$^+$=743.2 (expected 743.4092). Also isolated was the dimer, Cyclo-(Asn-Ser-Leu-Ala-Ile-Pro-Phe-Asn-Ser-Leu-Ala-Ile-Pro-Phe) (SEQ ID NO:64) (7.6 mg, 24.5%); MS [M+H]$^+$=1486.2 (expected 1486.8), and the trimer, Cyclo-(Asn-Ser-Leu-Ala-Ile-Pro-Phe-Asn-Ser-Leu-Ala-Ile-Pro-Phe-Asn-Ser-Leu-Ala-Ile-Pro-Phe) (SEQ ID NO:65) (0.4 mg, 1%); MS [M+H]$^{2+}$=1115.2 (expected 1115.1). All other physical characteristics (H NMR, m.p., HPLC retention time, and amino acid analysis) were also consistent with what was reported above.

Method 2: Cyclo-(Pro-Phe-Asn-Ser-Leu-Ala-Ile) (SEQ ID NO:63)

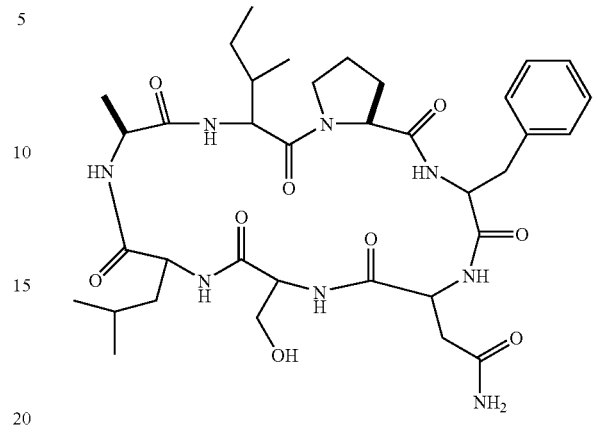

$C_{36}H_{54}N_8O_9$
Exact Mass: 742.40
Mol. Wt.: 742.86

The peptide was synthesized using a similar procedure to Method 1 using the precursor where the linker was attached between Boc-Ala-Ile-O-Allyl (200 mg, 0.203 mmol/g), [Pd(PPh$_3$)$_4$] (290 mg, 0.250 mmol), BOP (60 mg, 0.136 mmol), and 2,6-lutidene (237 μL, 2.03 mmol) The peptide cyclo-(Pro-Phe-Asn-Ser-Leu-Ala-Ile) (SEQ ID NO:63) (3) was purified by semi-preparative HPLC (30-90% B over 60 min) to yield a white powder (8.2 mg, 25 w); MS [M+H]$^+$=743.2 (expected 743.4). All other physical characteristics ($^1$H NMR, m.p., HPLC retention time, and amino acid analysis) were also consistent with what was reported above.

EXAMPLE 10

Fmoc-Based Synthesis Using Linker 8

Similar to linker (7), we have employed linker (8) for the Fmoc-based synthesis of a series of cyclic pentapeptides. The synthesis of the linker is illustrated in Scheme 13, and cyclic products obtained using this linker are listed in Table 7.

Scheme 13

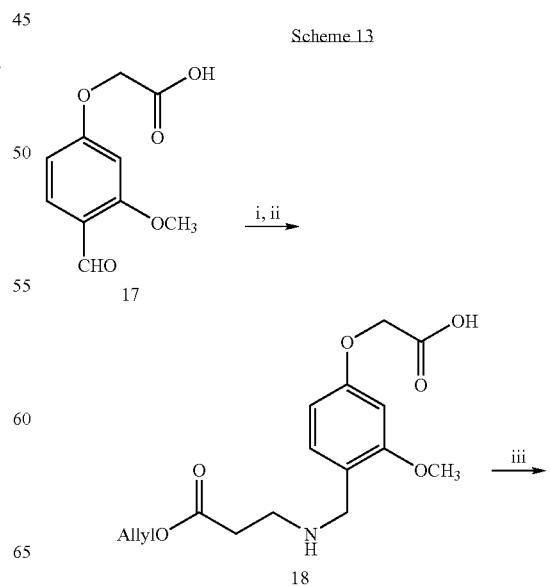

-continued

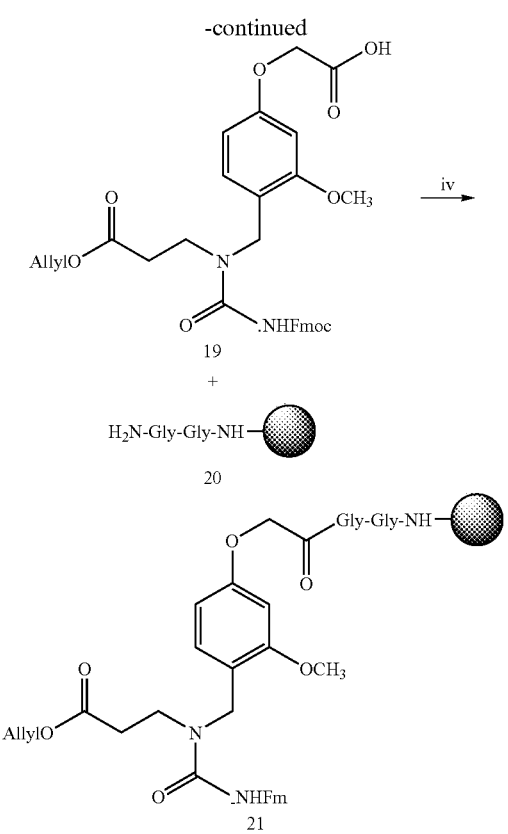

Reagents and Conditions
i, NH$_2$(CH$_2$)$_2$CO$_2$-Allyl, MgCl$_2$, THF, r.t. 72 h;
ii, NaCNBH$_3$, CH$_3$OH, r.t., 2 h;
iii, BOP, Fmoc-Gly-OH, DIEA, DMF, 24 h;
iv, HBTU, DIEA, DMF, 120 min

TABLE 7

Cyclisation Yields Using Fmoc Backbone Linker

| Peptide Sequence | Yield (%) | Reaction Time | SEQ ID NO: |
|---|---|---|---|
| Cyclo-[Leu-Asp-Val-Gly-β-Ala] | 18% | 12 h | 66 |
| Cyclo-[Arg-Gly-Asp-Gly-β-Ala] | 9% | 24 h | 67 |
| Cyclo-[Phe-Lys-Trp-Gly-β-Ala] | 15% | 12 h | 68 |

Experimental to Example 10

This section describes the synthetic details for the synthesis of a backbone linker and model peptides using Fmoc chemistry.

Synthesis of Backbone Linker and Model Compounds Using Fmoc Chemistry

General Methods

The fluorenyl-protected amino acids were coupled onto the resin as their free acids (4 mol equiv.) by addition of HBTU (4 mol equiv.) and DIEA (5 mol. equiv.). The couplings were performed in DMF for 20 min. After each successive coupling the resin was rinsed successively with DMF, MeOH and DCM before monitoring the success with Kaisser ninhydrin assay. Removal of the Fmoc group was achieved by treatment (10 min) with 20% piperidine in DMF. Removal of the allyl protecting group was achieved by the addition of Pd(PPh$_3$)$_4$ (3 mol equiv.) to the resin in a solution of CHCl$_3$: HOAc: NMM, 37:2:1, 5 mL under an atmosphere of nitrogen. Shaking was initiated and continued for 3 h. The resin was rinsed successively with a solution of 10% sodium dithiodicarbonate trihydrate in DMF (twice), DMF, MeOH and DCM, and dried in vacuo.

Linear peptides were removed by TFA (100%) 5 h and checked for purity by HPLC. HPLC was carried out on a Waters apparatus at λ=254 nm on an analytical Vydac column using an isocratic elution with 70% buffer A (H$_2$O, 0.1% TFA) for 5 minutes, followed by a 2.5% linear gradient to 80% buffer B (90% CH$_3$CN, 10% H$_2$O, 0.1% TFA) at 2 mL/min flow rate. After the final removal of the Fmoc group, the resin was rinsed with DMF before HATU (5 mol equv.) was added portionwise to the resin in a solution of DMF (2 mL). DIEA (10 mol equiv.) was added dropwise and shaking was initiated and continued for 6 h before a further 5 mol. equiv. HATU and 10 mol. equiv. DIEA was added. Shaking was again recontinued until the resin gave a negative ninhydrin test. The resin was rinsed once again with DMF, MeOH and DCM, and dried in vacuo.

Cyclic peptides were removed by TFA (100%) 5 h and purified by HPLC. HPLC was carried out on a Waters apparatus at λ=214 nm on a semi-preparative Vydac column using an isocratic elution with 100% buffer A (H$_2$O, 0.1% TFA) for 10 minutes, followed by a 1% linear gradient to 50% buffer B (90% CH$_3$CN, 10% H$_2$O, 0.1% TFA) at 10 mL/min flow rate.

3-Methoxy-4-formylphenol (3)

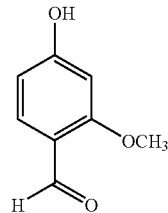

C$_8$H$_8$O$_3$

Exact Mass: 152.05

Mol. Wt.: 152.15

In a 1 L three-necked flask fitted with a dropping funnel, thermometer and drying tube was placed 3-methoxyphenol 5 (70 g, 0.64 mol) and freshly distilled phosphoryl chloride (100 mL, 1.08 mol). The solution was stirred at 0° C. whilst DMF (75 mL, 0.97 mol) was added dropwise over 45 min. The solution was further stirred for 24 h before the pale oil was poured onto crushed ice (1 L) and after 10 min the cloudy solution was washed with ether (2×300 mL). The aqueous layer was once again cooled to 0° C. and adjusted to pH 5.5-6 by careful addition of NaOH (39 g. 0.98 mol) and then NaOAc (380 g, 4.63 mol). Water (150 mL) and ethyl acetate (EtOAc) (500 mL) were added, and the aqueous layer was washed further with EtOAc (250 mL). The combined organic extracts was washed with brine (250 mL) and water (250 mL), dried over MgSO$_4$, and evaporated. The residue was triturated with boiling petroleum spirit and the crystalline solid was collected to give the title compound (25.2 g, 27.2%), m.p. 154-5° C. [lit m.p. [12] 158.5-160° C.]; δH (d$^6$-acetone) 3.08 (1H, br s, OH), 4.92 (2H, s, OCH$_3$), 6.54 (1H, dd, J 9 Hz, J 2 Hz, 6$^{4r}$-H), 6.57 (1H, d, J 2 Hz, 2$^{4r}$-H), 7.77 (1H, d, J 9 Hz, $5^{4r}$-H), 10.24 (1H, s, CHO); $\delta_C$(d$^6$-acetone) 52.76, 99.27, 108.76, 118.63, 130.32, 164.73, 165.29, 187.07.

Methyl 3-methoxy-4-formylphenoxy Ethyl Ester

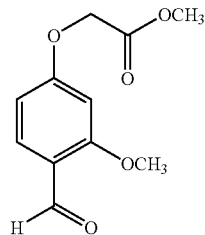

$C_{11}H_{12}O_5$
Exact Mass: 224.07
Mol. Wt.: 224.21

In a 500 mL flask were added the phenol (24 g, 0.166 mol), methyl bromoacetate (75 g, 0.49 mol) and $K_2CO_3$ (67.0 g, 0.49 mol) in acetone (100 mL). The reaction mixture was stirred at reflux for 16 h, cooled to room temperature, filtered, and evaporated under reduced pressure. The oily residue was purified by flash column chromatography EtOAc:Hexane (1:3), to give the methyl ester (31.63 g, 85%), m.p. 79-81° C.; $\delta_H$ (CDCl$_3$) 3.82 (3H, s, OCH$_3$), 4.82 (2H, s, OCH$_2$), 4.80 (2H, s, CH$_2$) 6.48 (1H, dd, J 9 Hz, J 2 Hz, 6$^{4r}$-H), 6.57 (1H, d, J 2 Hz, 2$^{4r}$-H), 7.80 (1H, d, J 9 Hz, 5$^{4r}$-H), 10.29 (1H, s, CHO); $\delta_C$(CDCl$_3$) 52.45, 55.68, 65.07, 99.24, 105.40, 119.84, 130.76, 163.48, 163.96, 168.46, 188.27.

3-Methoxy-4-formylphenoxy Acetic Acid

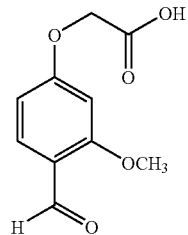

$C_{10}H_{10}O_5$
Exact Mass: 210.05
Mol. Wt.: 210.18

LiOH (0.5 M, 75 mL) was added dropwise to a stirred solution of the methyl ester (7.5 g, 33.45 mmol) in H$_2$O:THF, 3:2 (100 mL) at 0° C. The reaction mixture was allowed to warm to room temperature and stirred for a further 16 h. EtOAc (250 mL) and a Citric acid solution (20%, 500 mL) was added, and the aqueous layer was washed with EtOAc (250 mL). The combined organic extracts were then washed with brine (250 mL) and water (250 mL), dried over MgSO$_4$, and evaporated to dryness under reduced pressure to give the title compound (6.75 g, 96%), m.p. 106-7° C. [lit m.p.[12] 106-7° C.]; $\delta_H$(d$^6$-acetone) 3.40 (1H, s, OH), 3.82 (3H, s, OCH$_3$), 3.92 (3H, s, OCH$_3$), 6.48 (1H, dd, J 9 Hz, J 2 Hz, 6$^{4r}$-H), 6.57 (1H, d, J 2 Hz, 2$^{4r}$-H), 7.80 (1H, d, J 9 Hz, 5$^{4r}$-H), 10.29 (1H, s, CHO); $\delta_C$(d$^6$-acetone) 56.06, 99.01, 106.93, 118.49, 129.80, 163.32, 164.49, 169.57, 187.27.

Allyl 3-amino-[methyl-(2'-methoxy-4'-phenoxy acetic acid)]propanoic Ester

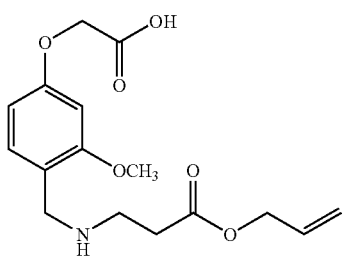

$C_{16}H_{21}NO_6$
Exact Mass: 323.14
Mol. Wt.: 323.34

The aldehyde (1.87 g, 8.92 mmol) and the amine (2.58 g, 20 mmol) was stirred at room temperature in THF (40 mL) in the presence of dry MgSO$_4$ (15 g) for 72 h. The reaction mixture was filtered, and evaporated to dryness under reduced pressure to give a solid residue. The solid was then dissolved in methanol (MeOH) (50 mL) and NaCNBH$_3$ was added portionwise over 10 minutes. The reaction mixture was allowed to stir for a further 3 h before ether (100 mL) was added. The amino acid was extracted into H$_2$O (3×250 mL). Excess NaCl was then added to the H$_2$O layer and the amino acid was extracted back into EtOAc (3×100 mL). The combined organic layers were dried over MgSO$_4$, and evaporated to dryness under reduced pressure to give the title compound as an unpurified oil (2.59 g, 90%); $\delta_H$(d$^6$-acetone) 2.95 (2H, t, J 7 Hz, CH$_2$NH), 3.40 (2H, m, CH$_2$CO), 3.89 (3H, s, OCH$_3$), 4.22 (2H, m, CH$_2$O), 4.42 (2H, s, OCH$_2$), 5.23 (2H, dd, J 24, J 10 Hz, CH=CH$_2$), 5.91 (1H, m, CH), 6.58 (1H, dd, J 9 Hz, J 2 Hz, 6$^{4r}$-H), 6.68 (1H, d, J 2 Hz, 2$^{4r}$-H), 7.42 (1H, d, J 9 Hz, 5$^{4r}$-H), 8.85 (1H, s, OH); $\delta_C$(d$^6$-acetone) 43.27, 47.61, 50.10, 64.49, 66.14, 99.82, 106.30, 112.67, 118.43, 132.97, 133.29, 160.00, 161.67, 170.58, 171.40.

Allyl 3-amino-[carboxymethyl-N-(9'-fluorenyl-methoxy-carbonyl)-amino]-[methyl-(2'-methoxy-4'-phenoxy Acetic acid)]Propanoic Ester

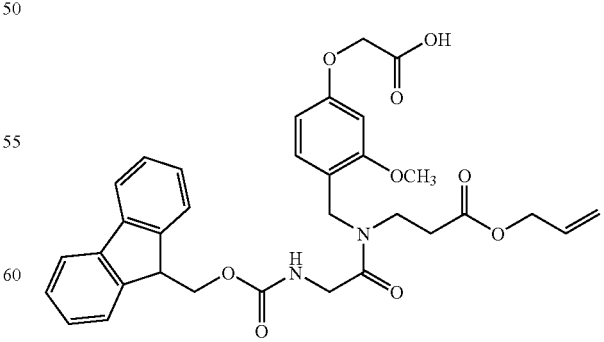

$C_{33}H_{34}N_2O_9$
Exact Mass: 602.23
Mol. Wt.: 602.63

The amino acid (518 mg, 1.6 mmol) was added portionwise to a stirred solution of Fm-Gly-OH (594 mg, 2 mmol), BOP (884 mg, 2 mmol) and DIEA (1 mL) in DMF (5 mL) at r.t. The reaction mixture was allowed to stir for a further 24 h, before being evaporated to dryness under reduced pressure. EtOAc (50 mL) and Citric Acid (10%, 50 mL) were added, and the aqueous layer was washed further with EtOAc (50 mL). The combined organic extracts was washed with brine (50 mL) and water (50 mL), dried over MgSO₄, and evaporated to dryness under reduced pressure. The title compound was purified by HPLC (C-18 reverse phase). HPLC was carried out at λ=254 nM on a Vydac column using a 1.0% linear gradient from 70% buffer A (H₂O, 0.1% TFA) to 80% buffer B (90% CH₃CN, 10% H₂O, 0.1% TFA) at 20 ml/min flow rate (522 mg, 53%).

Cleavage of Fmoc-Gly-β-Ala-O-Allyl from the Acid-Labile Linker

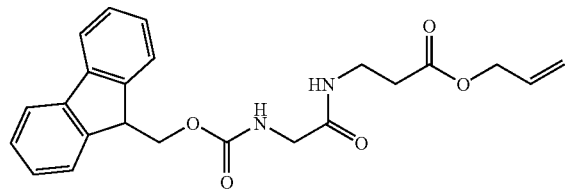

$C_{23}H_{24}N_2O_5$
Exact Mass: 408.17
Mol. Wt. 408.45

Cleavage was performed with 5 mg of the tertiary amide being stirred in TFA (2 mL) for 5 h. The mixture was evaporated to dryness. HPLC was carried out at λ=254 nM on an analytical Vydac column using an isocratic elution 70% buffer A (H₂O, 0.1% TFA) for 5 minutes followed by a 2.5% linear gradient from to 80% buffer B (90% CH₃CN, 10% H₂O, 0.1% TFA) at 10 ml/min flow rate. The dipeptide co-eluted with the known sample and gave the correct molecular ion.

Procedure for the Attachment of the Acid Labile Linker to the Solid Support

DIEA (0.49 mL, 2.75 mmol) was added to a solution of Boc-Gly-OH (43.75 mg, 0.25 mmol), and HBTU (95 mg, 0.25 mmol) in DMF (4 mL). This mixture was then added to Aminomethyl Polystyrene Resin (0.83 mmol/g, 1.0 g). Shaking was initiated and continued for 20 min before being rinsed with DMF. Pyridine:DMF:Acetic anhydride (Ac₂O) (1:1:8, 5 mL) was then added and shaking was recontinued for a further 20 min before being rinsed with excessive amounts of DMF. Removal of the Boc group was achieved by treatment with TFA (2×1 min). A second Boc-Gly-OH (175 mg, 1.0 mmol) was attached by a similar method [DIEA (0.49 mL, 2.75 mmol), HBTU (379 mg, 1.0 mmol) in DMF (4 mL)]. Once again removal of the Boc group was achieved by treatment with TFA (2×1 min). Attachment of Allyl 3-amino-[carboxymethyl-N-(9'-fluorenylmethoxycarbonyl)-amino]-[methyl-(2'-methoxy-4'-phenoxy acetic acid)] propanoic ester 8 was achieved by the addition of the acid (301 mg, 0.5 mmol), DIEA (0.27 mL, 1.5 mmol) HBTU (180 mg, 0.5 mmol) in DMF (4 mL)] to the resin. Shaking was initiated and continued for 20 min before being rinsed with DMF, MeOH and dichloromethane (DCM), and dried in vacuo. After each coupling onto the resin the success of coupling was monitored with Kaisser ninhydrin assay.

Cleavage of Fmoc-Gly-β-Ala-O-Allyl from Solid Support

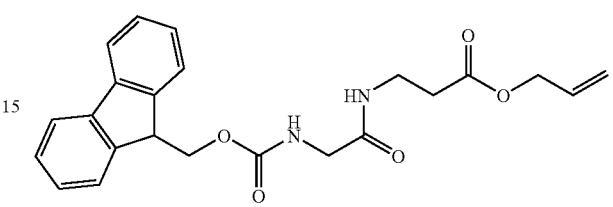

$C_{23}H_{24}N_2O_5$
Exact Mass: 408.17
Mol. Wt.: 408.45

Cleavage was performed with 10 mg of resin being stirred in TFA (2 mL) for 5 h. The mixture was evaporated to dryness under reduced pressure before being taken up in a solution of H₂O: CH₃CN, (1:1, 5 mL), filtered and then lyophilised. HPLC was carried out at λ=254 nM on a semi-preparative Vydac column using an isocratic elution 90% buffer A (H₂O, 0.1% TFA) for 10 minutes followed by a 1.0% linear gradient from to 70% buffer B (90% CH₃CN, 10% H₂O, 0.1% TFA) at 10 ml/min flow rate.

Cyclo-[Leu-Asp-Val-Gly-β-Ala] (SEQ ID NO:66)

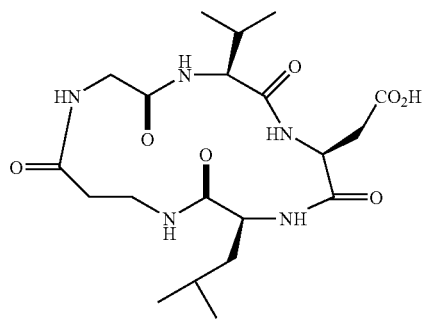

$C_{20}H_{33}N_5O_7$
Exact Mass: 455.24
Mol. Wt.: 455.51

Cyclo-[Leu-Asp-Val-Gly-β-Ala] (SEQ ID NO:66) was lyophilised to a white powder (12.3 mg, 18%): MS [M+H]⁺=456.3 (456.3); Amino Acid Analysis: Gly=1.06, β-Ala=1.01, Asp=1.03, Val=1.03, Leu=0.88.

Cyclo-[Phe-Trp-Lys-Gly-β-Ala] (SEQ ID NO:62)

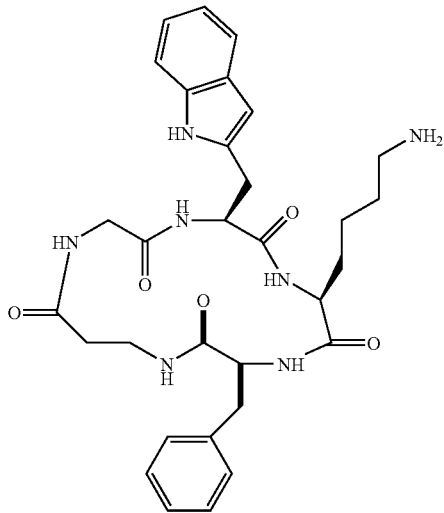

$C_{31}H_{39}N_7O_5$
Exact Mass: 589.30
Mol. Wt.: 589.69

Cyclo-[Phe-Trp-Lys-Gly-β-Ala] (SEQ ID NO:62) was lyophilised to a white powder (8.1 mg, 9%): MS [M+H]$^+$=590.1 (expected 590.3). Amino Acid Analysis: Gly=0.99, β-Ala=1.01, Lys=1.04, Phe=1.02, Trp=0.95.

Cyclo-[Arg-Gly-Asp-Gly-β-Ala] (SEQ ID NO:67)

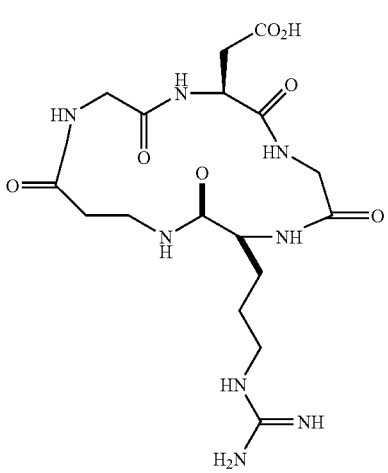

$C_{17}H_{28}N_8O_7$
Exact Mass: 456.21
Mol. Wt.: 456.45

Cyclo-[Arg-Gly-Asp-Gly-β-Ala] (SEQ ID NO:67) was lyophilised to a white powder (8.2 mg, 15%): MS [M+H]$^+$=457.1 (457.3). Amino Acid Analysis: Gly=1.95, β-Ala=1.01, Asp=0.96, Arg=1.09.

EXAMPLE 11

Backbone Linker Plus Ring Contraction

Application to the Synthesis of cyclo-[Ala Pro Leu Phe Ala] (SEQ ID NO:72)

As is emphasised below, we have evaluated the combination of the backbone linker and ring contraction approach in the synthesis of cyclo[Ala Pro Leu Phe Ala] (SEQ ID NO:72). In this instance the peptide was assembled on the backbone linker, and the ring contraction auxiliary appended to the N-terminus through reductive amination. Initial cyclisation and ring contraction were allowed to proceed on resin. The resulting cyclic product was then cleaved off the resin using anhydrous HF.

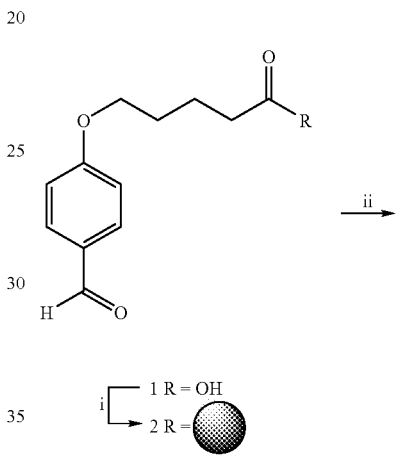

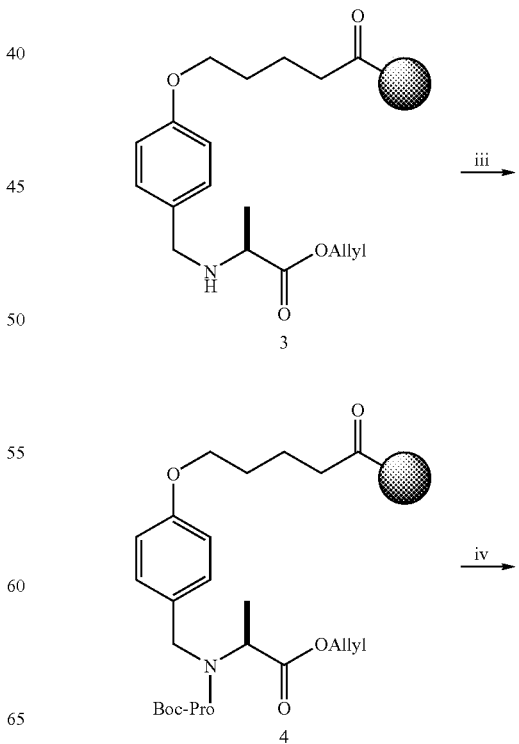

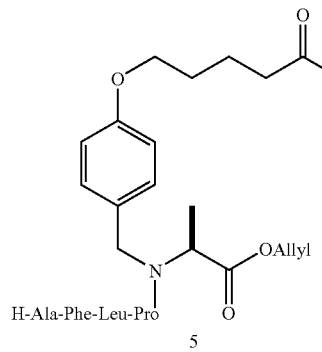
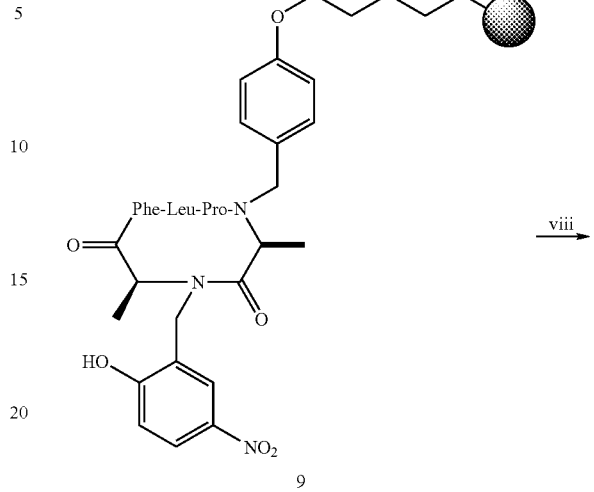
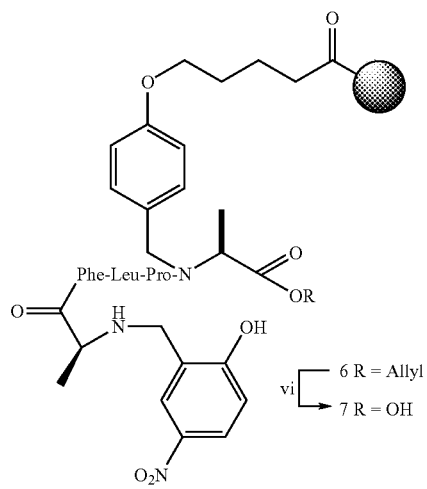
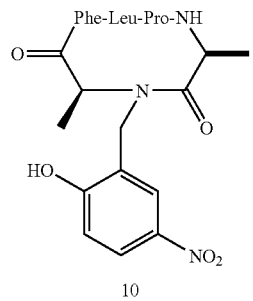
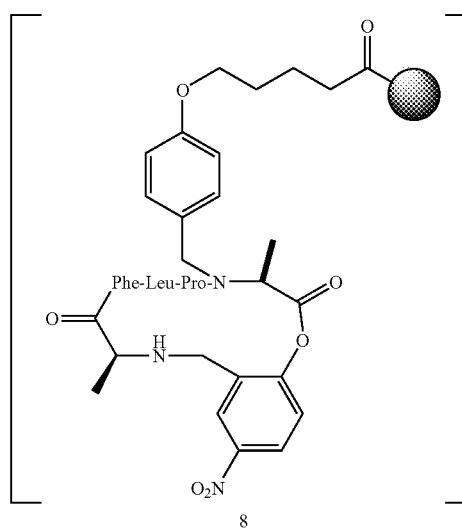

Scheme 14 Reagents and Conditions: I, H-Gly-Leu-Leu-⬤ HBTU, DIEA, DMF, r.t.; ii, Ala-OAllyl, NaBH₃CN, 5% HOAc/MeOH, r.t., 3 h; iv, (Boc-Pro)₂-O, DCM, r.t., 16 h; iv, SPPS; v, 2-Hydroxy-4-nitro-benzaldehyde, NaBH₄, DMF, 2 h; vi, Pd(Ph₃)₄, CH₃Cl: HOAc:NMM, 37:2:1, r.t, 3 h; vii DIC, DIEA, 70° C., 2 h; viii, HF:p-cresol, 10:1, −5° C., 1 h. Compound 5 is SEQ ID NO:69.

Application to the synthesis of a cyclic tetrapeptide, cyclo [[Hnb]Tyr Arg Phe Gly] (SEQ ID NO:5)

Starting from the attachment of the linker to aminomethyl polystyrene resin 11 (sv=0.21 mmol/g), reductive amination of the protected amino acid H-Gly-OAllyl using NaCNBH₃ followed by acylation proceeded quantitatively to give 12. Addition of Boc-Arg(Tos)-OH using standard solid phase peptide protocols gave the linear peptide 13 (Scheme 15).

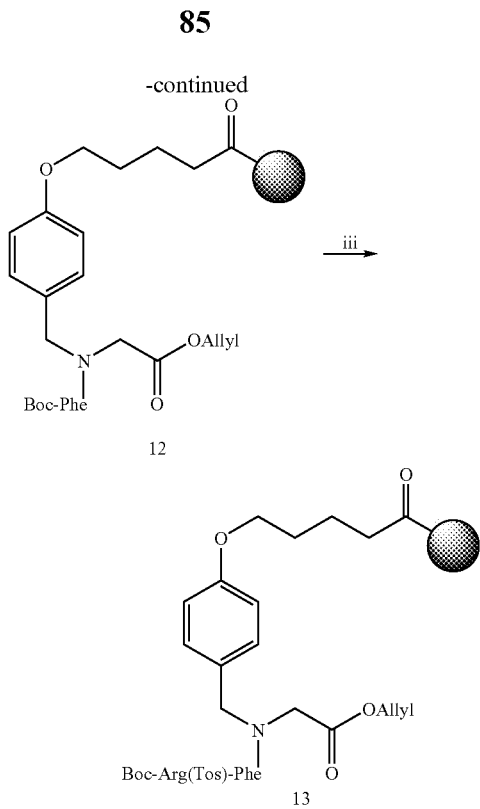

*Reagents: (i) H-Gly-OAllyl, NaCNBH$_3$, MeOH, rt, 3 h; (ii) Boc-Phe$_2$-O, DCM, rt, 6 h; (iii) Boc-Arg(Tos)-OH, HBTU, DIEA, DMF.

Scheme 15

*Reagents: i TFA:DCM (40:60), 2×5 min; ii, Fmoc-Try(Boc)-OH, HBTU, DIEA, DMF, 1 h.; ii, piperidine:DMF, 1:1, 2×5 min; iv, HnB 2, NaBH$_4$, DMF, rt, 1 h; v, 3 equiv. Pd(Ph$_3$)$_4$, CH$_3$Cl:HOAc:NMM, 37:2:1, r.t, 3 h; vi HF:p-cresol, 1:1.

Linear Tyr-Arg-Phe-Gly id SEQ ID NO:70.

Scheme 16

Addition of Fmoc-Tyr(Boc)-OH to 13 using in situ neutralisation protocols and HBTU activation resulted in the linear peptide 14 (Scheme 16). Allyl deprotection of 14 using Pd(PPh$_3$)$_4$ followed by a final TFA treatment gave the desired linear peptide 15 on resin, while removal of the Fmoc protecting group and reductive amination using HnB and NaBH$_4$ followed once again by allyl removal gave the desired linear peptide 16. [HnB]Tyr-Arg-Phe-Gly is SEQ ID NO:4.

Figure 8:
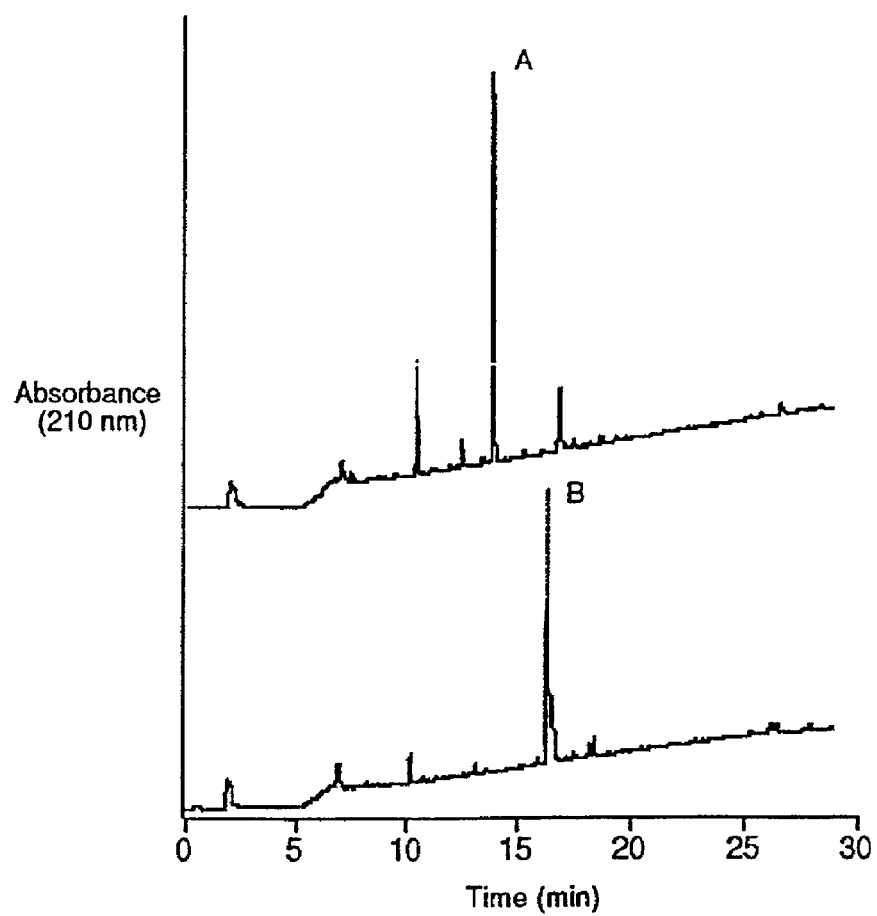
FIG. 8 shows results of crude HPLC of linear peptides 17 and 18 using backbone linkage. A=H-Tyr-Arg-Phe-Gly-OH 17 (SEQ ID NO:3); B=[HnB]Tyr-Arg-Phe-Gly-OH 18 (SEQ ID NO:4); Cleavage was performed using HF:p-cresol, 9:1, −5° C., 1 h.

To show purity and ease of synthesis, the peptides were then cleaved (HF:p-cresol, 9:1) to give linear peptides 17 and 18. The HPLC profile of the linear peptides is shown in FIG. 8.

Figure 9:
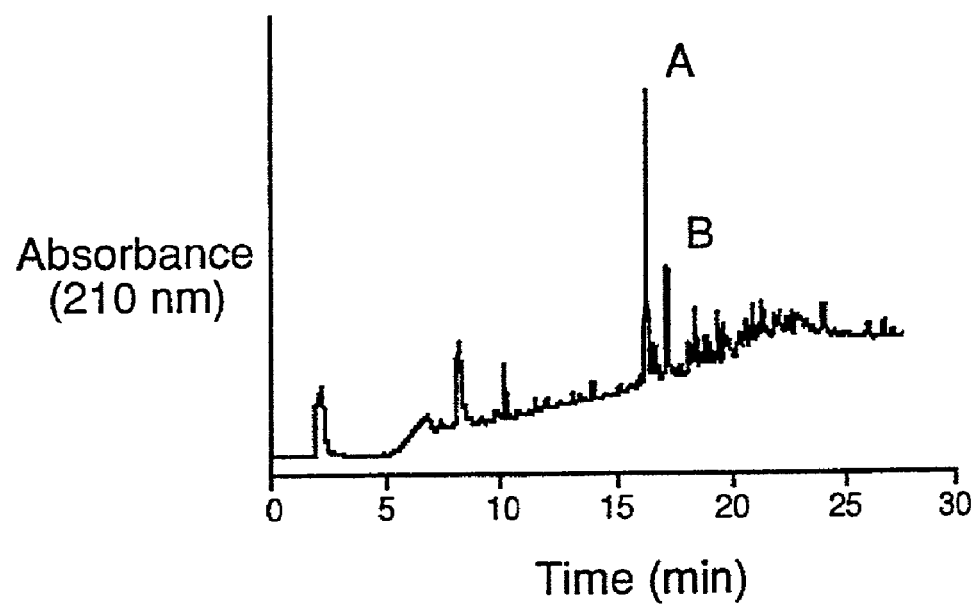
FIG. 9 shows the results of crude HPLC for the cyclisation of linear peptides 16 using backbone linkage. A=[HnB]Tyr-Arg-Phe-Gly-OH 18 (SEQ ID NO:4); B=cyclo-[[HnB]Tyr-Arg-Phe-Gly] 21 (SEQ ID NO:5). Cyclisation was performed using BOP, DIEA, 3 days, while cleavage was performed using HF p-cresol, 9:1, −5° C., 1 h.

Cyclisation of the linear peptides 15 and 16 was performed using BOP, DIEA in DMF over 3 days. For linear peptide 15, without the presence of the [HnB] auxiliary, cyclisation followed by HF cleavage did not produce the desired product. A series of oligomer by-products was detected by both HPLC and LC/MS. The cyclisation of the linear peptide 16, containing a [HnB] auxiliary, resulted in the desired cyclic product. The reactions are summarised in Scheme 17, and the HPLC profile of the cyclic peptides is shown in FIG. 9.

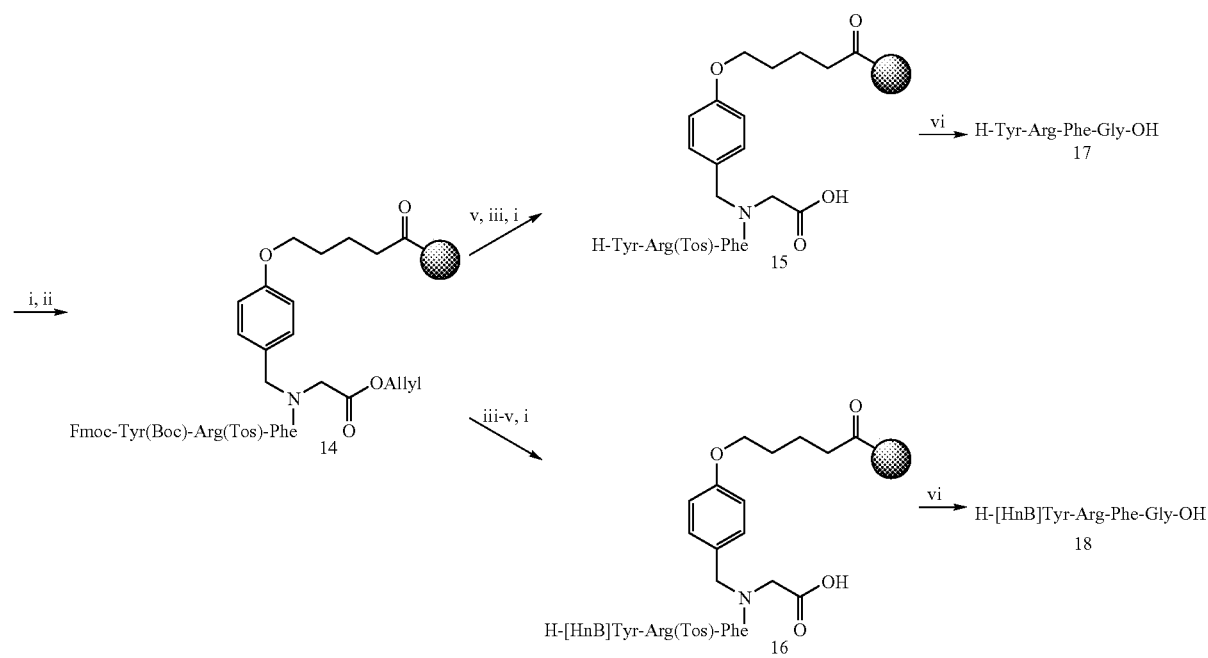

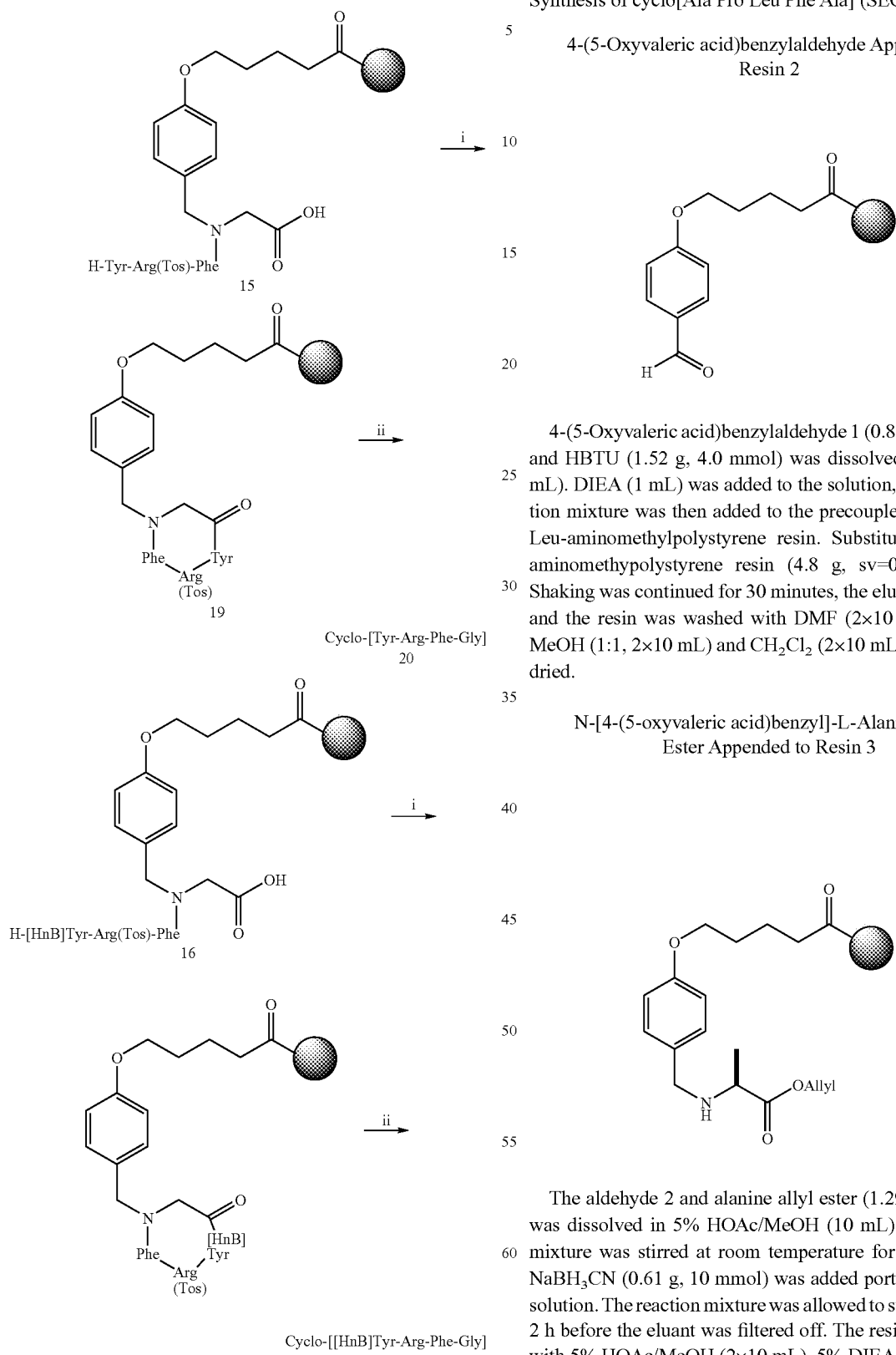

Experimental to Example 11

Synthesis of cyclo[Ala Pro Leu Phe Ala] (SEQ ID NO:72)

4-(5-Oxyvaleric acid)benzylaldehyde Appended to Resin 2

4-(5-Oxyvaleric acid)benzylaldehyde 1 (0.89 g, 4.0 mmol) and HBTU (1.52 g, 4.0 mmol) was dissolved in DMF (10 mL). DIEA (1 mL) was added to the solution, and this reaction mixture was then added to the precoupled H-Gly-Leu-Leu-aminomethylpolystyrene resin. Substitution value of aminomethypolystyrene resin (4.8 g, sv=0.21 mmol/g). Shaking was continued for 30 minutes, the eluant filtered off and the resin was washed with DMF (2×10 mL), $CH_2Cl_2$ MeOH (1:1, 2×10 mL) and $CH_2Cl_2$ (2×10 mL) before being dried.

N-[4-(5-oxyvaleric acid)benzyl]-L-Alanine Allyl Ester Appended to Resin 3

The aldehyde 2 and alanine allyl ester (1.29 g, 10 mmol) was dissolved in 5% HOAc/MeOH (10 mL). The reaction mixture was stirred at room temperature for 5 min before $NaBH_3CN$ (0.61 g, 10 mmol) was added portionwise to the solution. The reaction mixture was allowed to stir for a further 2 h before the eluant was filtered off. The resin was washed with 5% HOAc/MeOH (2×10 mL), 5% DIEA/MeOH (3×10 mL), $CH_2Cl_2$: MeOH (1:1, 2×10 mL) and $CH_2Cl_2$ (2×10 mL) before being dried.

89

Boc-Pro-[N-(4-(5-oxyvaleric acid)benzyl)]-L-Alanine Allyl Ester Appended to Resin 4

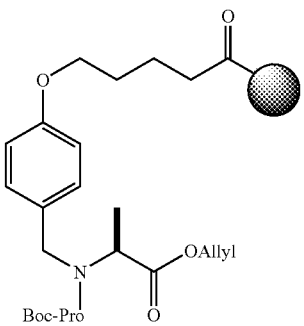

Boc-Pro-OH (4.31 g, 20.0 mmol) was dissolved in $CH_2Cl_2$ (10 mL), to which was added diisopropylcarbodiimide DIC (1.26 g, 10.0 mmol). After activation for 10-15 min to form the symmetric anhydride, the mixture was filtered and the filtrate was added to the resin 3. The reaction was shaken at r.t. for 16 h before the eluant was filtered off. The resin was washed with $CH_2Cl_2$ (5×10 mL) before being dried.

H-Ala-Phe-Leu-Pro-[N-(4-(5-oxyvaleric acid)benzyl)]-L-Alanine Allyl Ester Appended to Resin 5 (SEQ ID NO:73)

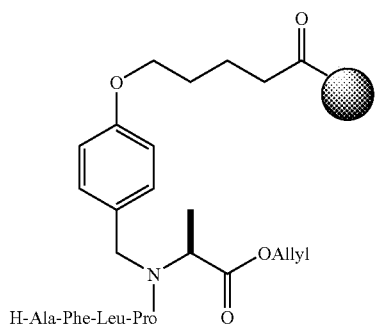

Te peptide 5 was synthesised in stepwise fashion by established methods using in situ neutralisation/HBtU activation protocols for Boc chemistry. Coupling reactions were monitored by quantitative ninhydrin assay, and were typically >99.9%.

90

N-(2-hydroxy-4-nitrobenzyl)-Ala-Phe-Leu-Pro-[N-(4-(5-oxyvaleric acid)benzyl)]-L-Alanine Allyl Ester Appended to Resin 6 (SEQ ID NO:74)

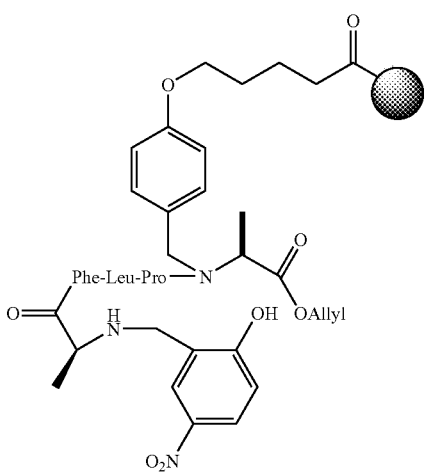

2-Hydroxy 4-nitro-benzaldehyde (1.67 g, 10 mmol) and the peptide on resin 5 was stirred in DMF (4 mL) at r.t. for 5 min. $NaBH_4$ (0.34 g, 10 mmol) was added portionwise to the solution, and the reaction mixture allowed to stir for a further 1 h before the eluant was filtered off. The addition of the benzaldehyde and $NaBH_4$ in DMF (10 mL) was then repeated once. The resin was washed with DMF (3×10 mL), $CH_2Cl_2$:MeOH (1:1, 2×10 mL) and $CH_2Cl_2$ (2×10 mL) before being dried.

The allyl protecting group was achieved by the addition of tetrakis (triphenylphosphine) palladium [$Pd(PPh_3)_4$] (1.74 g, 0.5 mmol) to the resin in a solution of $CHCl_3$:HOAc:NMM (37.2:1) and continued stirring for 14 h. The solvent was removed and the residue was washed with a 10% solution of diethyldithiocarbamic acid (sodium salt trihydrate [$(C_2H_5)_2N_2CS_2Na\cdot3H_2O$]) in DMF (2×10 mL), then with DMF (2×10 mL), MeOH:$CH_2Cl_2$ 1:1 (2×10 mL) and finally with $CH_2Cl_2$ (2×10 mL).

A small amount of the peptide 7 was cleaved from the resin (100 mg, 0.166 mmol/g) using HF:p-cresol, 5.5 mL, 10:1, for 1 h at −5° C. After removal of the HF under reduced pressure, the crude peptide was precipitated in anhydrous ether, filtered, dissolved in the HPLC buffer and lyophilized Analytical HPLC (20-70% B over 20 min) showed only one peak; ES-MS $M_r$ 668.4 (calcd 669.3).

Cyclo-[N-(2-hydroxy-4-nitrobenzyl)-Ala-Phe-Leu-Pro-Ala] 10 (SEQ ID NO:75)

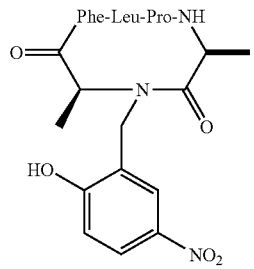

DIC (6.7 mg, 0.04 mmol) was added to a solution of the peptide on resin 7 (200 mg, sv=0.176 mmol/g) in DMSO (4 mL). DIEA (? mL) was added dropwise to the solution and the reaction mixture was left to stir at r.t. for 1 h before being heated to 70° C. for 2 h. The eluant was filtered off and washed with DMF (3×10 mL), $CH_2Cl_2$:MeOH (1:1, 2×10 mL) and $CH_2Cl_2$ (2×10 mL) before being dried. The cyclic peptide 10 was cleaved from resin using HF:p-cresol, 5.5 mL, 10:1, for 1 h at 0° C. After removal of the HF under reduced pressure, the crude peptide was precipitated in anhydrous ether before being dissolved in the HPLC buffer and lyophilized. Analytical HPLC (20-70% B over 20 min) showed two peaks; a) linear peptide ES-MS $M_r$ 668.4 (calcd 669.3), and cyclized material ES-MS $M_r$ 650.4 (calcd 650.3).

Experimental to the Synthesis of a Cyclic Tetrapeptide cyclo[[Hnb]Tyr Arg Phe Gly] (SEQ ID NO:5)

Peptide Synthesis. All linear peptides were chemically synthesised stepwise using either Fmoc or Boc protecting groups and in situ HBTU activation protocols, as previously described by Schnölzer, 1992. Coupling efficiencies were determined by the quantitative ninhydrin test and recoupled where necessary to obtain >99.5% efficiency. Allyl deprotection was performed using 3 equiv. $Pd(Ph_3)_4$, $CH_3Cl$:HOAc:NMM, 37:2:1, r.t, 3 h, as previously reported by Kates, 1993.

Reductive amination. The selected auxiliary-aldehyde (0.1M) was dissolved in MeOH/DMF (1:1) or DMF/AcOH (100:1) and added to the resin-bound Boc-deprotected peptide (2 equivalents to resin-bound amine). After 5 min the resin was filtered and a second portion of aldehyde added. After another 5 min the resin was filtered and washed with MeOH/DMF (1:1) or DMF. $NaBH_4$ (10eq) in MeOH/DMF (1:3) was added and the reaction mixture left standing for 5 min. The resin was again filtered and washed with MeOH/DMF (1:3), DMF, MeOH/DCM (1:1), and air-dried prior to cleavage.

Cleavage. Peptides were cleaved as follows: 250 mg of resin were mixed with 1 mL p-cresol and 10 mL HF added at 0° C. and the mixture stirred at 0° C. for 1 h. After evaporation of the HF the crude product was precipitated and washed with ether (2×10 mL). The precipitate was then dissolved in 50% $CH_3CN$ in water (0.095% TFA) for HPLC purification (as above).

H-Tyr-Arg-Phe-Gly-OH 17 (SEQ ID NO:70). The linear peptide was isolated in % yield: ES-MS Mr 542.2, calcd for $C_{26}H_{36}N_7O_6$, 542.3 (monoisotopic).

H-[HnB]Tyr-Arg-Phe-Gly-OH 18 (SEQ ID NO:4). The linear peptide was isolated in % yield: ES-MS Mr 693.1, calcd for $C_{33}H_{41}N_8O_9$, 693.3 (monoisotopic).

Cyclo-[[HnB]Tyr-Arg-Phe-Gly] 22 (SEQ ID NO:5). Cyclisation of H-[HnB]Tyr-Arg-Phe-Gly-OH on backbone linker 18 produced the cyclo-[[HnB]Tyr-Arg-Phe-Gly] in % yield. ES-MS Mr 675.3, calcd for $C_{33}H_{34}N_7O_8$, 675.3 (monoisotopic).

EXAMPLE 12

Ring Contraction, Backbone Substitution and Backbone Linker

Our current backbone linkers can be attached to any atom of the peptide backbone. As the data in Table 3 suggest, more than one N α-substitutent results in the best yields of cyclic tetrapeptides for the examples studied. In combination with ring contraction this provides a powerful approach for the synthesis of cyclic peptides.

The peptide outlined below (SEQ ID NO:76) is synthesized using this combined approach. This peptide contains 2 N α-substituents (one is the linker L) and a ring contraction auxiliary. The peptide is cyclised and the purity and yields of products are examined. Reversible Na-substitution in replacement of methylation is also investigated.

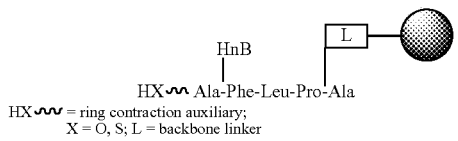

HX∿∿ = ring contraction auxiliary;
X = O, S; L = backbone linker

EXAMPLE 13

Biological Activity of cyclo[Tyr-Arg-Phe-Gly] (SEQ ID NO:42) and cyclo[Tyr-Arg-D-Phe-Gly] (SEQ ID NO:42)

Drugs with opioid receptor binding activity are therapeutically useful for pain relief and for detoxification of opiate addicts, and morphine and naloxone are widely used as analgesics and antidote, respectively. Morphine has undesirable side effects, such as drug dependency and respiratory depression, and consequently there is a clear medical need for more efficacious drugs with fewer or less severe side effects.

Figure 10:
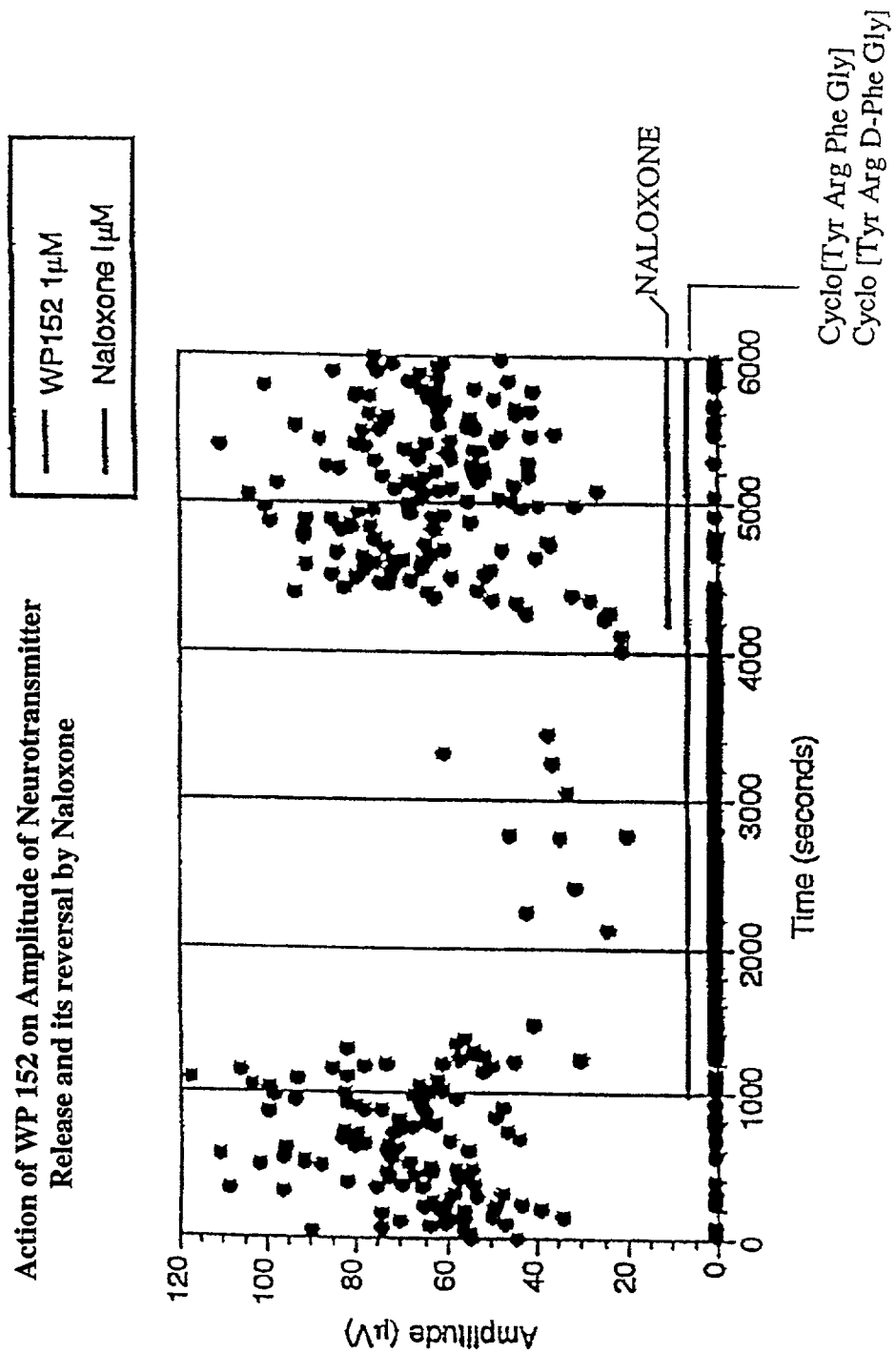
FIG. 10 shows the effect of compounds (1 μM) on evoked excitatory junction currents (measure of transmitter release) from sympathetic varicosities of the mouse vas deferens. Each filled circle represents an EJC recorded during 100 minutes. Failure to record an EJC is indicated by filled circles on zero of the y-axis. The lower horizontal line indicates when the mixture of cyclic tetrapeptides (1 μM) was applied to the tissue bathing solution and the upper horizontal line when naloxone (1 μM) was added to the tissue bathing solution. Note that the mixture of tetrapeptides (1 μM) greatly reduces the EJC amplitude and frequency, and that the opiate antagonist (naloxone) inhibits this effect. Cyclo [Tyr-Arg-Phe-Gly] is SEQ ID NO:42.
Figure 11:
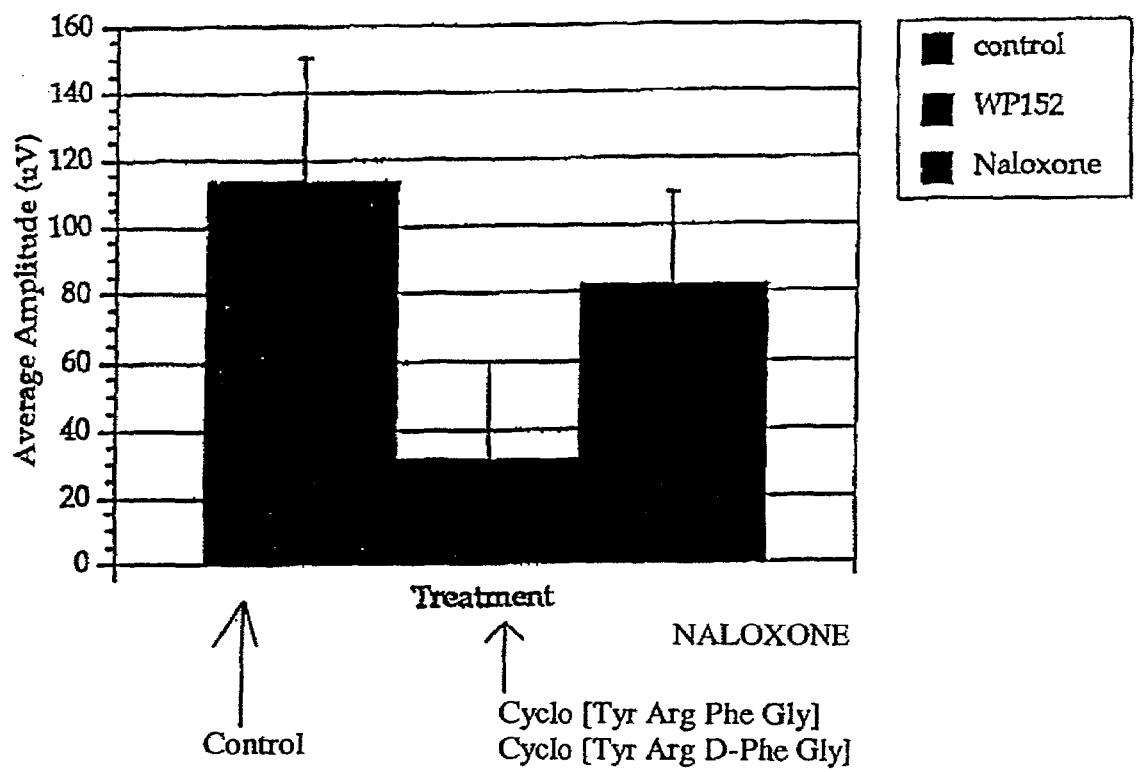
FIG. 11 shows the effect of a mixture of cyclic tetrapeptides (1 µM) on the average excitatory junction current (EJC) recorded from sympathetic varicosities of mouse vas deferens. Each bar is the average of at least 60 recordings, and the vertical lines show the standard deviation of the mean. Note there was a highly significant decrease in EJC amplitude and frequency following 20 minutes of cyclic tetrapeptide exposure of the preparation, and that this effect was reversed by naloxone. Cyclo [Tyr-Arg-Phe-Gly] is SEQ ID NO:42.

Demorphin is a opioid heptapeptide isolated from the skin of South American frogs, and has the following sequence; {H-Tyr-D-Ala-Phe-Gly-Tyr-Pro-Ser-NH2; SEQ ID NO:71). The tetrapeptide analogues (H-Tyr-D-Ala-Phe-Gly-NH-Y; SEQ ID NO:29) are potent analgesics when administered by intracerebroventricular injection. In Example 3 we synthesised the cyclic tetrapeptides cyclo[Tyr-Arg-Phe-Gly] (SEQ ID NO:42) and cyclo[Tyr-Arg-D-Phe-Gly] (SEQ ID NO:42) designated WP 152 using our combination strategies. FIGS. 10 and 11 shows the effect of these compounds on the focal extracellular recording of evoked excitary for junction currents (EJC) from visualised sympathetic varicosities, measured as described by (Lavidis (1995)). These results illustrates that the mixture of compounds greatly reduces transmitter release. The effect is reversed by the addition of naloxone, strongly suggesting that one or both of the compounds are potent μ-opiate agonists.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

REFERENCES

Backes, B. J. and Ellman, J. A.
J. Am. Chem. Soc., 1994 116 11171-11172
Backes, B. J., Virgilio, A. A. and Ellman, J. A.
J. Am. Chem. Soc., 1996 118 306 55-6
Bauer, L and Suresh, K. S.
J. Org. Chem., 1963 28 1604-1608
Beusen, D. D., Zabrocki, J., Slomczynska, U., Head, R. D., Kao, J. L., and Marshall, G. R.
Biopolymers, 1995 36 181-200
Botti, P., Pallin, T. D. and Tam, J. P.
J. Am. Chem. Soc., 1996 1996 10018-10024
Brady, S. F., Paleveda, W. J., Arison, B. H., Freidinger, R. M., Nutt, R. F. and Veber, D. F.
In Proceedings of the 8th American Peptide Symposium; Pierce Chemical Company, Rockford: 1983 pp 127
Camamero, J. A. and Muir, T. W.
Chem. Commun., 1997 1369-1370,
Castro, B., Doromy, J. R., Evin, G. and Selve, C.
Tet. Lett., 1975 14 1219
Cavelier-Frontin, F., Achmad, S., Verducci, J., Jacquier, R., and Pepe, G.
J. Mol. Struc. (Theochem), 1993 286 125
Ehrlich, A., Heyne, H.-A., Winter, R., Betermann, M., Haber, H., Carpino, L. and Bienert, M.
J. Org. Chem., 1996 61 8831-8838
Ehrlich, A., Klose, J., Heyne, H., Beyermann, M., Carpino, L. A. and Bienert, M.
In Peptides: Chemistry, Structure and Biology; Mayflower Scientific Ltd: 1996 75-76
Flanigan, E. and Marshall, G. R.
Tet. Lett., 1970 27 2403-2406
Flanigan, E.
"Studies on the solid phase synthesis of cyclic peptides", *PhD Dissertation*, Washington University, St Louis, Mo., 1971,
Freidinger, R. M., Perlow, D. S, and Veber, D. F.
J. Org. Chem, 1982 59 104-109
Freudenberg, K., Heel, W.,
Chem. Ber. 1953, 86, 190-196
Fridkin, M., Patchornik, A. and Katchalski, E.
J. Am. Chem. Soc., 1965 87 4647-4648
Fridkin, M., Patchornik, A. and Katchalski, E.
J. Am. Chem. Soc., 1968 90 2953-2957
Fridkin, M., Patchornik, A. and Katfchalski, E.
Biochemistry, 1972 11 466-471
Heavner, G. A., Audhya, T., Doyle, D., Tjoeng, F. S, and Goldstein, G.
Int. J. Pept. Prot. Res., 1991 37 198
Izumiya, N., Kato, T. and Waki, M.
Biopolymers, 1981 20 1785
Jensen, K. J., Songster, M. F., Vagner, J., Alsina, J., Albericio, F. and Barany, G.
In 14th American Peptide Symposium; Mayflower Scientific Ltd.: 1996 30-32
Jensen et al
J. Am. Chem. Soc., 1998 120 5441-52
Kenner, G. W., McDermott, J. R. and Sheppard, R. C.
J. Chem. Soc., Chem. Commun., 1971 636-637
Knorr, R., Trzeciak, A., Bannworth, W., and Gillessen, D.
Tet. Lett., 1989 30 1927
Laufer, D. A., Chapman, T. M., Marlborough, D. I., Vaidya, V. M. and Blout, E. R.
J. Am. Chem. Soc., 1968 90 2696-2698
Lavidis, N. A.
Brit. J. Pharmacol, 1995 116 2852-2859
Marshall, G. R., Humblet, C., Van Opdenbosch, N. and Zabrocki, J.
In Peptides: Synthesis, Structure and Function; Pierce Chemical Co., Rockford, Ill.: 1981 pp 669-672
Marshall, D. L. and Liener, I.
J. Org. Chem, 1970 35 867-868
Moore, M. L.
International Publication Number WO95/34577, 1995
Nagai, U. and Sato, K.
Tetrahedron Letters, 1985 26 647-650.
Osapay, G., Profit, A. and Taylor, J. W.
Tet. Lett., 1990 31 6121.
Osapay, G. and Taylor, J. W.
J. Am. Chem. Soc., 1990 112 6046
Osby, J. O., Martin, M. G., Ganem, B.,
Tetrahedron Lett. 1984, 25, 2093-2096
Richter, L. S., Tom, J. Y. K. and Burnier, J.
Tet. Lett., 1994 35 5547-5550
Rivaille, P., Gautron, J. P., Castro, B. and Milhaud, G.
Tetrahedron, 1980 36 3413-3419.
Schmidt, R. and Neubert, K.
Int. J. Pept. Prot. Res., 1991 37 502
Shao, Y., Lu, W. and Kent., S.
Tetrahedron Letters, 1998 39 431-440
Smythe, M. L. and von Itzstein, M.
J. Am. Chem. Soc., 1994 116 2725-2733
Zabrocki, J., Dunbar, J. B., Marshall, K. W., Toth, M. V. and Marshall, G. R.
J. Org. Chem., 1992 57 202-209

The claims defining the invention are as follows:

1. A method of synthesizing a cyclic peptide or peptidomimetic compound of General Formula I

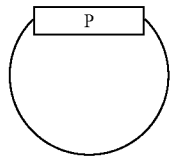

General Formula I in which the cycle is a monocycle, bicycle or higher order cyclic peptide or peptidomimetic compound comprising 2 to 15 monomers, which is carried out in solution, comprising the steps of:

a) preparing a linear peptide or peptidomimetic compound of General Formula III

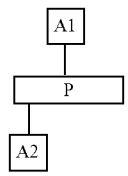

General Formula III where P is a linear peptide or peptidomimetic compound of 2 to 15 monomers, A1 and A2 are substituents on P;

A1 is one or more reversible N-substituents, on the peptide backbone, or is a chemical moiety that forces a cis conformation of the backbone, and A2 is a covalently-bonded group of atoms comprising a reactive functionality to form an initial large cyclic peptide prior to ring contraction to the desired substituted cyclic peptide;

b) activating the C-terminus to form a cyclic peptide or peptidomimetic compound of General Formula IV;

General Formula IV c) permitting the peptide or peptidomimetic compound of General Formula IV to rearrange via a ring contraction reaction to form a cyclic peptide or peptidomimetic compound of General Formula V; and

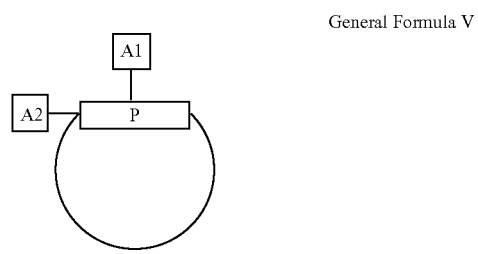

General Formula V d) subjecting the cyclic peptide or peptidomimetic compound of General Formula V to a deprotection reaction to remove the A1 and A2 groups to yield the desired cyclic peptide or peptidomimetic compound of General Formula I.

2. The method of claim 1, in which P is a linear peptide of 2 to 10 monomers.

3. The method of claim 2, in which P is a linear peptide of 2 to 5 monomers.

4. The method of claim 1, in which A1 is a 2-hydroxy-4-methoxybenzyl, 2-hydroxybenzyl or 2-hydroxy-6-nitrobenzyl substituent.

5. The method of claim 1, in which A2 comprises a nucleophile that reacts rapidly with a C-terminus to form an initial large ring, which then contracts either spontaneously, or upon heating or additional chemical treatment.

6. The method of claim 5, in which A2 comprises thiol or hydroxyl.

7. The method of claim 1, in which A2 is formed by reacting an amino nitrogen in P with a compound of general formula:

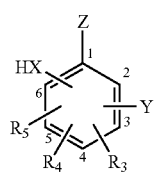

in which the ring:
(a) is an aromatic 6-membered ring;
(b) comprises 3 carbon atoms substituted respectively by XH, Z and Y; and
(c) is additionally substituted, in which
XH is OH, SH, CH$_2$OH, or CH$_2$SH;
Y is an electron-withdrawing group;
Z is any group which allows the formation of a covalent carbon-nitrogen bond; and
R$^3$, R$^4$ and R$^5$ are each independently hydrogen, alkyl, aryl, arylalkyl, heteroaryl, alkoxy, aryloxy, XH or Y, or a covalent linkage to a solid support, and
in which R$^3$ and R$^4$ or R$^4$ and R$^5$ can optionally together with the ring form a 5-, 6-, or 7-membered ring.

8. The method of claim 1, in which the ring contraction reaction occurs spontaneously.

9. A method of performing solid phase synthesis of a cyclic peptide, comprising the steps of:

a) synthesizing a linear solid support-bound peptide of General Formula XIII,

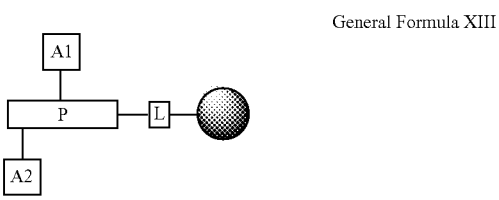

General Formula XIII where P is a linear peptide of 2 to 15 monomers, A1 and A2 are substituents on P;

A1 is one or more N-substituents, either reversible or non-reversible, on the peptide backbone, or is a chemical moiety that forces a cis conformation of the backbone, and A2 is a covalently-bonded group of atoms comprising a reactive functionality to form an initial large cyclic peptide prior to ring contraction to the desired substituted cyclic peptide; and L is a linker between any atom of the peptide and the solid support;

b) subjecting the peptide of General Formula XIII to cyclization and concomitant cleavage from the solid support to yield a cyclic peptide of General Formula XIV,

General Formula XIV c) subjecting the cyclic peptide of General Formula XIV to ring contraction, and d) if A1 is a reversible substituent, cleaving the groups A1 and A2 to yield the desired cyclic peptide of General Formula I:

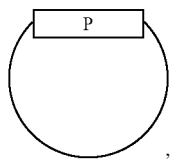

10. The method of claim 9, in which one or more of the monomers carries a side chain protecting group.

11. The method of claim 9, in which A2 is formed by reacting an amine nitrogen in P with a compound selected from the group consisting of:

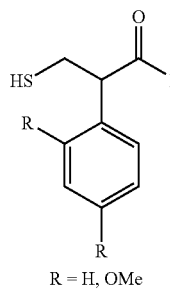
R = H, OMe

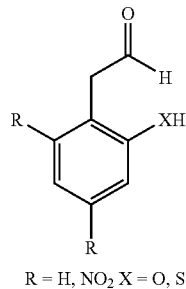
R = H, NO₂ X = O, S and
wherein A2 facilitates contraction of said ring to form said cyclic peptide.

12. The method of claim 9, in which A2 is 6-nitro-2-hydroxybenzyl, 4-nitro-2-hydroxybenzyl or 5-nitro-2-hydroxybenzyl.

13. The method of claim 9, in which the ring contraction reaction occurs spontaneously.

14. A method of performing solid phase synthesis of a cyclic peptide, comprising the steps of;
a) synthesizing a linear solid support-bound peptide of General Formula XIII, General Formula XIII

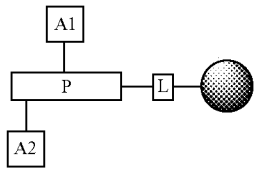

where P is a linear peptide of 2 to 15 monomers, A1 and A2 are substituents on P;
A1 is one or more N-substituents, either reversible or non-reversible, on the peptide backbone, or is a chemical moiety that forces a cis conformation of the backbone, and
A2 is a covalently-bonded group of atoms comprising a reactive functionality to form an initial large cyclic peptide prior to ring contraction to the desired substituted cyclic peptide; and
L is a linker between any atom of the peptide and the solid support; and
b) subjecting the linear peptide to cyclization on the solid support to yield a cyclic peptide of General Formula XV, General Formula XV

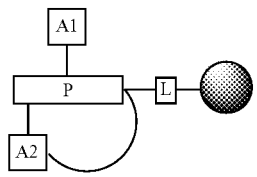

c) subjecting the cyclic peptide to ring contraction to yield a cyclic peptide of General Formula XVI, General Formula XVI

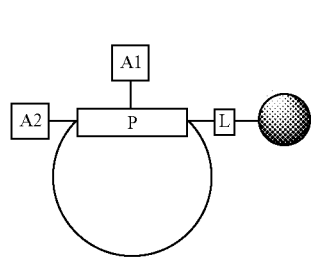

and either
d) cleaving groups A1 and A2 while the peptide is bound to the solid support to yield a resin-bound cyclic peptide of General Formula II, or General Formula II

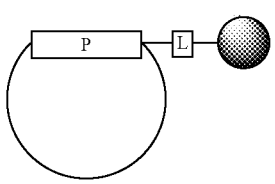

e) subjecting the cyclic peptide to deprotection and concomitant cleavage from the solid support to yield the desired cyclic peptide of General Formula I:

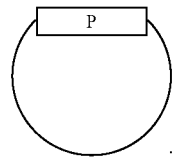

15. The method of claim 14, in which side chain deprotection of the peptide, removal of A1 and cleavage from the solid support are performed separately.

16. The method of claim 14, in which side chain deprotection of the peptide, removal of A1 and cleavage from the solid support are performed concurrently.

17. The method of claim 14, in which one or more of the monomers carries a side chain protecting group.

18. The method of claim 14, in which A1 is a cis-amide bond surrogate.

19. The method of claim 18, in which the cis-amide bond surrogate is a tetrazole.

20. The method of claim 14, in which A2 is formed by reacting an amine nitrogen in P with a compound selected from the group consisting of:

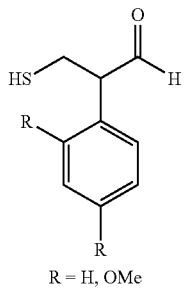
R = H, OMe

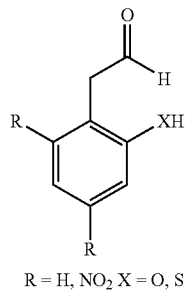
R = H, NO₂ X = O, S and
wherein A2 facilitates contraction of said ring to form said cyclic peptide.

21. The method of claim 14, in which A2 is 6-nitro-2-hydroxybenzyl, 4-nitro-2-hydroxybenzyl or 5-nitro-2-hydroxybenzyl.

22. The method of claim 14, in which the ring contraction reaction occurs spontaneously.

23. A method of synthesizing a cyclic peptide or peptidomimetic compound, which is carried out in solution, comprising the steps of:
   a) preparing a linear peptide or peptidomimetic compound of General Formula III

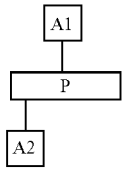

General Formula III where P is a linear peptide or peptidomimetic compound of 2 to 15 monomers, A1 and A2 are substituents on P;
A1 is one or more N-substituents, either reversible or non-reversible, on the peptide backbone, or is a chemical moiety that forces a cis conformation of the backbone, and A2 is a covalently-bonded group of atoms comprising a reactive functionality to form an initial large cyclic peptide prior to ring contraction to the desired substituted cyclic peptide;
   b) activating the C-terminus to form a cyclic peptide or peptidomimetic compound of General Formula IV:

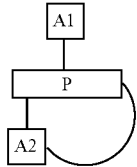

General Formula IV c) permitting the peptide or peptidomimetic compound of General Formula IV to rearrange via a ring contraction reaction to form a cyclic peptide or peptidomimetic compound of General Formula V;

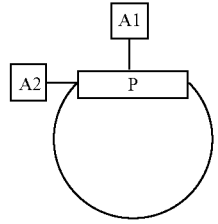

General Formula V wherein either the A1 group or the A2 group is left attached to the peptide, or both A1 and A2 are left attached to the peptide.

24. The method of claim 23, in which: (a) A1 is subsequently linked to said solid support or said another cyclic peptide or peptidomimetic compound; (b) A2 is subsequently linked to said solid support or to said another cyclic peptide or peptidomimetic compound; or (c) both A1 and A2 are subsequently linked to said solid support or to said another cyclic peptide or peptidomimetic compound.

* * * * *